US012383606B2

(12) United States Patent
Lencer et al.

(10) Patent No.: US 12,383,606 B2
(45) Date of Patent: Aug. 12, 2025

(54) SHORT CHAIN CERAMIDE-BASED LIPIDS AND USES THEREOF

(71) Applicant: Children's Medical Center Corporation, Boston, MA (US)

(72) Inventors: Wayne I. Lencer, Jamaica Plain, MA (US); Daniel J F Chinnapen, Quincy, MA (US)

(73) Assignee: Children's Medical Center Corporation, Boston, MA (US)

( * ) Notice: Subject to any disclaimer, the term of this patent is extended or adjusted under 35 U.S.C. 154(b) by 272 days.

(21) Appl. No.: 18/087,273

(22) Filed: Dec. 22, 2022

(65) Prior Publication Data

US 2023/0132279 A1 Apr. 27, 2023

Related U.S. Application Data

(62) Division of application No. 16/759,536, filed as application No. PCT/US2018/057787 on Oct. 26, 2018, now Pat. No. 11,559,568.

(60) Provisional application No. 62/643,680, filed on Mar. 15, 2018, provisional application No. 62/578,341, filed on Oct. 27, 2017.

(51) Int. Cl.
*A61K 47/54* (2017.01)
*A61K 38/22* (2006.01)
*A61K 38/26* (2006.01)
*A61K 39/00* (2006.01)
*A61K 39/395* (2006.01)

(52) U.S. Cl.
CPC .............. *A61K 38/26* (2013.01); *A61K 38/22* (2013.01); *A61K 39/00* (2013.01); *A61K 39/395* (2013.01); *A61K 47/54* (2017.08); *A61K 47/549* (2017.08)

(58) Field of Classification Search
CPC ..... A61K 9/1617; A61K 47/543; A61K 47/65
See application file for complete search history.

(56) References Cited

U.S. PATENT DOCUMENTS

| | | | |
|---|---|---|---|
| 4,610,868 A | 9/1986 | Fountain et al. | |
| 5,149,794 A | 9/1992 | Yatvin et al. | |
| 5,366,963 A | 11/1994 | Ladisch | |
| 5,846,951 A | 12/1998 | Gregoriadis | |
| 5,965,519 A | 10/1999 | Yatvin et al. | |
| 6,193,997 B1 | 2/2001 | Modi | |
| 9,457,097 B2 | 10/2016 | Lencer et al. | |
| 10,765,757 B2 | 9/2020 | Lencer et al. | |
| 10,806,793 B2 | 10/2020 | Lencer et al. | |
| 11,559,568 B2 | 1/2023 | Lencer et al. | |
| 11,771,771 B2 | 10/2023 | Lencer et al. | |
| 2003/0114415 A1 | 6/2003 | Wurtman et al. | |
| 2005/0281772 A1 | 12/2005 | Bromley et al. | |
| 2006/0052316 A1 | 3/2006 | Porcelli | |
| 2006/0171956 A1 | 8/2006 | Bareholz et al. |
| 2007/0231344 A1 | 10/2007 | Leadbetter et al. |
| 2008/0064645 A1 | 3/2008 | Pagano et al. |
| 2008/0299168 A1 | 12/2008 | Dadey et al. |
| 2010/0092425 A1 | 4/2010 | von Andrian et al. |
| 2012/0252727 A1 | 10/2012 | Lencer et al. |
| 2012/0277158 A1 | 11/2012 | Castaigne et al. |
| 2014/0171372 A1 | 6/2014 | Lalezari et al. |
| 2016/0266097 A1 | 9/2016 | Gagnon |
| 2017/0095563 A1 | 4/2017 | Lencer et al. |
| 2018/0133332 A1 | 5/2018 | Lencer et al. |
| 2018/0333499 A9 | 11/2018 | Lencer et al. |
| 2020/0289619 A1 | 9/2020 | Lencer et al. |
| 2021/0338823 A9 | 11/2021 | Lencer et al. |
| 2024/0042042 A1 | 2/2024 | Lencer et al. |

FOREIGN PATENT DOCUMENTS

| | | |
|---|---|---|
| EP | 1972349 A1 | 9/2008 |
| JP | H07-509227 A | 10/1995 |
| JP | 2016-509013 A | 3/2016 |
| WO | 94/01138 A1 | 1/1994 |
| WO | 99/15201 A1 | 4/1999 |
| WO | 99/43356 A1 | 9/1999 |
| WO | 03/106474 A2 | 12/2003 |
| WO | 2005/097199 A1 | 10/2005 |
| WO | 08/111916 A1 | 9/2008 |
| WO | 2010/027479 A2 | 3/2010 |
| WO | 2013/150532 A1 | 10/2013 |
| WO | 2016/118697 A9 | 7/2016 |
| WO | 2018/031933 A2 | 2/2018 |

OTHER PUBLICATIONS

Ahn et al., Induction of apoptosis by sphingosine, sphinganine, and C(2)-ceramide in human colon cancer cells, but not by C(2)-dihydroceramide. Anticancer Res. Jul. 2010;30(7):2881-4. Erratum in: Anticancer Res. Sep. 2010;30(9):3851.
Albrecht et al., Synthesis and mass spectrometric characterization of digoxigenin and biotin labeled ganglioside GM1 and their uptake by and metabolism in cultured cells. Chem Phys Lipids. Mar. 28, 1997;86(1):37-50. doi: 10.1016/s0009-3084(97)02658-3.
Allan, D., Lipid metabolic changes caused by short-chain ceramides and the connection with apoptosis. Biochem J. Feb. 1, 2000;345 Pt 3(Pt 3):603-10. PMID: 10642519.
Ashkenazi et al., Sphingopeptides: dihydrosphingosine-based fusion inhibitors against wild-type and enfuvirtide-resistant HIV-1. FASEB J. Nov. 2012;26(11):4628-36. doi: 10.1096/fj.12-215111. Epub Aug. 7, 2012.

(Continued)

*Primary Examiner* — Gyan Chandra
(74) *Attorney, Agent, or Firm* — Wolf, Greenfield & Sacks, P.C.

(57) ABSTRACT

Provided herein, in some aspects, are delivery vehicles comprising a glycosphingolipid and an agent to be delivered attached to the glycosphingolipid. In some embodiments, the glycosphingolipid comprises an oligosaccharide and a short chain (e.g., C0-C3) ceramide. In some embodiments, the agent to be delivered is a therapeutic agent. The glycosphingolipid is able to deliver the agent to a cell or to a cellular compartment, as well as across the musical barrier. In some embodiments, agents delivered using the glycosphingolipid described herein exhibit longer half-life, compared to agents delivered alone. Methods of delivering a therapeutic agent to a subject for treating a disease using the glycosphingolipid delivery vehicle are also provided.

20 Claims, 31 Drawing Sheets

(56) References Cited

OTHER PUBLICATIONS

Augé et al., The sphingomyelin-ceramide signaling pathway is involved in oxidized low density lipoprotein-induced cell proliferation. J Biol Chem. Aug. 9, 1996;271(32):19251-5. doi: 10.1074/jbc.271.32.19251.
Backhed et al., Host-bacterial mutualism in the human intestine. Science. Mar. 25, 2005;307(5717):1915-20.
Bagai et al., Reconstituted Sendai virus envelopes as biological carriers: dual role of F protein in binding and fusion with liver cells. Biochim Biophys Acta. Oct. 10, 1993;1152(1):15-25.
Ballou et al., Interleukin-1-mediated PGE2 production and sphingomyelin metabolism. Evidence for the regulation of cyclooxygenase gene expression by sphingosine and ceramide. J Biol Chem. Oct. 5, 1992;267(28):20044-50.
Brocca et al., Conformation of the oligosaccharide chain of G(M1) ganglioside in a carbohydrate-enriched surface. Biophys J. Jan. 1998;74(1):309-18. doi: 10.1016/S0006-3495(98)77788-4.
Brown, Lipid rafts, detergent-resistant membranes, and raft targeting signals. Physiology (Bethesda). Dec. 2006;21:430-9.
Chigorno et al., Formation of a cytosolic ganglioside-protein complex following administration of photoreactive ganglioside GM1 to human fibroblasts in culture. FEBS Lett. Apr. 24, 1990;263(2):329-31.
Chiricozzi et al., GM1 Ganglioside Is A Key Factor in Maintaining the Mammalian Neuronal Functions Avoiding Neurodegeneration. Int J Mol Sci. Jan. 29, 2020;21(3):868. doi: 10.3390/ijms21030868.
Dickinson et al., Bidirectional FcRn-dependent IgG transport in a polarized human intestinal epithelial cell line. J Clin Invest. Oct. 1999;104(7):903-11.
Dickinson et al., Ca2+–dependent calmodulin binding to FcRn affects immunoglobulin G transport in the transcytotic pathway. Mol Biol Cell. Jan. 2008;19(1):414-23. Epub Nov. 14, 2007.
Dobrowsky et al., Ceramide activates heterotrimeric protein phosphatase 2A. J Biol Chem. Jul. 25, 1993;268(21):15523-30.
Doyle et al., Glucagon-like peptide-1. Recent Prog Horm Res. 2001;56:377-99.
Franchini et al., Synthesis of a fluorescent sulfatide for the study of CD1 antigen binding properties. Eur J Org Chem. Dec. 2004;2004(23):4755-61.
Gao et al. Potentiation of Cationic Liposome-Meidated Gene Delivery by Polycations. Biochemistry 1996, 35, 1027-1036. (Year: 1996).
Gidwani et al., Disruption of lipid order by short-chain ceramides correlates with inhibition of phospholipase D and downstream signaling by FcepsilonRI. J Cell Sci. Aug. 1, 2003;116(Pt 15):3177-87. doi: 10.1242/jcs.00621.
Gudz et al., Direct inhibition of mitochondrial respiratory chain complex III by cell-permeable ceramide. J Biol Chem. Sep. 26, 1997;272(39):24154-8. doi: 10.1074/jbc.272.39.24154.
Hanna et al., A novel pathway for tumor necrosis factor-alpha and ceramide signaling involving sequential activation of tyrosine kinase, p21(ras), and phosphatidylinositol 3-kinase. J Biol Chem. Apr. 30, 1999;274(18):12722-9. doi: 10.1074/jbc.274.18.12722.
Holowka et al., Short chain ceramides disrupt immunoreceptor signaling by inhibiting segregation of Lo from Ld Plasma membrane components. Biol Open. Sep. 27, 2018;7(9):bio034702. doi: 10.1242/bio.034702.
Hsu et al., Ceramide inhibits lipopolysaccharide-mediated nitric oxide synthase and cyclooxygenase-2 induction in macrophages: effects on protein kinases and transcription factors. J Immunol. May 1, 2001;166(9):5388-97. doi: 10.4049/jimmunol.166.9.5388.
Khazanov et al., Physicochemical and biological characterization of ceramide-containing liposomes: paving the way to ceramide therapeutic application. Langmuir. Jun. 1, 2008;24(13):6965-80. doi: 10.1021/la800207z. Epub May 30, 2008.
Kieffer et al., The glucagon-like peptides. Endocr Rev. Dec. 1999;20(6):876-913.

Kolesnick et al., Compartmentalization of ceramide signaling: physical foundations and biological effects. J Cell Physiol. Sep. 2000;184(3):285-300. doi: 10.1002/1097-4652(200009) 184:3<285::AID-JCP2>3.0.CO;2-3.
Kondo et al., Control of ceramide-induced apoptosis by IGF-1: involvement of PI-3 kinase, caspase-3 and catalase. Cell Death Differ. Jun. 2002;9(6):682-92. doi: 10.1038/sj.cdd.4401019.
Ledeen et al., The multi-tasked life of GM1 ganglioside, a true factotum of nature. Trends Biochem Sci. Jul. 2015;40(7):407-18. doi: 10.1016/j.tibs.2015.04.005. Epub May 26, 2015.
Lencer et al., The intracellular voyage of cholera toxin: going retro. Trends Biochem Sci. Dec. 2003;28(12):639-45.
Lencer et al., Transcytosis of cholera toxin subunits across model human intestinal epithelia. Proc Natl Acad Sci U S A. Oct. 24, 1995;92(22):10094-8.
Liu et al., Trifluoromethyl Derivatization of the Ganglioside, GM1. Synthesis. 2010;11:1905-1908. doi: 10.1055/s-0029-1218777.
Lowthers et al., Differential sensitivity to short-chain ceramide analogues of human intestinal carcinoma cells grown in tumor spheroids versus monolayer culture. In Vitro Cell Dev Biol Anim. Sep.-Oct. 2003;39(8-9):340-2. doi: 10.1290/1543-706X (2003)039<0340:DSTSCA>2.0.CO;2.
Makiyama et al., Newly synthetic ceramide-1-phosphate analogs; their uptake, intracellular localization, and roles as an inhibitor of cytosolic phospholipase A(2)α and inducer of cell toxicity. Biochem Pharmacol. Nov. 1, 2010;80(9):1396-406. doi: 10.1016/j.bcp.2010.07.028. Epub Aug. 3, 2010.
Maxfield et al., Endocytic recycling. Nat Rev Mol Cell Biol. Feb. 2004;5(2):121-32.
Mukherjee et al., Endocytic sorting of lipid analogues differing solely in the chemistry of their hydrophobic tails. J Cell Biol. Mar. 22, 1999;144(6): 1271-84.
Mukherjee et al., Role of membrane organization and membrane domains in endocytic lipid trafficking. Traffic. Mar. 2000;1(3):203-11.
Obeid et al., Programmed cell death induced by ceramide. Science. Mar. 19, 1993;259(5102):1769-71. doi: 10.1126/science.8456305.
Okazaki et al., Role of ceramide as a lipid mediator of 1 alpha,25-dihydroxyvitamin D3-induced HL-60 cell differentiation. J Biol Chem. Sep. 15, 1990;265(26):15823-31.
Orskov et al., Biological effects and metabolic rates of glucagonlike peptide-1 7-36 amide and glucagonlike peptide-1 7-37 in healthy subjects are indistinguishable. Diabetes. May 1993;42(5):658-61.
Panasiewicz et al., Preparation of Alexa Fluor 350-conjugated nonradioactive or 3H-labeled GM1 ganglioside derivatives with different ceramides. Anal Biochem. Feb. 1, 2009;385(1):168-70. Epub Oct. 21, 2008.
Pohl et al., Rapid transmembrane diffusion of ceramide and dihydroceramide spin- labelled analogues in the liquid ordered phase. Mol Membr Biol. Apr. 2009;26(3):194-204.
Polyakova et al., New GM1 Ganglioside Derivatives for Selective Single and Double Labelling of the Natural Glycosphingolipid Skeleton. Eur. J. Org. Chem. Oct. 2009;2009;30:5162-77. doi: 10.1002/ejoc.200900645. Epub Oct. 6, 2009.
Rakoff-Nahoum et al., Innate immune recognition of the indigenous microbial flora. Mucosal Immunol. Nov. 2008;1 Suppl 1:S10-4. doi: 10.1038/mi.2008.49.
Rockendorf et al., Synthesis of a fluorescent ganglioside GM1 derivative and screening of a synthetic peptide library fir GM1 binding sequence motifs. Bioconjugate Chemistry. 2003; 18:573-578.
Saslowsky et al., Ganglioside GM1-mediated transcytosis of cholera toxin bypasses the retrograde pathway and depends on the structure of the ceramide domain. J Biol Chem. Sep. 6, 2013;288(36):25804-25809. doi: 10.1074/jbc.M113.474957. Epub Jul. 24, 2013.
Shang et al., Toll-like receptor signaling in small intestinal epithelium promotes B-cell recruitment and IgA production in lamina propria. Gastroenterology. Aug. 2008;135(2):529-38. doi: 10.1053/j.gastro.2008.04.020. Epub Apr. 22, 2008.

(56) References Cited

OTHER PUBLICATIONS

Simon et al.,. Membrane-destabilizing properties of C2-ceramide may be responsible for its ability to inhibit platelet aggregation. Biochemistry. Feb. 17, 1998;37(7):2059-69. doi: 10.1021/bi9710636.

Simons et al., Cholesterol, lipid rafts, and disease. J Clin Invest. Sep. 2002;110(5):597-603.

Simons et al., Model systems, lipid rafts, and cell membranes. Annu Rev Biophys Biomol Struct. 2004;33:269-95.

Sonnino et al., Aggregation properties of semisynthetic GM1 ganglioside (II3Neu5AcGgOse4Cer) containing an acetyl group as acyl moiety. Chem Phys Lipids. Nov. 1990;56(1):49-57. doi: 10.1016/0009-3084(90)90087-8.

Sonnino et al., Preparation of GM1 ganglioside molecular species having homogeneous fatty acid and long chain base moieties. J Lipid Res. Feb. 1985;26(2):248-57.

Sot et al., Molecular associations and surface-active properties of short- and long-N-acyl chain ceramides. Biochim Biophys Acta. Jun. 1, 2005;1711(1):12-9. doi: 10.1016/j.bbamem.2005.02.014. Epub Mar. 16, 2005.

Spiekermann et al., Receptor-mediated immunoglobulin G transport across mucosal barriers in adult life: functional expression of FcRn in the mammalian lung. J Exp Med. Aug. 5, 2002;196(3):303-10.

Stover et al., Liposomal delivery enhances short-chain ceramide-induced apoptosis of breast cancer cells. J Pharmacol Exp Ther. Nov. 2003;307(2):468-75. Epub Sep. 15, 2003.

Sturm et al., Structure-function studies on positions 17, 18, and 21 replacement analogues of glucagon: the importance of charged residues and salt bridges in glucagon biological activity. J Med Chem. Jul. 16, 1998;41(15):2693-700.

Te Welscher et al., Unsaturated glycoceramides as molecular carriers for mucosal drug delivery of GLP-1. J Control Release. Feb. 10, 2014;175:72-8. doi: 10.1016/j.jconrel.2013.12.013. Epub Dec. 23, 2013.

Tsai et al., Protein disulfide isomerase acts as a redox-dependent chaperone to unfold cholera toxin. Cell. Mar. 23, 2001;104(6):937-48.

Van Genderen et al., Differential targeting of glucosylceramide and galactosylceramide analogues after synthesis but not during transcytosis in Madin-Darby canine kidney cells. J Cell Biol. Nov. 1995;131(3):645-54.

Vavrova et al., Synthetic ceramide analogues as skin permeation enhancers: structure-activity relationships. Bioorganic & Medicinal Chemistry. 2003;11:5381-5390.

Xiao et al., Biological activities of glucagon-like peptide-1 analogues in vitro and in vivo. Biochemistry. Mar. 6, 2001;40(9):2860-9.

Zheng et al., Ceramides and other bioactive sphingolipid backbones in health and disease: lipidomic analysis, metabolism and roles in membrane structure, dynamics, signaling and autophagy. Biochim Biophys Acta. Dec. 2006;1758(12):1864-84. doi: 10.1016/j.bbamem.2006.08.009. Epub Aug. 22, 2006.

Zhu et al., C2-ceramide induces cell death and protective autophagy in head and neck squamous cell carcinoma cells. Int J Mol Sci. Feb. 21, 2014;15(2):3336-55. doi: 10.3390/ijms15023336.

Hölttä-Vuori et al., Modulation of cellular cholesterol transport and homeostasis by Rab11. Mol Biol Cell. Sep. 2002;13(9):3107-22. doi: 10.1091/mbc.e02-01-0025.

Möbius et al., Gangliosides are transported from the plasma membrane to intralysosomal membranes as revealed by immuno-electron microscopy. Biosci Rep. Aug. 1999;19(4):307-16. doi: 10.1023/a:1020502525572.

Möbius et al., Intracellular distribution of a biotin-labeled ganglioside, GM1, by immunoelectron microscopy after endocytosis in fibroblasts. J Histochem Cytochem. Aug. 1999;47(8):1005-14. doi: 10.1177/002215549904700804.

Prioni et al., Interactions between gangliosides and proteins in the exoplasmic leaflet of neuronal plasma membranes: a study performed with a tritium-labeled GM1 derivative containing a photoactivable group linked to the oligosaccharide chain. Glycoconj J. 2004;21(8-9):461-70. doi: 10.1007/s10719-004-5536-4.

Sueyoshi et al., Apoptosis of Neuro2a cells induced by lysosphingolipids with naturally occurring stereochemical configurations. J Lipid Res. Aug. 2001;42(8):1197-202.

Vodovozova, Photoaffinity labeling and its application in structural biology. Biochemistry (Mosc). Jan. 2007;72(1):1-20. doi: 10.1134/s0006297907010014.

Welsher et al., Unsaturated glycoceramides as molecular carriers for mucosal drug delivery of GLP-1. J Control Release. Feb. 10, 2014;175:72-8.

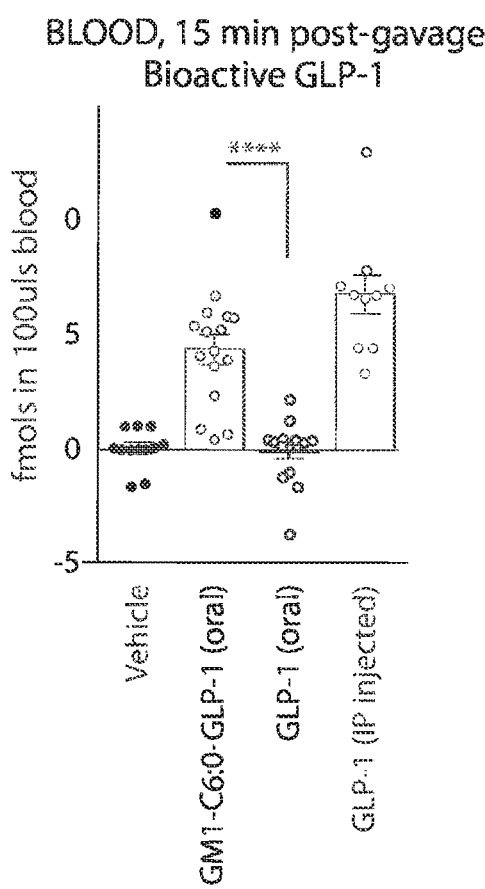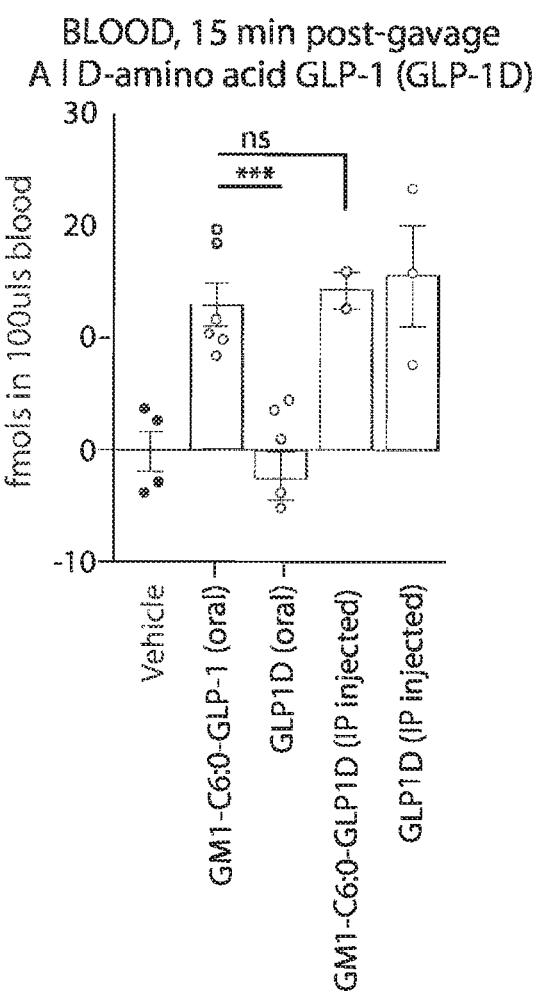
FIG. 5E
FIG. 5F

RGSGYGRGSG – GM1(C12:0)

R = Alexa Fluor®488-
maleimide-cysteine

R = biotinyl-lysine

R = alkyne
(propargyl glycine)

R = biotin+alkyne

SHORT CHAIN CERAMIDE-BASED LIPIDS AND USES THEREOF

RELATED APPLICATIONS

This application is a Divisional of U.S. application Ser. No. 16/759,536, filed Apr. 27, 2020, entitled "SHORT CHAIN CERAMIDE-BASED LIPIDS AND USES THEREOF," which is a National Stage Filing under 35 U.S.C. § 371 of International Application No. PCT/US2018/057787, filed Oct. 26, 2018, entitled "SHORT CHAIN CERAMIDE-BASED LIPIDS AND USES THEREOF," which claims the benefit under 35 U.S.C. § 119 (e) to U.S. Provisional Application No. 62/578,341, filed Oct. 27, 2017, entitled "SHORT CHAIN CERAMIDE-BASED LIPIDS AND USES THEREOF," and U.S. Provisional Application No. 62/643,680, filed Mar. 15, 2018, entitled "SHORT CHAIN CERAMIDE-BASED LIPIDS AND USES THEREOF," the entire contents of each of which are incorporated herein by reference.

This application claims the benefit under 35 U.S.C. § 119(e) to U.S. Provisional Application No. 62/578,341, filed Oct. 27, 2017, entitled "SHORT CHAIN CERAMIDE-BASED LIPIDS AND USES THEREOF," and U.S. Provisional Application No. 62/643,680, filed Mar. 15, 2018, entitled "SHORT CHAIN CERAMIDE-BASED LIPIDS AND USES THEREOF," the entire contents of which are incorporated herein by reference.

FEDERALLY SPONSORED RESEARCH

This invention was made with government support under Grant Numbers DK090603, DK048106, DK104868, DK084424, and DK034854, awarded by the National Institutes of Health. The Government has certain rights in the invention.

BACKGROUND

One of the major challenges for applying protein and peptide biologics to clinical medicine is the lack of rational and efficient methods to circumvent epithelial and endothelial cell barriers separating large molecules from target tissues. In the case of epithelial cells lining mucosal surfaces, the pathway for absorption of large solutes is by transcytosis—a process of transcellular endosome trafficking that connects one surface of the cell with the other (host with environment). The same is true for transport of protein and peptide cargoes across tight endothelial barriers that separate blood from tissue—typified by the blood-brain barrier.

SUMMARY

Some aspects of the present disclosure provide delivery vehicles comprising a glycosphingolipid and an agent to be delivered, wherein the glycosphingolipid comprises an oligosaccharide, and (a) a ceramide that comprises a short-chain fatty acid (C1-C3), or (b) a ceramide that does not contain a fatty acid, and wherein the agent to be delivered is attached to the oligosaccharide of the glycosphingolipid.

In some embodiments, the glycosphingolipid is a ganglioside. In some embodiments, the ganglioside comprises a sialic acid. In some embodiments, the ganglioside is monosialotetrahexosylganglioside (GM1). In some embodiments, the ganglioside is monosialodihexosylganglioside (GM3).

In some embodiments, the glycosphingolipid is a globoside. In some embodiments, the globoside is globotriaosyl ceramide (Gb3).

In some embodiments, the glycosphingolipid is a cerebroside. In some embodiments, the cerebroside is a glucocerebroside, a galactocerebroside, or a lactocerebroside. In some embodiments, the cerebroside is a sulfatide.

In some embodiments, the ceramide comprises a short-chain fatty acid (C1-C3) with no double bonds between carbon atoms. In some embodiments, the ceramide comprises a C2 fatty acid chain with a double bond between carbon atoms. In some embodiments, the ceramide comprises a C3 fatty acid chain with at least one double bond between carbon atoms. In some embodiments, the ceramide does not comprise a fatty acid.

In some embodiments, the agent to be delivered is selected from the group consisting of proteins, peptides, nucleic acids, polysaccharides and carbohydrates, lipids, glycoproteins, small molecules, synthetic organic and inorganic drugs exerting a biological effect when administered to a subject, and combinations thereof.

In some embodiments, the agent to be delivered is a therapeutic agent. In some embodiments, the therapeutic agent is an anti-inflammatory agent, a vaccine antigen, an anti-cancer drug or chemotherapeutic drug, a clotting factor, a hormone, a steroid, a cytokine, an antibiotic, an antibody, a vaccine adjuvant, or a drug for the treatment of cardiovascular disease, an infectious disease, an autoimmune disease, allergy, a blood disorder, a metabolic disorder or a skin disease.

In some embodiments, the agent to be delivered is a protein or a peptide. In some embodiments, the protein or peptide is a vaccine antigen. In some embodiments, the protein or peptide is an antibody. In some embodiments, the protein or peptide is an enzyme. In some embodiments, the protein or peptide is GLP-1, or a functional fragment thereof. In some embodiments, the protein or peptide is Exendin-4, or a functional fragment thereof.

Other aspects of the present disclosure provide glycosphingolipid-therapeutic agent complexes comprising a glycosphingolipid attached to a therapeutic agent, wherein the glycosphingolipid comprises an oligosaccharide, and (a) a ceramide that comprises a short chain fatty acid (C1-C3) or (b) a ceramide that does not contain a fatty acid chain, and wherein the agent to be delivered is attached to the oligosaccharide of the glycosphingolipid.

In some embodiments, the glycosphingolipid is a ganglioside. In some embodiments, the ganglioside comprises a sialic acid. In some embodiments, the ganglioside is monosialotetrahexosylganglioside (GM1). In some embodiments, the ganglioside is monosialodihexosylganglioside (GM3).

In some embodiments, the glycosphingolipid is a globoside. In some embodiments, the globoside is globotriaosyl ceramide (Gb3).

In some embodiments, the glycosphingolipid is a cerebroside. In some embodiments, the cerebroside is a glucocerebroside, a galactocerebroside, or a lactocerebroside. In some embodiments, the cerebroside is a sulfatide.

In some embodiments, the ceramide comprises a short-chain fatty acid (C1-C3) with no double bonds between carbon atoms. In some embodiments, the ceramide comprises a C2 fatty acid chain with a double bond between carbon atoms. In some embodiments, the ceramide comprises a C3 fatty acid chain with at least one double bond between carbon atoms. In some embodiments, the ceramide does not comprise a fatty acid.

In some embodiments, the therapeutic agent is selected from the group consisting of proteins, peptides, nucleic acids, polysaccharides and carbohydrates, lipids, glycoproteins, small molecules, synthetic organic and inorganic drugs exerting a biological effect when administered to a subject, and combinations thereof.

In some embodiments, the therapeutic agent is an anti-inflammatory agent, a vaccine antigen, an anti-cancer drug or chemotherapeutic drug, a clotting factor, a hormone, a steroid, a cytokine, an antibiotic, an antibody, a vaccine adjuvant, or a drug for the treatment of cardiovascular disease, an infectious disease, an autoimmune disease, allergy, a blood disorder, a metabolic disorder or a skin disease.

In some embodiments, the therapeutic agent is a protein or a peptide. In some embodiments, the protein or peptide is a vaccine antigen. In some embodiments, the protein or peptide is an antibody. In some embodiments, the protein or peptide is an enzyme. In some embodiments, the protein or peptide is GLP-1, or a functional fragment thereof. In some embodiments, the protein or peptide is Exendin-4, or a functional fragment thereof.

Other aspects of the present disclosure provide glycosphingolipid-therapeutic agent complexes comprising a monosialotetrahexosylganglioside (GM1) attached to a therapeutic agent, wherein the GM1 comprises an oligosaccharide, and (a) a ceramide that comprises a short chain fatty acid (C1-C3); or (b) a ceramide that does not contain a fatty acid chain, and wherein the therapeutic agent is attached to the oligosaccharide of the GM1.

Compositions comprising the delivery vehicles or the glycosphingolipid-therapeutic agent complex described herein are provided. In some embodiments, the composition comprises a pharmaceutically acceptable earlier.

Other aspects of the present disclosure provide methods of delivering an agent into a cell or across a mucosal surface, the method comprising contacting the delivery vehicle described herein with the cell or the mucosal surface, under conditions appropriate for uptake of the delivery vehicle or the agent into the cell or absorption of the delivery vehicle or the agent across the mucosal surface.

Other aspects of the present disclosure provide method of delivering an agent into a cell or across a mucosal surface, the method comprising contacting the glycosphingolipid-therapeutic complex described herein, with the cell or the mucosal surface, under conditions appropriate for uptake of the glycosphingolipid-therapeutic agent complex or the agent into the cell or absorption of the glycosphingolipid-therapeutic agent complex or the agent across the mucosal surface.

Other aspects of the present disclosure provide methods of delivering an agent into a cell or across a mucosal surface, the method comprising contacting the composition described herein, with the cell or the mucosal surface, under conditions appropriate for uptake of the composition or the agent into the cell or absorption of the composition or the agent across the mucosal surface.

Other aspect of the present disclosure provide methods of delivering an agent into a cells or across a mucosal surface in a subject, the method comprising administering to the subject a delivery vehicle described herein, the glycosphingolipid-therapeutic agent complex described herein, or the composition described herein.

Methods of enhancing the half-life of an agent in a subject are provided, the method comprising administering to the subject a delivery vehicle, the glycosphingolipid-therapeutic agent complex, or the composition described herein.

Methods treating a disease or condition in a subject in need thereof are provided, the method comprising administering to the subject a delivery vehicle, the glycosphingolipid-therapeutic agent complex, or the composition described herein.

Methods of treating a disease or condition in a subject in need thereof are provided, the method comprising administering to the subject an effective amount of a delivery vehicle, the glycosphingolipid-therapeutic agent complex, or the composition described herein.

In some embodiments, the delivery vehicle, the glycosphingolipid-therapeutic agent complex, or the composition is administered parenterally. In some embodiments, the delivery vehicle, the glycosphingolipid-therapeutic agent complex, or the composition is administered nonparenterally or subcutaneously.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 1A) Representative structure of GM1 sphingolipids fused to an all-D amino acid reporter peptide. The reporter peptide contains a lysine-linked biotin used for affinity purification and an N-terminal Alexa Fluor 488. (FIG. 18) GM1-peptide fusions or unfused reporter peptide were added apically to MDCK-II cells grown on filter supports and imaged by live cell confocal microscopy. Transcytosis of the C12:0-GM1-reporter peptide fusion (with either a C18:1 or C20:1 sphingosine) is evident by basolateral membrane fluorescence. The C16:0-GM1 reporter molecule is delivered to intracellular puncta, presumably lysosomes. Scale bars 10 µm. (FIG. 1C) Transport of the indicated GM1-reporter peptide fusions across T84 cell monolayers with the indicated fatty acid chain length and degree of saturation. The GM1-peptide fusions containing ceramide domains with short fatty acids have a ~10-fold increase in trans-epithelial transport over the unfused reporter peptide. (FIG. 1D) Transepithelial transport of the C6:0-GM1 peptide fusion across T84 monolayers is dose-dependent and far exceeds transport of the unconjugated reporter peptide. (FIG. 1E) T84monolayers were simultaneously treated with unfused peptide and unfused C6:0-GM1. Mixing experiments confirm that fusion of the reporter peptide to the glycosphingolipid carrier is required for amplified transcellular transport.

(FIG. 2A) Transport of C6:0 and C12:0 GM1-peptide fusions across T84 cell monolayers reported as apparent permeability (PAPP) shows that minimal transport occurs during a 4° C. temperature block. (FIG. 28) Analysis of MDCK-II monolayers loaded with 0.5 µM C6:0-GM1 peptide fusion in the absence (left and middle panels) or presence (right panel) of 2 mM EDTA. Live cell confocal imaging shows minimal transport occurs during a 10° C. temperature block (middle panel) consistent with transcellular transport by membrane trafficking and minimal paracellular leak. In the presence of disrupted tight junctions (i.e. in the presence of EDTA, right panel) basolateral membranes are stained by paracellular passive diffusion (transceilular leak). (FIG. 2C) Transcytosis across MDCK-II monolayers is blocked by dynamin inhibition of endocytosis (50 µM Dyngo-4A). In Dyngo-4A treated cells (gray bars), there is a significant decrease in transepithelial transport of both C6:0 (n=8) and C12:0 (n=8) GM1-peptide fusions but not the unfused reporter peptide (n=6). (FIG. 2D) Transcellular transport of the C6:0-GM1 peptide fusion (n=6) or unfused reporter peptide (n=5) in cell monolayers depleted of the exocyst complex by esiRNA transfection against EXO2 (gray bars). (mean±s.e.m) (ns=non-significant, p<0.01, **p<0.0001; Bonferroni's multiple comparison test).

(FIG. 3A) Live cell confocal images of MDCK-II cell monolayers after a 10 minute pulse and 3 hour chase with 0.5 µM reporter peptide, C6:0 or C12:0-GM1 peptide fusion. Images are taken at the plane of apical membranes (left column) or midway through cell body (right column). (FIGS. 3B-3C) Time courses of diffusion from MDCK cell membranes to media (B) or media containing defatted-BSA (C) of C2:0 (n=5), C6:0 (n=8), C12:0 (n=12) GM1-peptide fusions and C12:0-GM3-peptide fusion (n=9). (FIG. 3D) The C12:0-GM3 peptide fusion has enhanced transepithelial transport compared to the C12:0-GM1-peptide fusion and is dynamin dependent (n=4). (FIG. 3E) The rate of membrane release of the C12:0-GM1-peptide molecule is enhanced in the presence of 100 mM lactose, but not 100 mM mannitol implicating a galactose-specific lectin membrane anchor (n=10) (mean±s.e.m.).

(FIG. 4A) in vivo studies showing absorption across intestinal epithelial barriers into blood after gastric administration of indicated GM1 peptide fusions, vehicle alone, or unfused reporter peptide (5 independent experiments). (FIG. 4B) Absorption across the intestine into blood 15 minutes after gastric administration of the C12:0-GM3, C6:0-GM1 peptide fusions or peptide (n=2). (FIG. 4C) 1 hour after gastric gavage the C4:0-GM1 peptide fusion is absorbed to the liver whereas the unfused reporter peptide is not detected (4 independent experiments). (FIG. 4D) Uptake into nasal epithelium; After topical nasal administration, tissue was fixed with 4% formaldehyde and stained with anti-EpCAM to label epithelium and DAPI for nuclei. Images by two-photon microscopy comparing transport of the unfused reporter peptide (left panels) and C6:0-GM1 peptide fusion (right panels) Scale bars 20 um upper panel, 10 um lower panels. (FIG. 4E) Biochemical analysis of blood 30 minutes after nasal administration shows systemic absorption of C6:0 and C12:0-GM1 peptide fusions (2 independent experiments). Each data point on each graph represents individual mice and bars represent mean±s.e.m. (ns=non-significant, *p<0.5; ***p<0.0001, Tukey's multiple comparison test).

FIGS. 5A to 5F. GM1-mediated absorption of GLP-1 affects blood glucose metabolism. (FIG. 5A) GLP-1 and all-D GLP-1 isomer sequence used for coupling to a C6:0 and C2:0 GM1 ceramide species. (FIG. 5B) In vitro transcytosis assay with C6:0-GM1-GLP-1, or unfused GLP-1 across T84 cell monolayers (3 independent experiments) (Unpaired t-test, *p<0.5). (FIG. 5C) Representative intraperitoneal glucose tolerance test after gastric gavage of 10 nmol/kg C6:0-GM1-GLP-1. Each point represents mean±s.e.m (n=4 mice). Mice fed C6:0-GM1-GLP-1 show faster recovery after a glucose challenge in contrast to mice gavaged with unfused GLP-1 or vehicle. (FIG. 5D) Effect of the indicated GM1-GLP-1 species, GLP-1 alone, or vehicle on glucose tolerance quantified as Area under Curve (AUC) for 8 independent experiments with each data point representing individual mice and bar representing the mean±s.e.m. (FIG. 5E) GLP-1 in blood 15 minutes after gastric gavage quantified for each species using the luciferase bioassay (fmols of compound per 100 uls blood for 4 independent experiments). (FIG. 5F) Systemic absorption of an all D-isomer of GLP-1 used to directly measure the cargo in blood 3 independent experiments). (A-E) Each data point on graphs represents individual mice and bars represent mean±s.e.m. (ns=non-significant, *p<0.5; ***p<0.0001, Tukey's multiple comparison test).

(FIG. 6A) HPLC and mass spectrometry of purified C12:0-GM1-peptide fusion. Compounds shows high purity with resolution to separate fusions containing C18:1 and C20:1 sphingosine isomers of the original lipids and the correct mass. (FIG. 6B) Functional groups tested individually to validate our GM1-peptide constructs. (FIG. 6C) To test effects of the various functional groups, confocal imaging of MDCK monolayers treated with the reporter peptide or with the different lipid fusions was performed. Scale bars 10 µm After incubation with the indicated molecule, monolayers were treated with fluorescently labeled cholera toxin B-subunit and examined for fluorescence at basolateral membranes. In all cases, the C12:0-GM1 fusion is sorted into the recycling and transcytotic pathway. (FIG. 6D) GM1-C6:0 and GM1-C12:0-peptide fusions are sorted to the recycling endosome as measured by co-localization with the transferrin receptor (bottom panels) and away from the lysosome as measured by lysotracker (top panels).

(FIG. 7A) Schematic representation of our transcytosis assay. GM1-peptide fusions containing a biotin (smallcircle) and fluorophore (star) are affinity isolated from basolateral media by addition of streptavidin beads. (FIG. 7B) Standard curve for the transcytosis assay demonstrates our assay is sensitive to picomolar concentrations. (FIG. 7C) Transport of GM1-reporter peptide fusions across T84 cell monolayers with very short chain fatty acids chain. Data shows that GM1-peptide fusions containing ceramide domains with very short fatty acid chains have a 10-fold increase in trans-epithelial transport over the unconjugated reporter peptide. (FIG. 7D) Membrane loading of the different GM1-peptide fusion molecules determined by quantitative fluorescence measurement of cells after trypsin treatment. (FIG. 7E) TEER measurements of T84 cells before treatment (control, grey bars) or after a 3-hour treatment (white bars) with the reporter peptide or C6:0-GM1 peptide fusion. (FIG. 7F) MTT assay after a 3 hour treatment with the C6:0 or C12:0-GM1 peptide fusion shows no effect on cell viability at a wide range of doses. (FIG. 7G) Permeability assay in MDCK monolayers treated simultaneously with 1 mg/mL AlexaFlour-594 conjugated Dextran and the indicated GM1-peptide fusion. Cumulative amount of Dextran AlexaFlour-594 (MW=10 kDa) transported from the apical to the basolateral compartment over 3 hours is not affected by addition of GM1-peptide fusions. Results are summarized as the mean±s.e.m of a representative experiment.

(FIG. 8A) Live cell confocal images of MDCK cell monolayers after a 10 minute pulse and 10 minute hour chase with 0.5 µM C6:0 or C12:0-GM1 peptide fusion. Images are taken at level of basolateral membranes. (FIG. 8B) The C6:0-GM3 peptide fusion shows enhanced transepithelial transport compared to the C6:0-GM1-peptide fusion (n=2). (FIGS. 8D and 8D) Time course of diffusion from MDCK cell membranes to solution for C12:0-GM1 and C12:0-GM3 peptide fusions in the presence of 5 mM lactose. The rate of membrane release of the C12:0-GM1-peptide molecule is enhanced in the presence of 5 mM lactose (n=4) (mean±s.e.m). In contrast, the rate of diffusion from cell membranes to solution for the C12:0-GM3 peptide fusion is not affected by treatment with 5 mM lactose (n=4) (mean s.e.m). (FIGS. 8E-8F) In the presence of 5 mM N-acetyl-galactosamine-galactose (GalNAc), the GM1-peptide fusion molecule shows a faster rate of diffusion from cell membranes to solution (n=6) (mean±s.e.m). Treatment with 5 mM GalNAc had no effect on the rate of diffusion for the GM3-peptide fusion molecule (n=6) (mean±s.e.m).

(FIG. 9A) Representative luciferase assay confirming enzymatic activity of our C6:0-GM1-GLP-1 fusion compared to unfused GLP-1 and commercially available Exendin-4. (FIG. 9B) In vivo study showing absorption across intestinal epithelial bathers into blood after oral administration of the C6:0 and C4:0-GM1 peptide fusion compared to vehicle and the unfused reporter peptide. In contrast, the C2:0-GM1-peptide fusion is not absorbed.

(FIG. 10A) Transport of reporter peptide across intestinal epithelial T84 cells of different GM1 fatty acid species, where C2:0 is equivalent, or possibly better than other candidates. (FIG. 10B) Bioassay used in HEK cells tests the relative activity of GM1-fused GLP1 constructs for the GLP1-receptor. C2:0-GLP1 shown versus control unfused GLP1. (FIG. 10C) Transport of therapeutic GLP1-peptide fused to C2:0 GM1 across a polarized epithelial MDCK barrier.

(FIG. 11A) Representative luciferase assay confirming enzymatic activity of our C6:0-GM1-GLP-1 fusion compared to unfused GLP-1 and commercially available Exendin-4. (FIG. 11B) In vivo study showing absorption across intestinal epithelial bathers into blood after oral administration of the C6:0 and C4:0-GM1 peptide fusion compared to vehicle and the unfused reporter peptide. In contrast, the C2:0-GM1-peptide fusion was not absorbed.

DETAILED DESCRIPTION OF CERTAIN EMBODIMENTS

Figure 1A:
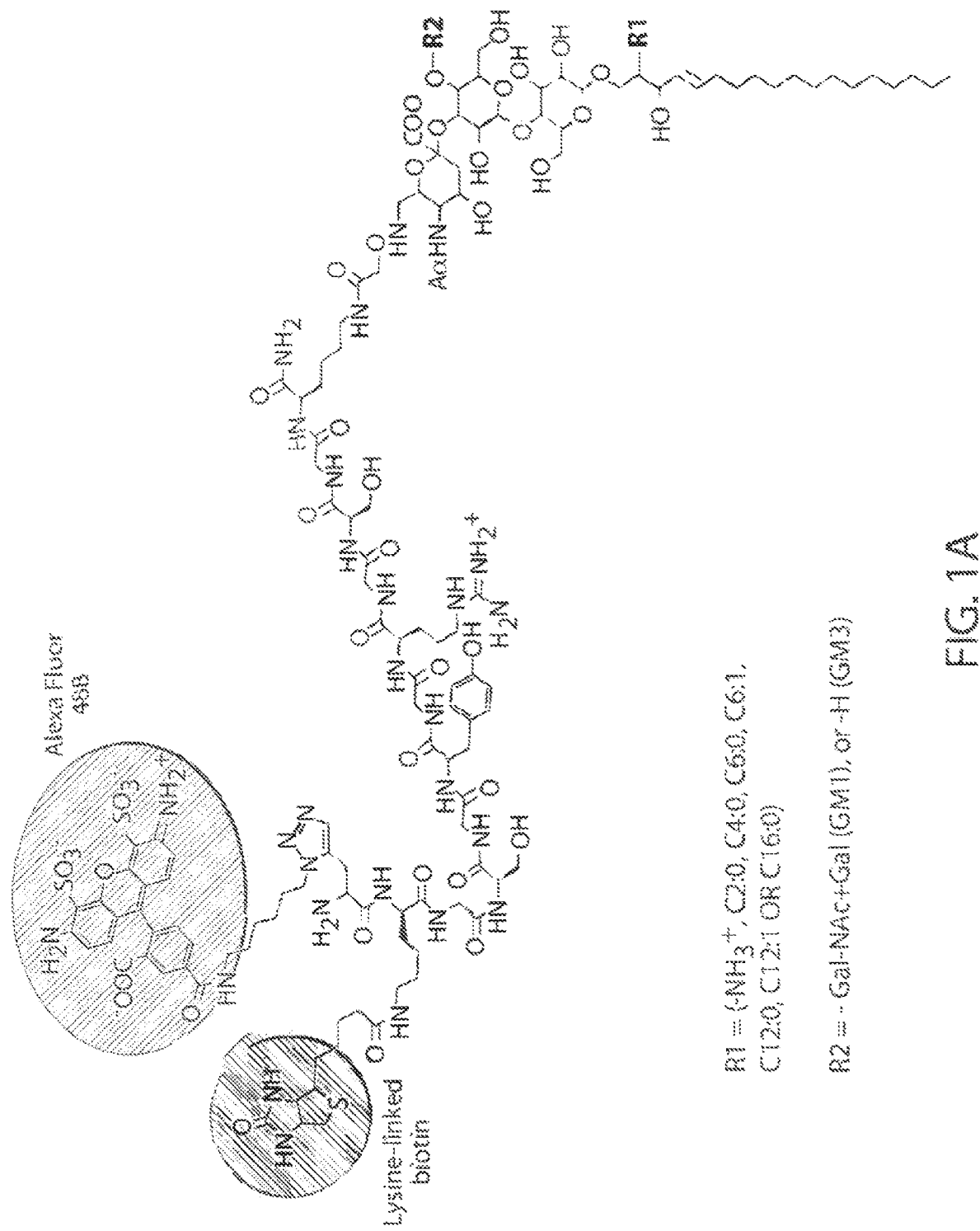
FIGS. 1A to 1E. Modifications to the ceramide domain of GM1 results in enhanced trans-epithelial transport.

Delivery of biologically active molecules across tight mucosal epithelial barriers is a major challenge preventing application of most therapeutic peptides for oral drug delivery. The present disclosure, in some aspects, provides methods of using short-chain, non-native glycosphingolipids as delivery vehicles. Herein, a set of synthetic glycosphingolipids are identified that harness the endogenous process of intracellular lipid-sorting to enable mucosal absorption of the incretin hormone GLP-1. Peptide cargoes covalently fused to glycosphingolipids with ceramide domains containing C6:0 or smaller fatty acids were transported with 20-100-fold greater efficiency across epithelial barriers in vitro and in vivo. This was explained by structure-function of the ceramide domain in intracellular sorting and by the affinity of the glycosphingolipid species for insertion into and retention in cell membranes. In vivo, GLP-1 fused to short-chain glycosphingolipids was rapidly and systemically absorbed after gastric gavage to affect glucose tolerance with serum bioavailability comparable to intraperitoneal injection of GLP-1 alone. This is unprecedented for mucosal absorption of biologics, and defines a technology with many other clinical applications.

Glycosphingolipids are present within the outer membrane leaflet of cell membranes. They contain a ligand-binding oligosaccharide domain that faces the extracellular space, and a ceramide domain that anchors the lipid in the membrane bilayer. Ceramides consist of a sphingosine chain (typically C18:1 or C20:1) coupled to a fatty acid that can have diverse structures. The oligosaccharide domain prevents lipid flip-flop between membrane leaflets, causing all the glycosphingolipids to be distributed among intracellular compartments only by vesicular trafficking. Sorting of proteins and certain sphingolipids to various intracellular compartments of eukaryotic cells depends on movement of membranes through the secretory and endocytic pathways by vesicular carriers. For proteins, this occurs according to multiple and hierarchically ordered sorting determinants structurally encoded within the protein itself or within the structure of an associated receptor or chaperone.

Methods of using glycosphingolipids isoforms containing a ceramide that comprises fatty acids of different structures (e.g., long or short fatty acid chain, with or without double bonds) to deliver an agent (e.g., a therapeutic agent) into a cell or across a mucosal barrier have been described (e.g., in U.S. Pat. No. 9,457,097, incorporated herein by reference).

The present disclosure is based, at least in part, on the unexpected finding that glycosphingolipids containing a ceramide with a fatty acid chain of C3 or less can be used to deliver an agent (e.g., a therapeutic agent) into a cell or across a mucosal barrier, without causing cellular toxicity. It is unexpected because it is known in the art that ceramides with a fatty acid chain that is shorter than C4 (e.g., C3, C2, C1, or C0) have cellular toxicity (e.g., as described in Sueyoshi et al., Journal of Lipid Research, Volume 42, 11974202, 2001, incorporated herein by reference), and are not expected to be able to direct intracellular trafficking of associated agents.

Accordingly, some aspects of the present disclosure relate to delivery vehicles comprising a glycosphingolipid and an agent to be delivered, wherein the glycosphingolipid comprises an oligosaccharide, and (a) a ceramide that comprises a short-chain fatty acid (C1-C3) or (b) a ceramide that does not contain a fatty acid (also termed lyso-ceramide or sphingosine herein), and wherein the agent to be delivered is attached to the oligosaccharide of the glycosphingolipid.

A "delivery vehicle" refers to a molecule or system that delivers an agent (e.g., a therapeutic agent) to a desired location, e.g., without limitation, to enter a cell or to reach a desired cellular compartment (e.g., the endoplasmic reticulum), to reach a desired part in a subject (e.g., an organ), or to reach a diseased site in a subject (e.g., a tumor site). In some embodiments, the delivery vehicle includes the agent to be delivered. In some embodiments, the delivery vehicle is associated with (or attached to) the agent to be delivered. In these situations, complexes comprising the delivery vehicle and the agent to be delivered are formed and termed herein a "glycosphingolipid-agent complex." In some embodiments, the agent is a therapeutic agent and the complex comprising the delivery vehicle and the therapeutic agent is herein termed a "glycosphingolipid-therapeutic agent complex."

A "glycosphingolipid" is a subtype of glycolipids containing an amino alcohol sphingosine. A glycosphingolipid may be considered as a sphingolipid with an oligosaccharide attached. Non-limiting examples of glycosphingolipids that may be used in accordance with the present disclosure include gangliosides, cerebrosides and globosides.

A "sphingolipid" belongs to a class of lipids containing a backbone of sphingoid bases and a set of aliphatic amino alcohols. Sphingolipids generally are composed of a long-chain (sphingoid) base (sphingosine, sphinganine, 4-hydroxysphinganine, or a related compound) as the backbone moiety (Karlsson et al., Chem. Phys. Lipids, 5:6-43, 1970, incorporated herein by reference), which is usually modified by an amide-linked long-chain fatty acid (for ceramides), and a head group at position 1. Over 300 classes of sphingolipids are known, most of which have head groups with simple to complex carbohydrates (e.g., as described in Merrill et al., New Comprehensive Biochemistry: Biochemistry of Lipids, Lipoproteins, and Membranes, pp. 309-338, Elsevier Science, Amsterdam, 1996, incorporated herein by reference). Sphingolipids are major constituents of all eukaryotic (and some prokaryotic) organisms, including plants (e.g., as described in Lynch et al., Lipid Metabolism in Plants, pp. 285-308, CRC Press, Boca Raton, Fla. 1993, incorporated herein by reference). In some embodiments, the sphingolipid is a ceramide.

In some embodiments, the glycosphingolipid of the present disclosure is a ganglioside. A "ganglioside" is a molecule composed of a sphingolipid (e.g., a ceramide) with one or more sialic acids (e.g., n-acetylneuraminic acid, NANA) linked on the oligosaccharide chain. Ganglioside is a component of the cell plasma membrane that modulates cell signal transduction events, and appears to concentrate in lipid rafts. In some embodiments, the ganglioside comprises one sialic acid. In some embodiments, the ganglioside comprises more than one sialic acids (e.g., 2, 3, 4, 5, or more). More than 60 gangliosides are known, which differ from each other mainly in the position and number of NANA residues.

In some embodiments, the ganglioside comprises one sialic acid. Exemplary gangliosides that contain a sialic acid include, without limitation: monosialotetrahexosylganglioside (GM1) and monosialodihexosyiganglioside (GM3). The letter G refers to ganglioside, and M is for monosialic acid as GM1 or GM3 has one sialic acid only. The numbering is based on its relative mobility in electrophoresis among other monosialic gangliosides. The structure of gangliosides containing sialic acid can be condensed to NANA-Gal-Glc-ceramide. GM1 has important physiological properties and impacts neuronal plasticity and repair mechanisms, and the release of neurotrophins in the brain. GM3 has been indicated to be associated with Parkinson's disease (e.g., in Chan et al., PLeS One. 2017 Feb. 17; 12(2):e0172348, incorporated herein by reference).

Non-limiting examples of gangliosides that may be used in accordance with the present disclosure include GM2-1, GM3, GM2,GM2a, GM2b, GM1, GM1a, GA1, GM1b, GD3, GD2, GD1a, GD1alpha, GD1b, GT1a, GT1, GT1b, OAc-GT1b, GT1c, GT3, GQ1b, and GGa1.

In some embodiments, the glycosphingolipid of the present disclosure is a globoside. A "globoside" is a type of glycosphingolipid with more than one oligosaccharide as the side chain (or R group) of ceramide. The oligosaccharide s are usually a combination of N-acetylgalactosamine, D-glucose or D-galactose. In some embodiments, the globoside is globotriaosylceramide (Gb3). A "globotriaosylceramide (Gb3)" is also termed a "ceramide trihexoside" and is formed by an alpha linkage of galactose to lactosylceramide.

In some embodiments, the glycosphingolipid of the present disclosure is a cerebroside. A "cerebroside" is a monoglycosylceramide that is an important components in animal muscle and nerve cell membranes. A cerebroside consists of a ceramide with a single sugar residue at the 1-hydroxyl moiety. Exemplary cerebrosides include, without limitation, glucocerebrosides, galactocerebrosides, and lactocerebrosides.

In some embodiments, the cerebroside is a sulfatide. A "sulfatide" refers to a class of sulfolipids, specifically a class of sulfoglycolipids, which are glycolipids that contain a sulfate group. Sulfatide is synthesized primarily starting in the endoplasmic reticulum and ending in the Golgi apparatus where ceramide is converted to galactocerebroside and later sulfated to make sulfatide. Of all of the galactolipids that are found in the myelin sheath, one fifth of them are sulfatide. Sulfatide is primarily found on the extracellular leaflet of the myelin plasma membrane produced by the oligodendrocytes in the central nervous system and in the Schwann cells in the peripheral nervous system. However, sulfatide is also present on the extracellular leaflet of the plasma membrane of many cells in eukaryotic organisms.

A "ceramide" is a sphingolipid composed of sphingosine and a fatty acid. A sphingosine is an amino alcohol with an unsaturated hydrocarbon chain that is typically 18-carbon or 20-carbon in length, which forms a primary part of sphingolipids (e.g., ceramides). The fatty acid of a ceramide can have diverse structures. For example, the fatty acid chain may be 0 (no fatty acid) to 30 carbons (e.g., 0, 1, 3, 4, 5, 6, 7, 8, 9, 10, 11, 12, 13, 14, 15, 16, 17, 18, 19, 20, 21, 22, 23, 24, 25, 26, 27, 28, 29, or 30) in length. In some instances, the fatty acid change may contain one or more cis-double bonds. A "cis-double bond," as used herein refers to an isoform of a double bond formed between two carbon atoms. In addition to the double bond, other chemical groups (e.g., —H, —CH3, —COOH) also form bonds with the carbon atom involved in the cis-double bond, and "cis" indicates that the chemical groups other than —H are on the same side of the carbon chain. One skilled in the art is familiar with these terms.

The ceramides of the present disclosure contain a fatty acid chain that is 0 to 3-carbon in length, without a double bond, or with one or two double bonds, and are termed "short-chain ceramides." Each of these fatty acids are termed herein as following: 0-carbon fatty acid (no fatty acid, also termed a sphingosine or a lyso-ceramide); 1-carbon fatty acid (C1); 2-carbon fatty acid with no double bond (C2:0), 3-carbon fatty acid with no double bond (C3:0); 2-carbon fatty acid with one double bond (C2:1); 3-carbon fatty acid with one double bond (C3:1); and 3-carbon fatty acid with two double bonds (C3:2). In some embodiments, the glycosphingolipid of the present disclosure is a C2:0-GM1 or a C2:0-GM3, i.e., a GM1 or G3 containing a ceramide with a 2-carbon fatty acid without double bonds, respectively (e.g., as shown in FIG. 1A). In some embodiments, the glycosphingolipid of the present disclosure is lyso-ceramide-GM1, also termed sphingosine-GM1. In some embodiments, the glycosphingolipid of the present disclosure is lyso-ceramide-GM3, also termed sphingosine-GM3.

The glycosphingolipids containing the short-chain ceramides described herein are found to be able to act as delivery vehicles to deliver an agent across cell membrane or across mucosal barrier and direct intracellular trafficking of the agent. For example, in some embodiments, the glycosphingolipid-agent complex may be directed by the glycosphingolipid to a desired intracellular location, e.g., the endoplasmic reticulum (ER). In some embodiments, the glycosphingolipid-agent complex is directed by the glycosphingolipid away from degradative pathways (e.g., lysosome). As such, in some embodiments, the cellular half-life of the agent is prolonged when the agent is part of the glycosphingolipid-agent complex, compared to when the agent is delivered into cells alone. In some embodiments, the cellular half-life of the agent is prolonged by at least 20% when the agent is part of the glycosphingolipid-agent complex, compared to when the agent is delivered into cells alone. In some embodiments, the cellular half-life of the agent is prolonged by at least 20%, at least 30%, at least 40%, at least 50%, at least 60%, at least 70%, at least 80%, at least 90%, at least 100%, at least 2 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold, at least 500 fold, at least 1000 fold or more, when the agent is part of the glycosphingolipid-agent complex, compared to when the agent is delivered into cells alone. In some embodiments, the cellular half-life of the agent is prolonged by 20%, 30%, 40%, 50%, 60%, 70%, 80%, 90%, 100%, 2 fold, 5 fold, 10 fold, 20 fold, 30 fold, 40 fold, 50 fold, 60 fold, 70 fold, 80 fold, 90 fold, 100 fold, 500 fold, 1000 fold or more, when the agent is part of the glycosphingolipid-agent complex, compared to when the agent is delivered into cells alone.

In some embodiments, the agent is delivered across mucosal barriers (e.g., by transcytosis), when the agent is attached to the glycosphingolipid to form a glycosphingolipid-agent complex. Mucosal barrier is composed of compact epithelial cell lining (e.g., in the stomach or in the intestines). The intestinal mucosal barrier, also referred to as intestinal barrier, refers to the property of the intestinal mucosa that ensures adequate containment of undesirable luminal contents within the intestine while preserving the ability to absorb nutrients. The gastric mucosal barrier is the property of the stomach that allows it to safely contain the gastric acid required for digestion.

In some embodiments, the agent is not able to cross mucosal barriers alone and is able to cross mucosal barriers in complex with the glycosphingolipids described herein. In some embodiments, the delivery of the agent across mucosal barriers is enhanced (e.g., by at least 20%) when the agent is in complex with the glycosphingolipids described herein, compared to when the agent is delivered alone. For example, the delivery of the agent across mucosal barriers is enhanced by at least 20%, at least 30%, at least 40%, at least 50%, at least 60%, at least 70%, at least 80%, at least 90%, at least 100%, at least 2 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold, at least 500 fold, at least 1000 fold or more, when the agent is in complex with the glycosphingolipids described herein, compared to when the agent is delivered alone. In some embodiments, the delivery of the agent across mucosal barriers is enhanced by 20%, 30%, 40%, 50%, 60%, 70%, 80%, 90%, 100%, 2 fold, 5 fold, 10 fold, 20 fold, 30 fold, 40 fold, 50 fold, 60 fold, 70 fold, 80 fold, 90 fold, 100 fold, 500 fold, 1000 fold or more, when the agent is in complex with the glycosphingolipids described herein, compared to when the agent is delivered alone.

To form a glycosphingolipid-agent complex, the agent is attached to the glycosphingolipid, e.g., covalently or non-covalently. In some embodiments, the agent is attached to the oligosaccharide of the glycosphingolipid. The agent may be attached to the oligosaccharide of the glycosphingolipid by any methods known in the art. In some embodiments, the agent is attached non-covalently, e.g., without limitation, by van der Waals forces, hydrophobic interaction, hydrogen bond interaction, or ionic interactions.

In some embodiments, the agent is attached covalently. For example, in some embodiments, the oligosaccharide of the glycosphingolipid may be functionalized with a reactive chemical group. One example of such reactive group is a "click chemistry handle."Click chemistry is a chemical approach introduced by Sharpless in 2001 and describes chemistry tailored to generate substances quickly and reliably by joining small units together. See, e.g., Kolb, Finn and Sharpless Angewandte Chemie International Edition (2001) 40: 2004-2021; Evans, Australian Journal of Chemistry (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiolyne addition; imine formation; and Michael additions (e.g., maleimide addition). Non-limiting examples of a click chemistry handle include an azide handle, an alkyne handle, or an aziridine handle. Azide is the anion with the formula N3—. It is the conjugate base of hydrazoic acid (HN3). N3— is a linear anion that is isoelectronic with CO2, NCO—, N2O, NO2+ and NCF. Azide can be described by several resonance structures, an important one being —N=N+=N—. An alkyne is an unsaturated hydrocarbon containing at least one carbon—carbon triple bond. The simplest acyclic alkynes with only one triple bond and no other functional groups form a homologous series with the general chemical formula CnH2n-2. Alkynes are traditionally known as acetylenes, although the name acetylene also refers specifically to C2H2, known formally as ethyne using IUPAC nomenclature. Like other hydrocarbons, alkynes are generally hydrophobic but tend to be more reactive. Aziridines are organic compounds containing the aziridine functional group, a three-membered heterocycle with one amine group (—NH—) and two methylene bridges (—CH2-). The parent compound is aziridine (or ethylene imine), with molecular formula C2H5N.

Other non-limiting, exemplary reactive groups include: acetals, ketals, hemiacetals, and hemiketals, carboxylic acids, strong non-oxidizing acids, strong oxidizing acids, weak acids, acrylates and acrylic acids, acyl halides, sulfonyl halides, chloroformates, alcohols and polyols, aldehydes, alkynes with or without acetylenic hydrogen amides and imides, amines, aromatic, amines, phosphines, pyridines, anhydrides, aryl halides, azo, diazo, azido, hydrazine, and azide compounds, strong bases, weak bases, carbamates, carbonate salts, chlorosilanes, conjugated diener, cyanides, inorganic, diazonium salts, epoxides, esters, sulfate esters, phosphate esters, thiophosphate esters borate esters, ethers, soluble fluoride salts, fluorinated organic compounds, halogenated organic compounds, halogenating agents, aliphatic saturated hydrocarbons, aliphatic unsaturated hydrocarbons, hydrocarbons, aromatic, insufficient information for classification, isocyanates and isothiocyanates, ketones, metal hydrides, metal alkyls, metal aryls, and silanes, alkali metals, nitrate and nitrite compounds, inorganic, nitrides, phosphides, carbides, and silicides, nitriles, nitro, nitroso, nitrate, nitrite compounds, organic, non-redox-active inorganic compounds, organometallics, oximes, peroxides, organic, phenolic salts, phenols and cresols, polymerizable compounds, quaternary ammonium and phosphonium salts, strong reducing agents, weak reducing agents, acidic salts, basic salts, siloxanes, inorganic sulfides, organic sulfides, sulfite and thiosulfate salts, sulfonates, phosphonates, organic thiophosphonates, thiocarbamate esters and salts, and dithiocarbamate esters and salts.

The agent to be attached to the oligosaccharides (e.g., via the reactive chemical group) may contain a corresponding chemical group that reacts with the oligosaccharides, thus resulting in covalent attachment. In some embodiments, the agent is attached to the oligosaccharide via a linker, e.g., a peptide linker. In some embodiments, the agent is a protein or a peptide. As such, one or more of the amino acids of the protein or peptide may be modified to include a chemical entity such as a carbohydrate group, a hydroxyl group, a phosphate group, a farnesyl group, an isofarnesyl group, a fatty acid group, a linker for attaching to the oligosaccharide.

Other aspects of the present disclosure provide agents that may be delivered by the glycosphingolipids described herein. The agent may be any bioactive agent or therapeutic agent. A "therapeutic agent" refers to an agent that has therapeutic effects to a disease or disorder. The complex between the glycosphingolipid and the therapeutic agent is referred to herein as the "glycosphingolipid-therapeutic agent complex." A therapeutic agent may be, without limitation, proteins, peptides, nucleic acids, polysaccharides and carbohydrates, lipids, glycoproteins, small molecules, synthetic organic and inorganic drugs exerting a biological effect when administered to a subject, and combinations thereof. In some embodiments, the therapeutic agent is an anti-inflammatory agent, a vaccine antigen, a vaccine adjuvant, an antibody, and enzyme, an anti-cancer drug or chemotherapeutic drug, a clotting factor, a hormone, a steroid, a cytokine, an antibiotic, or a drug for the treatment of cardiovascular disease, an infectious disease, an autoimmune disease, allergy, a blood disorder, a metabolic disorder or a skin disease. In some embodiments, the therapeutic agent is a protein or a peptide. In some embodiments, the protein or peptide is glucagon-like peptide-1 (GLP-1), or a functional fragment thereof. In some embodiments, the protein or peptide is Exendin-4, or a functional fragment thereof.

"Glucagon-like peptide-1 (GLP-1)" is a 30 amino acid long peptide hormone deriving from the tissue-specific posttranslational processing of the proglucagon gene. It is produced and secreted by intestinal enteroendocrine L-cells and certain neurons within the nucleus of the solitary tract in the brainstem upon food consumption. The initial product GLP-1(1-37) is susceptible to amidation and proteolytic cleavage which gives rise to the two truncated and equipotent biologically active forms, GLP-1(7-36)amide and GLP-1(7-37). Active GLP-1 composes two α-helices from amino acid position 13-20 and 24-35 separated by a linker region. GLP-1 possesses several physiological properties that make it (and its functional analogs) a subject of intensive investigation as a potential treatment of diabetes mellitus. Further, GLP-1 is has the ability to decrease blood sugar levels in a glucose-dependent manner by enhancing the secretion of insulin. Thus, GLP-1 has been associated with numerous regulatory and protective effects. GLP-1-based treatment has been associated with weight loss and lower hypoglycemia risks, two very important aspects of a life with diabetes.

"Exendin-4" is a peptide agonist of the glucagon-like peptide (GLP) receptor that promotes insulin secretion. Exendin-4 binds to the intact human Glucagon-like peptide-1 receptor (GLP-1R) in a similar way to GLP-1 and bears a 50% amino acid homology to GLP-1. Exendin-4 facilitates glucose control via augmentation of pancreas response (i.e. increases insulin secretion) in response to eating meals, suppressing pancreatic release of glucagon in response to eating, reducing rate of gastric emptying, suppressing appetite, and reducing liver fat content.

In some embodiments, the therapeutic agent is a vaccine antigen. A "vaccine antigen" is a molecule or moiety that, when administered to a subject, activates or increases the production of antibodies that specifically bind the antigen. In some embodiments, an antigen is a protein or a polysaccharide. Antigens of pathogens are well known to those of skill in the art and include, but are not limited to parts (coats, capsules, cell walls, flagella, fimbriae, and toxins) of bacteria, viruses, and other microorganisms. A vaccine typically comprises an antigen, and is intentionally administered to a subject to induce an immune response in the recipient subject. The antigen may be from a pathogenic virus, bacteria, or fungi.

Examples of pathogenic virus include, without limitation: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of pathogenic bacteria include, without limitation: *Helicobacter pyloris, Borelia burgdorferi, Legionella pneumophilia, Mycobacteria* spp. (e.g., *M. tuberculosis, M. avium, M. intracellulare, M. kansasii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), *Streptococcus* (viridans group), *Streptococcus faecalis, Streptococcus bovis, Streptococcus (anaerobic* spp.), *Streptococcus pneumoniae*, pathogenic *Campylobacter* sp., *Enterococcus* sp., *Haemophilus influenzae, Bacillus anthracis, Corynebacterium diphtherias, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira*, and *Actinomyces israelli*.

Examples of pathogenic fungi include, without limitation: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii*.

Other non-limiting examples of agents that may be delivered using the glycosphingolipids described herein are provided.

Non-limiting, exemplary chemopharmaceutically compositions that may be used in the liposome drug delivery systems of the present disclosure include, Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valmbicin, Vinblastine, Vincristine, Vindesine, and Vinorelbine. In some embodiments, the chemotherapeutic agent is Doxorubicin.

Examples of antineoplastic compounds include, without limitation: nitrosoureas, e.g., carmustine, lomustine, semustine, strepzotocin; Methylhydrazines, e.g., procarbazine, dacarbazine; steroid hormones, e.g., glucocorticoids, estrogens, progestins, androgens, tetrahydrodesoxycaricosterone, cytokines and growth factors; Asparaginase.

Examples of immunoactive compounds include, without limitation: immunosuppressives, e.g., pyrimethamine, trimethopterin, penicillamine, cyclosporine, azathioprine; irnmunostimulants, e.g., levamisole, diethyl dithiocarhamate, enkephalins, endorphins.

Examples of antimicrobial compounds include, without limitation: antibiotics, e.g., beta lactam, penicillin, cephalosporins, carbapenims and monobactams, beta-lactamase inhibitors, aminoglycosides, macrolides, tetracyclins, spectinomycin; Antimalarials, Amebicides, Antiprotazoal, Antifungals, e.g., amphotericin beta, antiviral, e.g., acyclovir, idoxuridine, ribavirin, trifluridine, vidarbine, gancyclovir.

Examples of parasiticides include, without limitation: anitihalmintics, Radiopharmaceutics, gastrointestinal drugs.

Examples of hematologic compounds include, without limitation: immunoglobulins; blood clotting proteins; e.g., antihemophilic factor, factor IX complex; anticoagulants, e.g., dicumarol, heparin Na; fibrolysin inhibitors, tranexamic acid.

Examples of cardiovascular drugs include, without limitation: peripheral antiadrenergic drugs, centrally acting antihypertensive drugs, e.g., methyldopa, methyldopa HCl; antihypertensive direct vasodilators, e.g., diazoxide, hydralazine HCl; drugs affecting renin-angiotensin system; peripheral vasodilators, phentolamine; antianginal drugs; cardiac glycosides; inodilators; e.g., amrinone, milrinone, enoximone, fenoximone, imazodan, sulmazole; antidysrhythmic; calcium entry blockers; drugs affecting blood lipids; ranitidine, bosentan, rezulin.

Examples of respiratory drugs include, without limitation: syapthomimetic drugs: albuterol, bitolterol mesylate, dobutamine HCl, dopamine HCl, ephedrine SO, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propanolol HCl; antimuscarinic drugs, e.g., anisotropine methylbromide, atropine SO4, clinidium Br, glycopyrrolate, ipratropium Br, scopolamine HBr.

Examples of neuromuscular blocking drugs include, without limitation: depolarizing, e.g., atracurium besylate, hexafluorenium Br, metocurine iodide, succinylcholine Cl, tubocurarine Cl, vecuronium Br; centrally acting muscle relaxants, e.g., baclofen.

Examples of neurotransmitters and neurotransmitter agents include, without limitation: acetylcholine, adenosine, adenosine triphosphate, amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, K+ channel toxins, Examples of antiparkinson drugs include, without limitation: amaltidine HCl, benztropine mesylate, e.g., carbidopa.

Examples of diuretic drugs include, without limitation: dichlorphenamide, methazolamide, bendroflumethiazide, polythiazide.

Examples of uterine, antimigraine drugs include, without limitation: carboprost tromethamine, mesylate, methysergide maleate.

Examples of hormones include, without limitation: pituitary hormones, e.g., chorionic gonadotropin, cosyntropin, menotropins, somatotropin, iorticotropin, protirelin, thyrotropin, vasopressin, lypressin; adrenal hormones, e.g., beclomethasone dipropionate, betamethasone, dexamethasone, triamcinolone; pancreatic hormones, e.g., glucagon, insulin; parathyroid hormone, e.g., dihydrochysterol; thyroid hormones, e.g., calcitonin etidronate disodium, levothyroxine Na, liothyronine Na, liotrix, thyroglobulin, teriparatide acetate; antithyroid drugs; estrogenic hormones; progestins and antagonists, hormonal contraceptives, testicular hormones; gastrointestinal hormones: cholecystokinin, enteroglycan, galanin, gastric inhibitory polypeptide, epidermal growth factor-urogastrone, gastric inhibitory polypeptide, gastrin-releasing peptide, gastrins, pentagastrin, tetragastrin, motilin, peptide YY, secretin, vasoactive intestinal peptide, sincalide.

Examples of enzymes include, without limitation: hyaluronidase, streptokinase, tissue plasminogen activator, urokinase, PGE-adenosine deaminase, oxidoreductases, transferases, polymerases, hydrolases, lyases, synthases, isomerases, and ligases, digestive enzymes (e.g., proteases, lipases, carhohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase,), esterases (e.g. sterol esterase), disaccharidases (e.g., sucrase, lactase, beta-galactosidase, maltase, isomaltase), DNases, and RNases.

Examples of intravenous anesthetics include, without limitation: droperidol, etomidate, fetanyl citrate/droperidol, hexobarbital, ketamine HCl, methohexital Na, thiamylal Na, thiopental Na.

Examples of antiepileptics include, without limitation, carbamazepine, clonazepam, divalproex Na, ethosuximide, mephenytoin, paramethadione, phenytoin, primidone.

Examples of peptides and proteins that may be used as therapeutic agents include, without limitation: ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor alpha, transforming growth factor beta, interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, lymphocye function-associated antigen, intercellular adhesion molecule, vascular cell adhesion molecule, Thy-1, antiporters, CA-15-3 antigen, fibronectins, laminin, myelin-associated glycoprotein, GAP, GAP-43, Exendin-4, and GLP-1.

Examples of cytokines and cytokine receptors include, without limitation: interleukin-1 (IL-1), IL-2, IL-3, 11,4, IL-5, IL-6, IL-7, IL-8, IL-9, IL-10, IL-11, IL-12, IL-13, IL-14, IL-15, IL-16, IL-17, IL-18, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor beta, tumor necrosis factor, lymphotoxin, Fas, granulocyte colony stimulating factor, granulocyte macrophage colony stimulating factor, interferon-alpha, interferon-beta, interferon-gamma.

Examples of growth factors and protein hormones include, without limitation: erythropoietin, angiogenin, hepatocyte growth factor, fibroblast growth factor, keratinocyte growth factor, nerve growth factor, tumor growth factor-alpha, thrombopoietin, thyroid stimulating factor, thyroid releasing hormone, neurotrophin, epidermal growth factor, VEGF, ciliary neurotrophic factor, LDL, somatomedin, insulin growth factor, insulin-like growth factor I and II.

Examples of chemokines include, without limitation: ENA-78, ELC, URO-alpha, GRO-beta, GRO-gamma, HRG, LIF, IP-10, MCP-1, MCP-2, MCP-3, MCP-4, MIP-1alpha, MIP-1beta, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2; alpha-chemokine receptors: CXCR1, CXCR2, CXCR3, CXCR4, CXCR5, CXCR6, CXCR7; beta-chemokine receptors: CCR1, CCR2, CCR3, CCR4, CCR5, CCR6, CCR7.

In some embodiments, antibodies that may be delivered using the delivery vehicle described herein target antigens including, without limitation: (a) anti-cluster of differentiation antigen CD-1 through CD-166 and the ligands or counter receptors for these molecules; (b) anti-cytokine antibodies, e.g., anti-IL-1 through anti-IL-18 and the receptors for these molecules; (c) anti-immune receptor antibodies, antibodies against T cell receptors, major histocompatibility complexes I and II, B cell receptors, selectin killer inhibitory receptors, killer activating receptors, OX-40, MadCAM-1, Gly-CAM1, integrins, cadherens, sialoadherens, Fas, CTLA-4, Fc.gamma.-receptors, Fcalpha-receptors, Fc.epsilon.-receptors, Fc.inu.-receptors, and their ligands; (d) anti-metalloproteinase antibodies, e.g., collagenase, MMP-1 through MMP-8, TIMP-1, TIMP-2; anti-cell lysis/proinflammatory molecules, e.g., perforin, complement components, prostanoids, nitron oxide, thromboxanes; and (e) anti-adhesion molecules, e.g., carcioembryonic antigens, lamins, fibronectins.

Non-limiting, exemplary antibodies and fragments thereof include: bevacizuinab (AVASTIN®), trastuzumab (HERCEPTIN®), alemtuzumab (CAMPATH®, indicated for B cell chronic lymphocytic leukemia,), gemtuzumab (MYLOTARG®, hP67.6, anti-CD33, indicated for leukemia such as acute myeloid leukemia), rituximab (RITUXAM®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MUX-447, MDX-22, MDX-220 (anti-TAG-72), IOR-05, IOR-T6 (anti-CD1), IOR EGF/R3, celogovab (ONCOSCINT® OV103), epratuzumab (LYMPHOCIDE®), pemtumomab (THERAGYN®) and Gliomab-H (indicated for brain cancer, melanoma). Other antibodies and antibody fragments are contemplated and may be used in accordance with the disclosure.

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1.

Examples of antiviral agents include, without limitation: reverse transcriptase inhibitors and nucleoside analogs, e.g. ddI, ddC, 3TC, ddA, AZT; protease inhibitors, e.g., Invirase, ABT-538; inhibitors of in RNA processing, e.g., ribavirin.

Other non-limiting examples of known therapeutics which may be delivered by coupling to a glycosphingolipid a ceramide structure described herein include:

(a) Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb);

(b) Ceclor, Lorabid, Dynabac, Prozac, Darvon, Permax, Zyprexa, Humalog, Axid, Gemzar, Evista (Eli Lily);

(c) Vasotec/Vaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.);

(d) Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer);

(e) Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Rernisar, Depo-Provera, Caverject, Detrusital, Estring, Healon, Xalatan., Rogaine (Pharmacia & Upjohn);

(f) Lopid, Accrupil, Dilantin, Cognex, Neurontin, Loestrin, Dilzem, Fempatch, Estrostep, Rezulin, Lipitor, Omnicef, FemHRT, Suramin, Clinafloxacin (Warner Lambert).

Further non-limiting examples of therapeutic agents which may be delivered by the glycosphingolipid-therapeutic agent complex of the present invention may be found in: Goodman and Gilman's The Pharmacological Basis of Therapeutics. 9th ed. McGraw-Hill 1996, incorporated herein by reference.

The delivery vehicle comprising a glycosphingolipid and an agent to be delivered, or a glycosphingolipid-agent complex (e.g., a glycosphingolipid-therapeutic agent) complex may be formulated into pharmaceutical compositions. In some embodiments, the pharmaceutical composition further comprises a pharmaceutically acceptable carrier. "Pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier"

may be a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the pharmaceutical compositions also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The pharmaceutical compositions may conveniently be presented in unit dosage form and may be prepared by any of the methods well-known in the art of pharmacy. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

The formulation of the pharmaceutical composition may dependent upon the route of administration. Injectable preparations suitable for parenteral administration or intra-tumoral, peritunioral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The pharmaceutical composition ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

Other aspects of the present disclosure provide methods of delivering an agent (e.g., a therapeutic agent) into a cell or across a mucosal surface, the method comprising contacting the delivery vehicle, the glycosphingolipid-agent complex (e.g., the glycosphingolipid-therapeutic agent complex), or the pharmaceutical composition comprising the delivery vehicle or the glycosphingolipid-agent complex (e.g., the glycosphingolipid-therapeutic agent complex) with the cell or the mucosal surface, under conditions appropriate for uptake of the delivery vehicle or the agent into the cell or absorption of the delivery vehicle or the agent across the mucosal surface (e.g., via transcytosis). In some embodiments, the delivery vehicle, the glycosphingolipid-agent complex, or the pharmaceutical composition comprising the delivery vehicle or the glycosphingolipid-agent complex (e.g., the glycosphingolipid-therapeutic agent complex) are administered to a subject.

In some embodiments, an effective amount the delivery vehicle, the glycosphingolipid-agent complex, or the pharmaceutical composition comprising the delivery vehicle or the glycosphingolipid-agent complex (e.g., the glycosphingolipid-therapeutic agent complex) is administered to the subject. An "effective amount" is the amount necessary or sufficient to have a desired effect in a subject. The effective amount will vary with the particular condition being treated, the age and physical condition of the subject being treated, the severity of the condition, the duration of the treatment, the nature of the concurrent therapy (if any), the specific route of administration and other factors within the knowledge and expertise of the health care practitioner. For example, an effective amount could be that amount necessary to eliminate a tumor, cancer, or bacterial, viral or fungal infection. This amount will vary from individual to individual and can be determined empirically using known methods by one of ordinary skill in the art.

The delivery vehicle, the glycosphingolipid-agent complex, or the pharmaceutical composition comprising the delivery vehicle or the glycosphingolipid-agent complex (e.g., the glycosphingolipid-therapeutic agent complex) may be administered by any route. Routes of administration include enteral routes, such as oral and any other means by which the gastrointestinal tract is involved, and parenteral routes, such as by injection (subcutaneous, intravenous, intramuscular injection) or infusion (typically by intravenous route). The injection can be in a bolus or a continuous infusion.

The compositions methods described herein can be used in many contexts and a subject in whom they can be used is, for example, a human or vertebrate animal, such as a dog, cat, horse, cow, pig, sheep, goat, chicken, monkey, rat or mouse.

Methods of treating a disease or disorder are also provided. The delivery vehicle, the glycosphingolipid-agent complex, or the pharmaceutical composition comprising the delivery vehicle or the glycosphingolipid-agent complex (e.g., the glycosphingolipid-therapeutic agent complex) may be administered to a subject who has, has had or is susceptible to developing one or more conditions/diseases that require or would benefit from treatment. For example, the compositions described herein may be used to treat, prevent or ameliorate immune system deficiencies, infectious diseases (viral, fungal, bacterial or parasitic), autoimmune diseases, diabetes, blood disorders, cancers, metabolic disorders, allergies, inflammatory bowel disease and skin disorders. In addition, gangliosides attached to antigen can be administered to stimulate a subject's response to a vaccine. The antigen is selected from the group consisting of: an antigen that is characteristic of a pathogen, an antigen that is characteristic of an autoimmune disease, an antigen that is characteristic of an allergen and an antigen that is characteristic of a tumor. In some embodiments, the disease or disorder to be treated is diabetes. In some embodiments, the disease or disorder is infection, e.g., by a pathogenic virus, bacteria, or fungi. In some embodiments, the disease or disorder is cancer.

Immune system deficiencies include any disease or disorder in which a subject's immune system is not functioning normally or in which it would be useful to boost the subject's immune response, for example to eliminate a tumor or cancer (e.g. tumors of the brain, lung (e.g. small cell and non-small cell), ovary, breast, prostate, colon, as well as other carcinomas and sarcomas) or an infection in a subject.

Examples of autoimmune diseases include, without limitation: Addison's disease, diabetes mellitus (type 1), Graves' disease, interstitial cystitis, lupus erythematous, multiple sclerosis and Hashimoto's thyroiditis. Allergic conditions include eczema, allergic rhinitis or coryza, hay fever, bronchial asthma, urticaria (hives) and food allergies, and other atopic conditions.

Non-limiting, exemplary cancers include: neoplasms, malignant tumors, metastases, or any disease or disorder characterized by uncontrolled cell growth such that it would be considered cancerous. The cancer may be a primary or metastatic cancer. Cancers include, but are not limited to, adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, biliary tract cancer, osteosarcoma, fibrous histiocytoma, brain cancer, brain stem glioma, cerebellar astrocytoma, malignant glioma, glioblastoma., ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, acute lymphocytic and myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, choriocarcinoma, hematological neoplasm, adult T-cell leukemia, lymphoma, lymphocytic lymphoma, stromal tumors and germ cell tumors, or Wilms tumor. In some embodiments, the cancer is lung cancer, breast cancer, prostate cancer, colorectal cancer, gastric cancer, liver cancer, pancreatic cancer, brain and central nervous system cancer, skin cancer, ovarian cancer, leukemia, endometrial cancer, bone, cartilage and soft tissue sarcoma, lymphoma, neuroblastoma, nephroblastoma, retinoblastoma, or gonadal germ cell tumor.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Mucosal Absorption of Therapeutic Peptides by Harnessing the Endogenous Transcytotic Pathway of Glycosphingolipids One of the major challenges for applying protein and peptide biologics to clinical medicine is the lack of rational and efficient methods to circumvent epithelial and endothelial cell barriers separating large molecules from target tissues. In the case of epithelial cells lining mucosal surfaces, the pathway for absorption of large solutes is by transcytosis—a process of transcellular endosome trafficking that connects one surface of the cell with the other (host with environment). The same is true for transport of protein and peptide cargoes across tight endothelial barriers that separate blood from tissue—typified by the blood-brain barrier. Here, these problems are addressed by testing structure-function of the glycosphingolipids for their intracellular trafficking in transcytosis and for their use as vehicles to enable transcellular transport of therapeutic peptides.

These studies were informed by our findings that the structure of the ceramide (lipid) domain plays a decisive role in the intracellular trafficking of the glycosphingolipid GM1, the lipid receptor responsible for cholera toxin entry into the endoplasmic reticulum (ER) of host cells and required for disease (8). GM1 species containing ceramides with "kinked" cis-unsaturated C18:1. or C16:1 fatty acids, or non-native "short chain" C12:0 fatty acids, enter the sorting/recycling endosome of epithelial cells allowing for transport to various intracellular destinations: including the recycling pathway and retrograde pathway to the Golgi and ER. These lipids do not efficiently traffic into the late endosome-lysosome pathway. In contrast, GM1 sphingolipids with long saturated fatty acid chains (C16:0 or longer) sort almost exclusively into late endosomes and lysosomes (8). The sorting step separating the intracellular distributions of these closely related lipids emerges from the early sorting endosome, and it. was found to be a robust step across all cell lines so far tested. Our observations are consistent. with the two major models for lipid sorting: one by molecular shape (9-11) and the other by membrane microdomains (lipid rafts) (12-14).

In polarized epithelial cells, another pathway emerges from the sorting endosome and leads to membrane transport across the cell by transcytosis. The same GM1 species with cis-unsaturated or short-chain fatty acids that efficiently enter the recycling endosome also sort into this pathway (15, 16). By analogy with the bacterial toxins and viruses that bind glycosphingolipids for trafficking into host cells (17-20), this result suggested a means for enabling the uptake and transepithelial transport of protein or peptide therapeutic cargoes.

For mucosal delivery, the first attempt to test this idea showed that these glycosphingolipid species were capable of sorting a therapeutic cargo into the transcytotic pathway. But release into solution to effect transport across epithelial bathers in vitro, or absorption into the systemic circulation in vivo was not detectable (16). Additional structure-function studies for the glycosphingolipids in intracellular sorting were conducted and it was shown that modifications of the ceramide and oligosaccharide domains that enable the lipids to act as molecular carriers for mucosal absorption of therapeutic peptides, achieving levels of bioavailability comparable to that of intraperitoneal injection.

As demonstrated herein, a series of sphingolipids were synthesized and fused via their extracellular oligosaccharide domain to a reporter peptide or to GLP-1. Fusions to lipids with ceramide domains containing C6:0 or smaller fatty acids enabled >10-fold greater efficiencies of transcytosis in vitro, explained by active lipid sorting across the cell and amplified rates of release from cell membranes into solution after transcytosis. In vivo, the GLP-1-glycolipid fusion molecules were rapidly and systemically absorbed after gastric gavage to affect glucose tolerance as effectively as the intraperitoneal injection of GLP-1 alone.

Results

Structure Function Studies on the Ceramide Domain of GM1

To test if GM1 glycosphingolipids can be harnessed for biologic drug delivery, a non-degradable all D-isomer reporter peptide was first developed to enable structure function studies on the ceramide domain. The reporter peptide was designed to contain two functional groups, a biotin for high-affinity streptavidin-enrichment, and an alkyne reactive group to enable chemical ligation to fluorophore molecules for quantitative detection. C-terminal reactive aminooxy was used for coupling the reporter peptide to the oligosaccharide domain of the different GM1 species (FIG. 1A and FIG. 6A) (16). The functional groups on the reporter peptide, i.e. biotin, alkyne, fluorophore and combinations of, were tested to verify the absence of confounding effects on GM1 trafficking (FIG. 6B). This was assessed by confocal microscopy for endosome sorting and transcytosis, using fluorescent cholera toxin B-subunit to label the GM1-peptide fusion molecules (FIG. 6C). In all cases, the peptide-coupled GM1 species containing cis-unsaturated or short fatty acid ceramide domains sorted into small cytoplasmic vesicles and basolateral membranes consistent with the recycling and transcytotic pathways, whereas the peptide-coupled GM1 species containing saturated long fatty acid ceramide domains did not; they were sorted into larger cytoplasmic punctae consistent with the late endosome/lysosome instead. Both events were blocked at 4° C. consistent with uptake by endocytosis These results are consistent with the previous studies (8, 16) and validate the reporter construct.

Figure 1B:
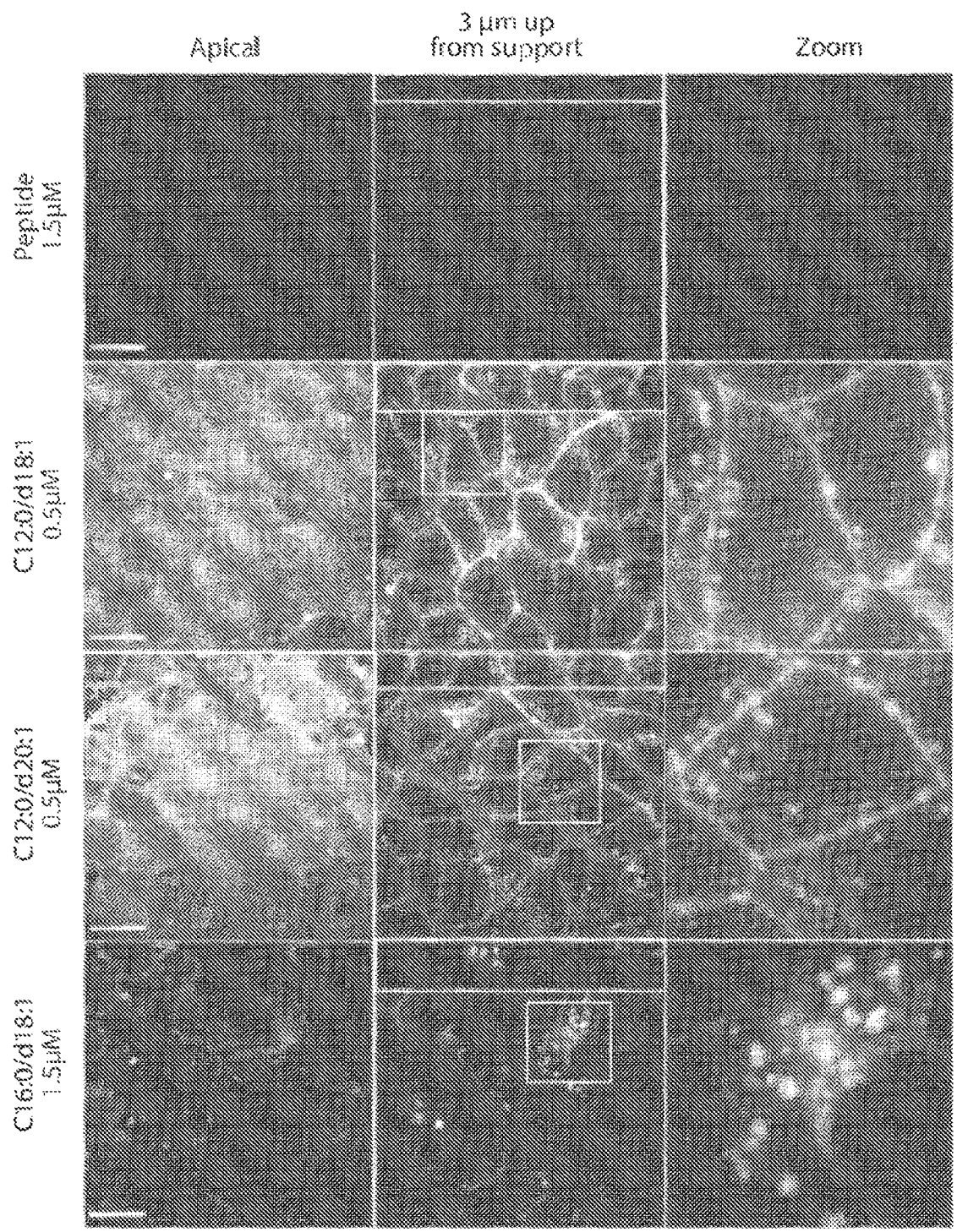
Figure 6A:
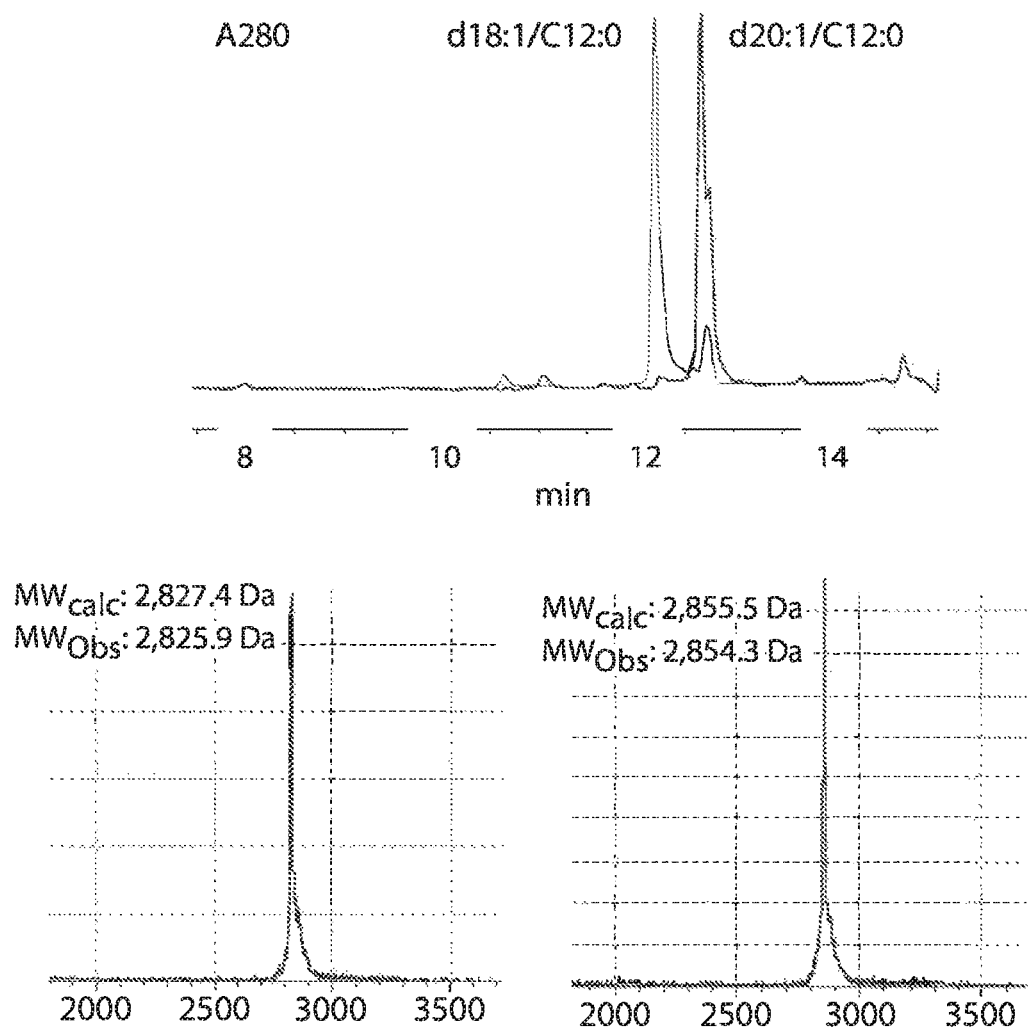
FIG. 6A to 6D.
Figure 6B:
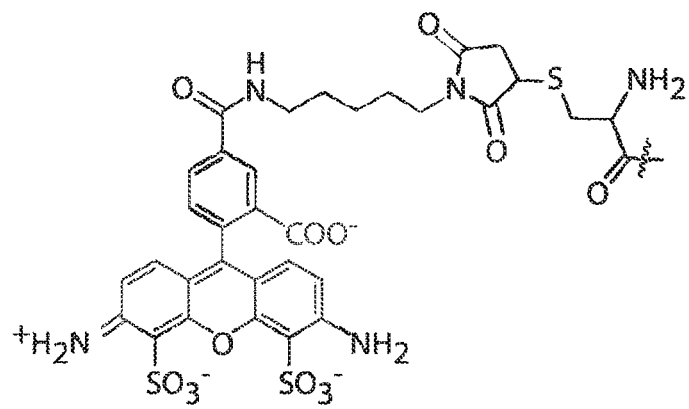
Figure 6B:
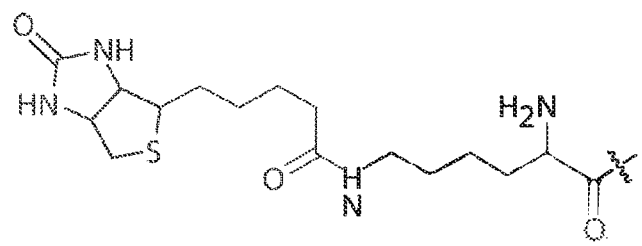
Figure 6B:
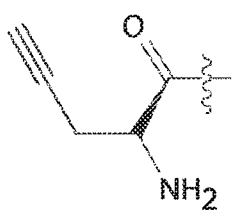
Figure 6B:
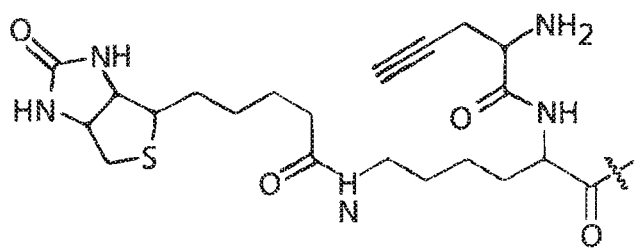
Figure 6C:
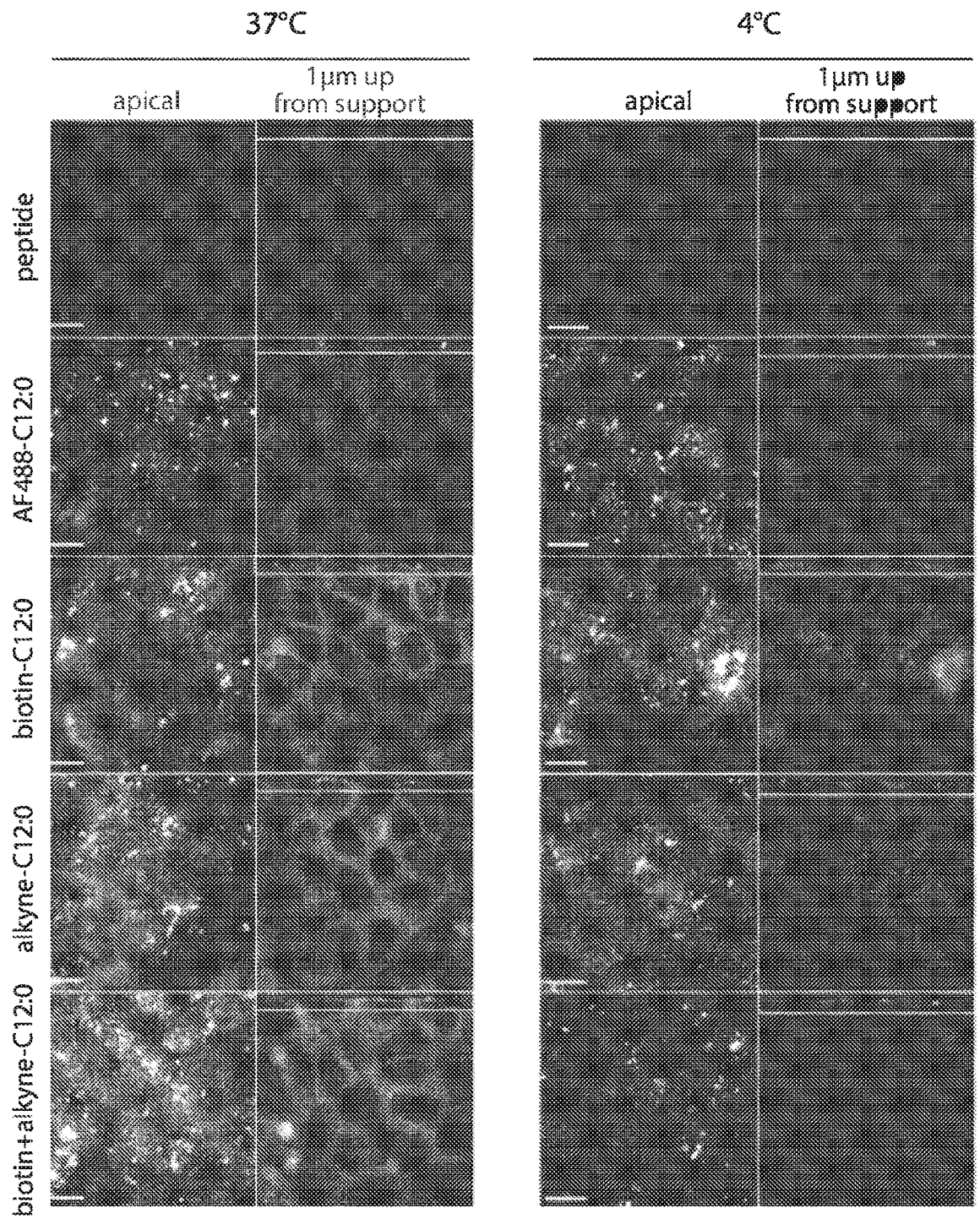
Figure 6D:
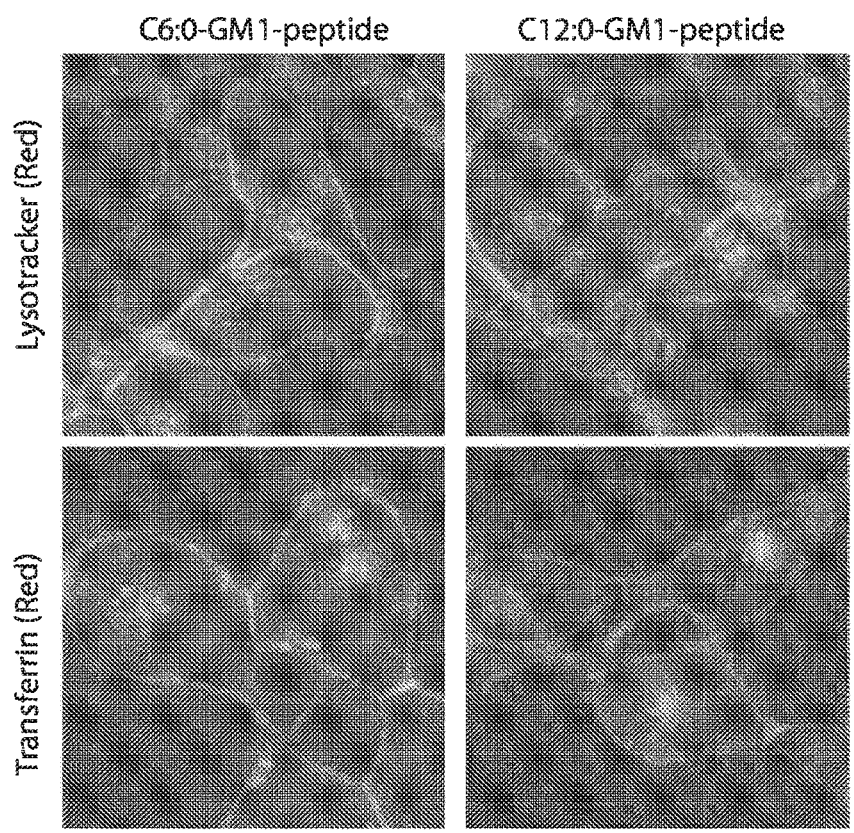

All glycosphingolipid-peptide fusion molecules subsequently prepared were coupled to Alexa Fluor-488 (AF488), purified by HPLC, and structures confirmed by mass spectrometry (FIG. 6A and Methods). When tested by pulse-chase in MDCK cells, the peptide-GM1 fusion molecules were internalized and sorted as predicted (8). The GM1 species containing long saturated fatty acids (C16:0-GM1) were localized to intracellular puncta consistent with sorting to the lysosome (FIG. 1B, bottom panels), and the GM1 species containing short fatty acids were sorted into the recycling and transcytotic pathways as evidenced by localization to apical and basolateral plasma membranes and small intracellular vesicles (FIG. 1B middle panels). This interpretation was confirmed using lysotracker to mark the lysosome and the transferrin receptor to mark the recycling endosome (FIG. 6D). The peptide alone did not bind or enter cell monolayers (top panels). Because GM1 used was originally purified from bovine brain to synthesize the different GM1 species, the end products comprise two isoforms of the long chain base: one containing a sphingosine chain of C18:1 and the other of C20:1. For the GM1 species containing C12:0 fatty acids, the two sphingosine-isoforms were purified and found to track identically in transcytosis (FIG. 1B, middle two panels). Thus, it is the structure of the fatty acid that dominates in the sorting reactions (8).

Figure 1C:
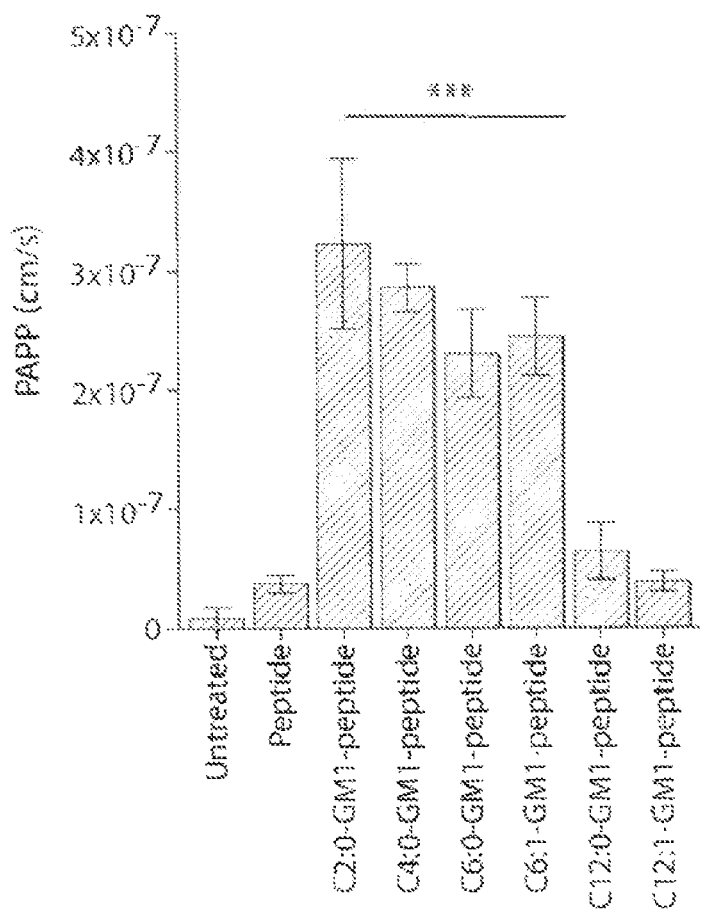
Figure 7A:
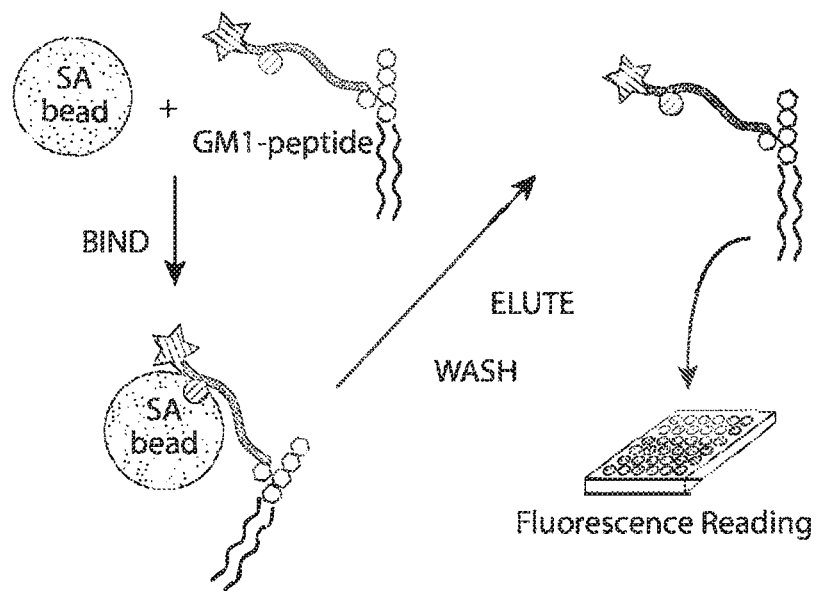
FIGS. 7A to 7G.
Figure 7B:
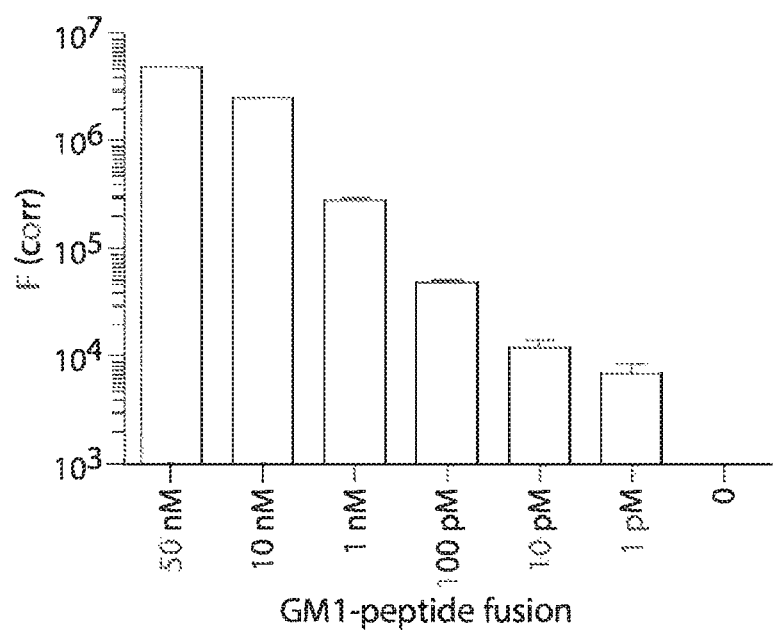
Figure 7C:
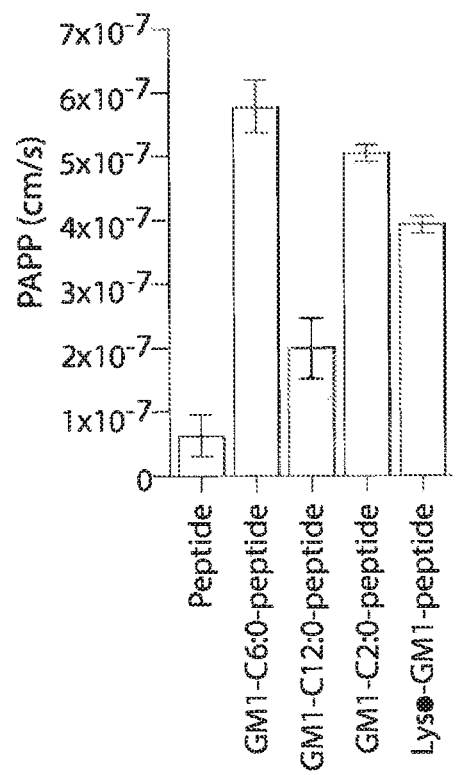
Figure 7D:
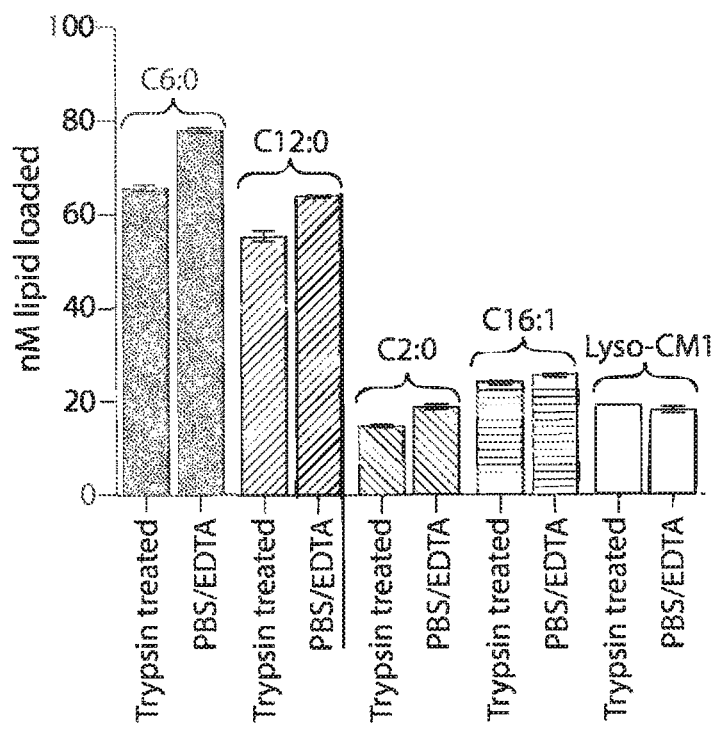

To test structure-function of the ceramide fatty acid chain, a quantitative assay for transcytosis was developed (FIGS. 7A and 7B). The assay is sensitive to picomolar concentrations and linear over a large 6-log dynamic range (FIG. 7B). Different GM1-peptide fusions (0.1 µM) were applied to apical reservoirs of polarized epithelial cell monolayers and transport to basolateral reservoirs analyzed after 3 hours by streptavidin-capture and in the microplate reader TECAN SPARK® 10M (FIG. 1C, FIG. 7C). Defatted bovine serum albumin (1% w/v) was added to the basolateral reservoir to amplify release of lipid-peptide fusion molecules from cell membranes to solution after transcytosis. In all studies, conditions for equal loading of the different GM1-peptide fusion molecules were determined by quantitative fluorescence measurement of cells treated with trypsin to release adherent glycosphingolipids not incorporated into the membrane bilayer (FIG. 7D). Transcytosis for the different GM1-peptide fusion molecules was quantified as an apparent permeability coefficient (PAPP; cm/s) and compared against both the unfused reporter peptide (labeled peptide) or untreated monolayers as negative controls (FIG. 1C, FIG. 7C).

Figure 1D:
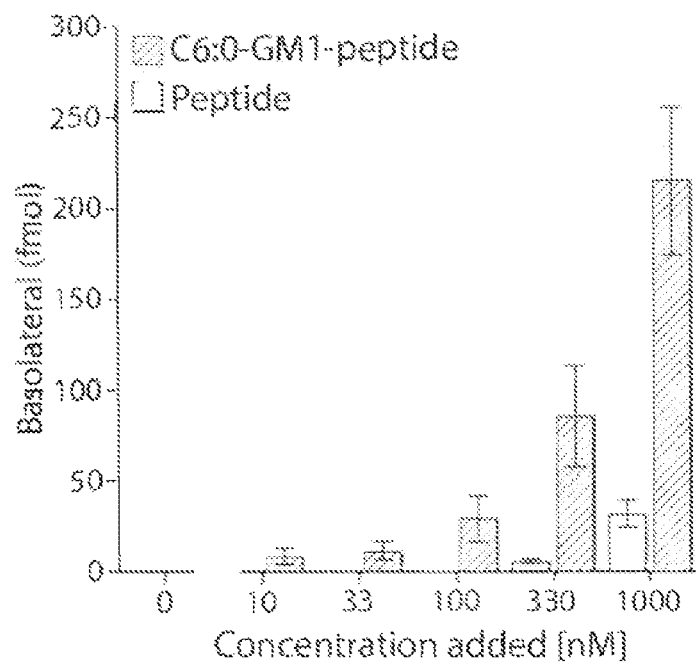
Figure 1E:
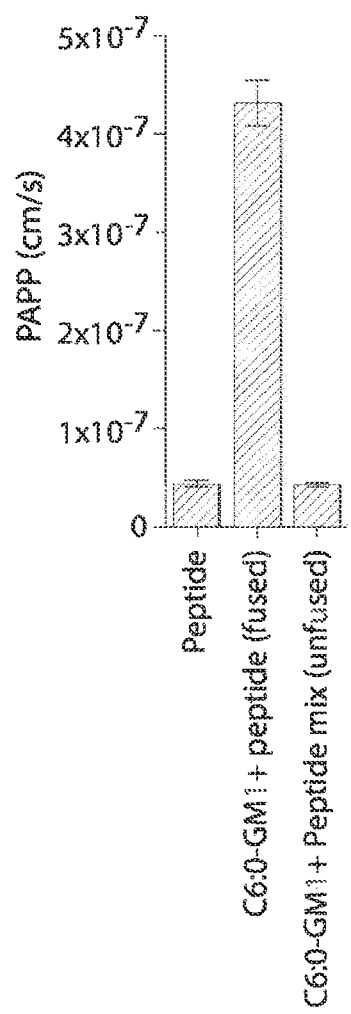
Figure 7E:
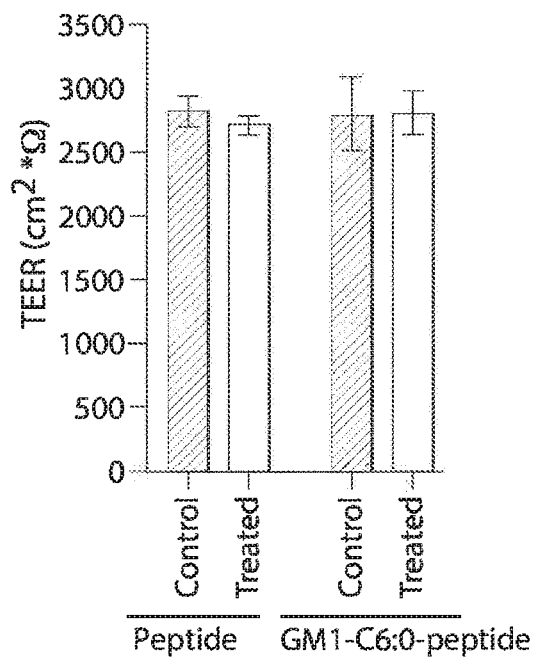
Figure 7F:
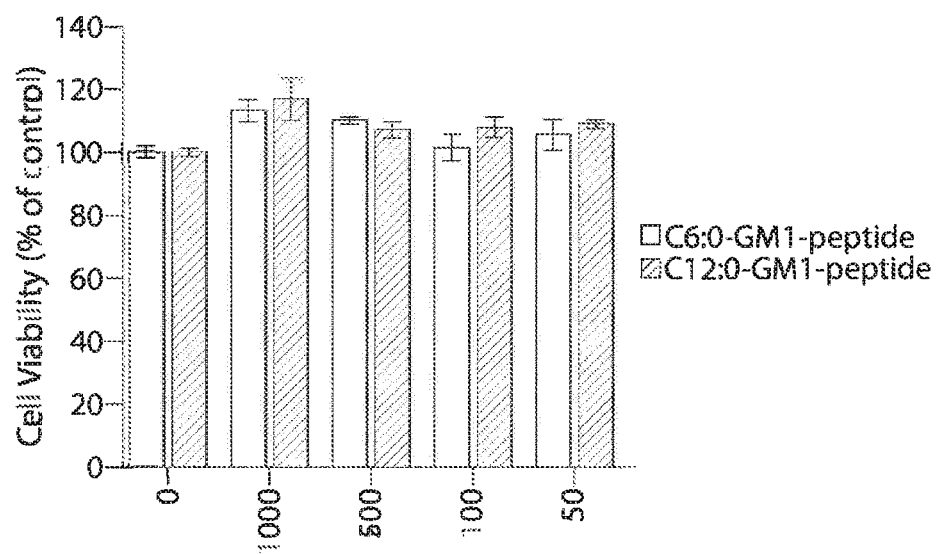
Figure 7G:
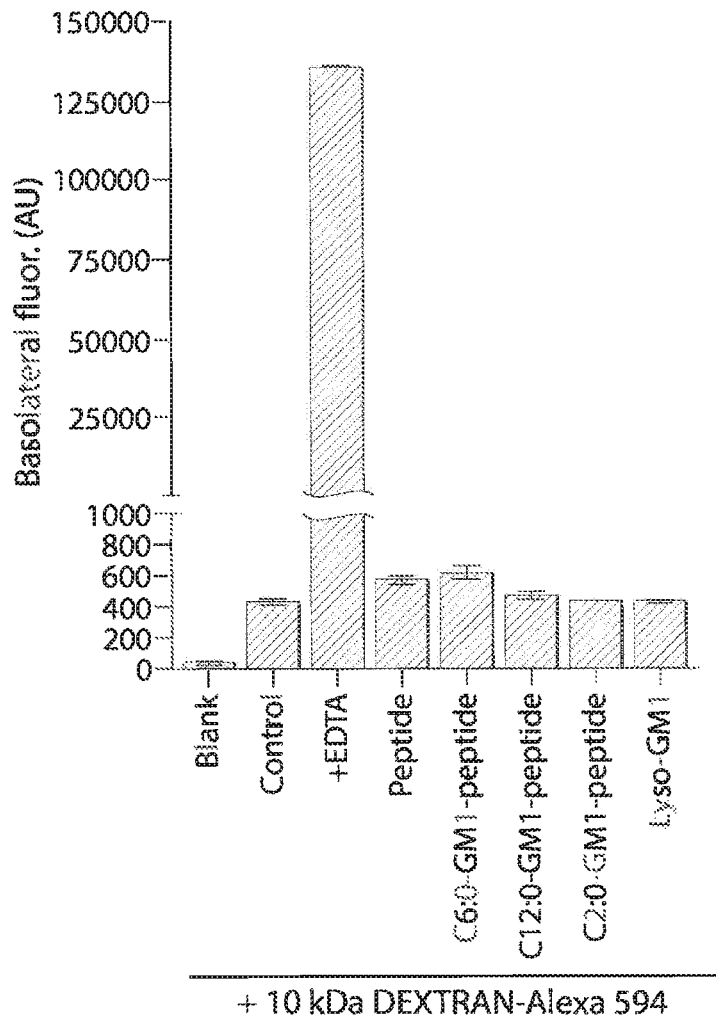

When tested on human intestinal T84 cell monolayers, an approximately 10-fold increase in transepithelial transport (PAPP) was found for the GM1 ceramide species containing C6:0, C4:0, C2:0 fatty acids, or lyso-GM1 as compared to controls. Introduction of an unsaturated cis-double bond to the short chain ceramide fatty acids (C12:1 and C6:1) had no apparent effect on transcytosis in comparison to the saturated species (C12:0 and C6:0) (FIG. 1C). This result is in contrast to the dramatic effect the cis-double bond induces in trafficking of the native long fatty-acid chain GM1 glycosphingolipids (8, 15). Transepithelial transport was dose-dependent for the C6:0-GM1-peptide fusion (grey bars) and greatly exceeded transport of the unconjugated reporter peptide (white bars) over a wide range of concentrations (FIG. 1D). Mixing experiments using unconjugated GM1 and reporter peptide as individual molecules confirmed that transcellular transport of the peptide cargo was dependent on fusion to the GM1 glycosphingolipid (FIG. 1E). Neither the unfused reporter peptide nor the GM1-peptide fusion had any detectable confounding effects on cell viability as determined by measurement of metabolic activity (MTT assay), or monolayer integrity and tight junction function assessed as trans-epithelial resistance (TEER) or dextran flux (FIG. 7E-7G).

Active Transport of the GM1-Peptide Fusions by Transcytosis

Figure 2A:
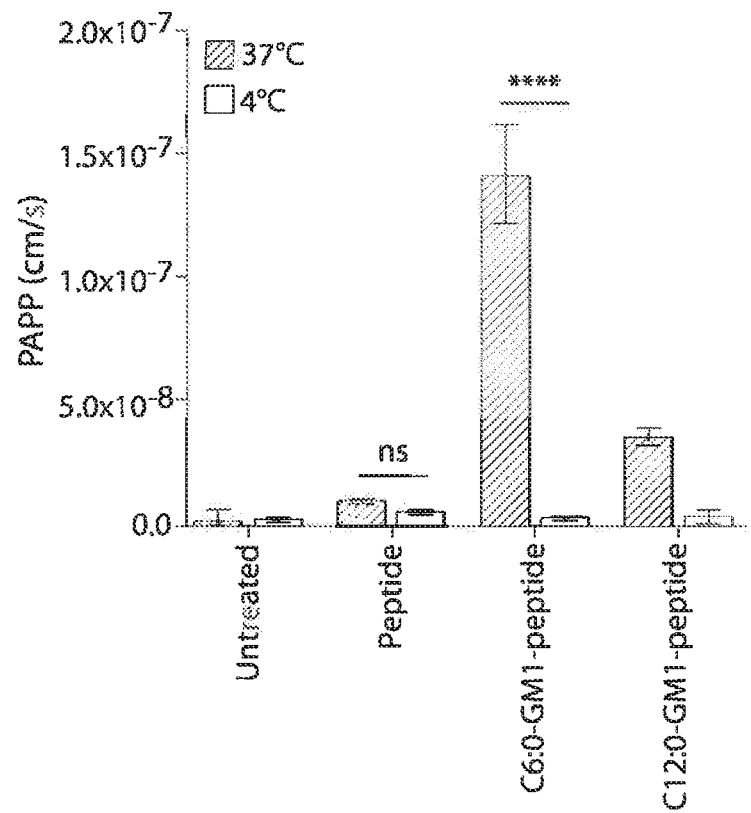
FIGS. 2A to 2D. Transport of short-chain GM1 ceramides occurs via transcytosis.
Figure 2B:
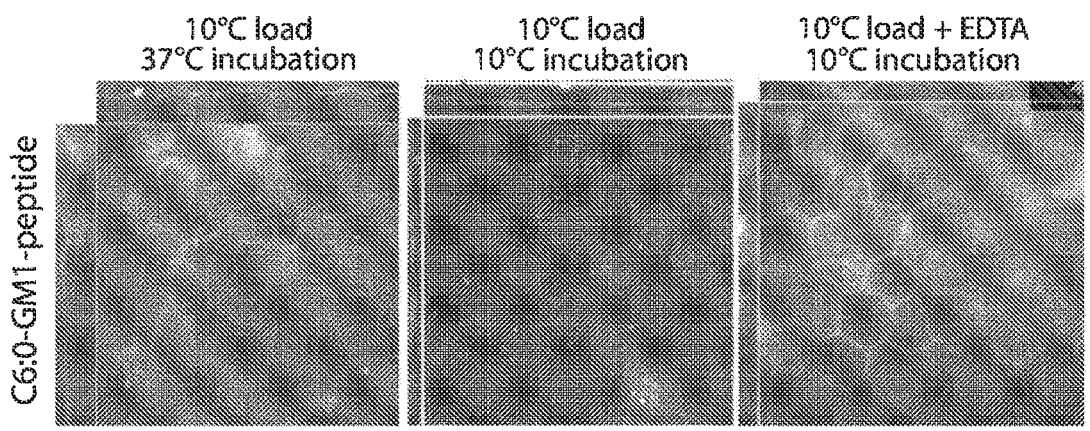

Several approaches were used to confirm that the mechanism of cargo transport across epithelial cell monolayers was by transcytosis and not by paracellular leak. First, transport across epithelial monolayers at 4° C. was tested. Such low temperature effectively stops all forms of membrane dynamics including transcytosis, but has minimal effects on paracellular solute diffusion. No detectable transport of GM1-peptide fusions across T84 cell monolayers was detected at 4° C., consistent with transport via transcytosis (FIG. 2A). The same results were obtained when transcytosis was measured by live cell confocal microscopy. In these experiments, the apical membranes of epithelial cell monolayers were incubated with the C6:0-GM1-peptide fusion at 10° C. for 45 min to allow for incorporation of the GM1 ceramide into the apical membrane with minimal uptake into the cell by endocytosis (FIG. 2B, x-z and y-z images). Monolayers were washed and then chased for 15 min at 37° C. or kept at a restrictive temperature of 10° C. The C6:0-GM1-peptide fusion was found localized to basolateral membranes in cells chased at 37° C., but not at 10° C. (FIG. 2B; left and middle panels respectively). Only after breaking open tight junctions by removal of extracellular $Ca^{2+}$ (EDTA treatment) did the GM1-peptide fusion molecule gain access to the basolateral membrane at 10° C. (FIG. 2B, right panel).

Figure 2C:
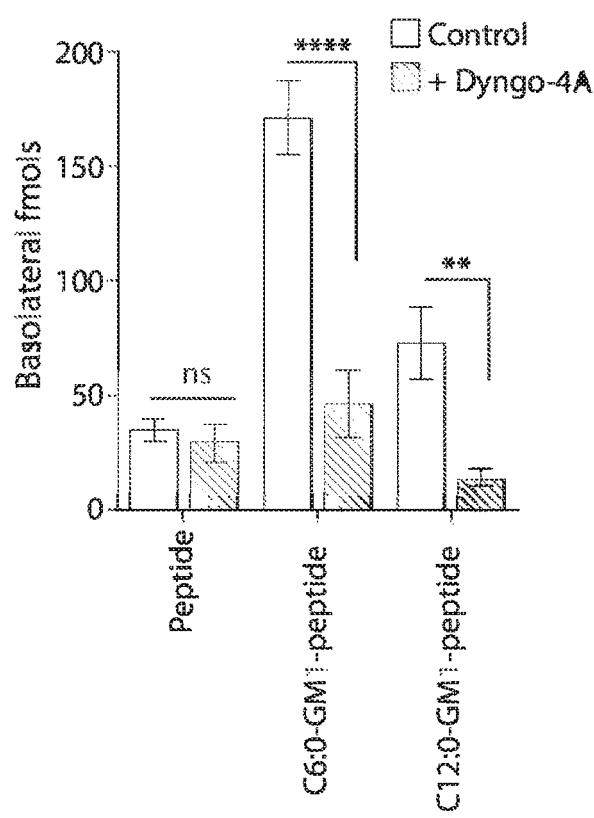
Figure 2D:
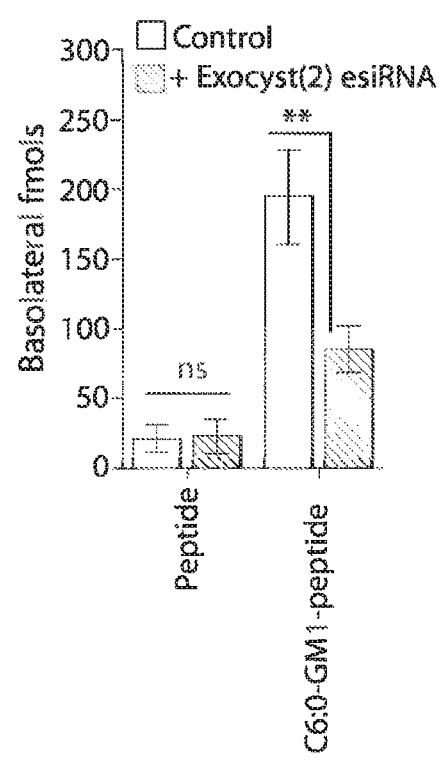

In a third approach, endocytosis at physiologic temperature was blocked using the dynamin inhibitor Dyngo-4A. For the C6:0 and C12:0 GM1-peptide fusion molecules, transport into the basolateral reservoir was strongly inhibited by Dyngo-4A treatment, consistent with active transcellular transport by transcytosis (FIG. 2C). In contrast, Dyngo-4A had no detectable effect on transport of the reporter peptide alone, as expected for diffusion of solutes by paracellular leak. Similar results were obtained using a genetic approach. The exocyst complex is necessary for efficient receptor-mediated transcytosis of immunoglobulins (21, 22), and esiRNA knock-down of EXOC2 subunit caused the predicted 50% decrease in trans-epithelial transport of the C6:0-GM1 peptide fusion molecule (FIG. 2D). In contrast, transport of the unfused reporter peptide was not affected by exocyst KD. Thus, fusion of a peptide cargo to certain GM1 species enables active transport of the peptide across the epithelial barrier by transcytosis.

Figure 3A:
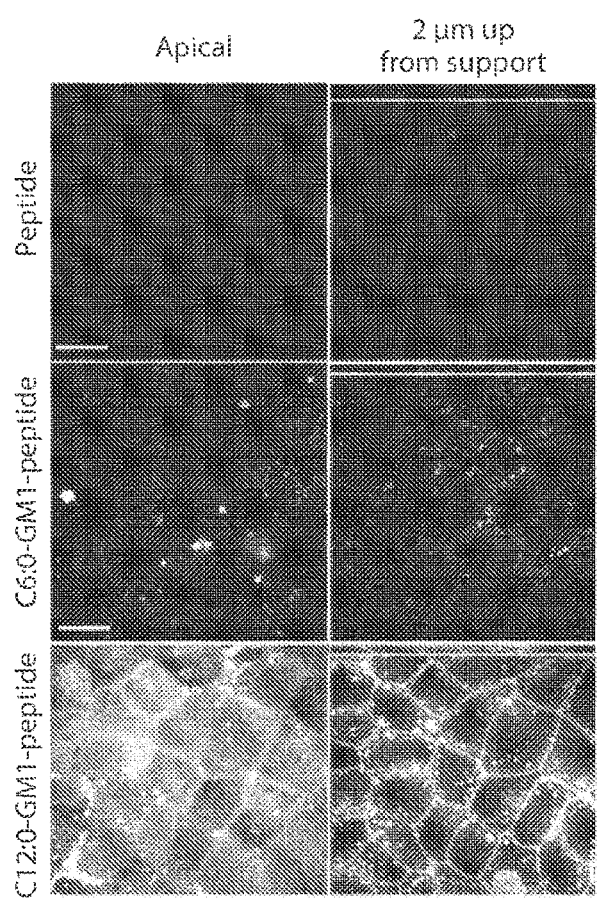
FIGS. 3A to 3E Release from membranes to solution by short-chain GM1 species.
Figure 3B:
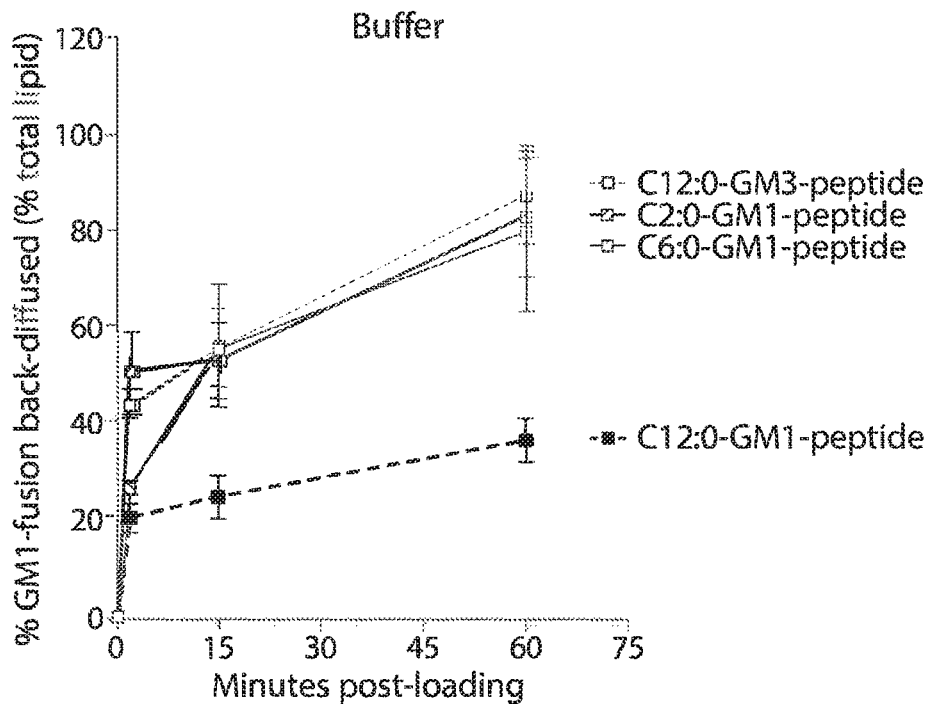
Figure 3C:
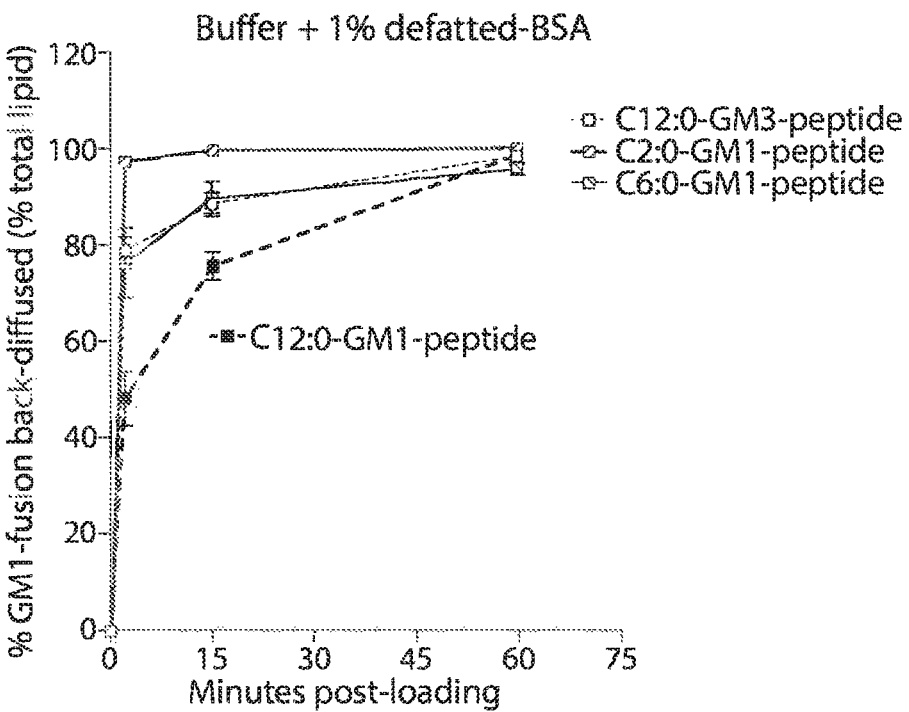
Figure 8A:
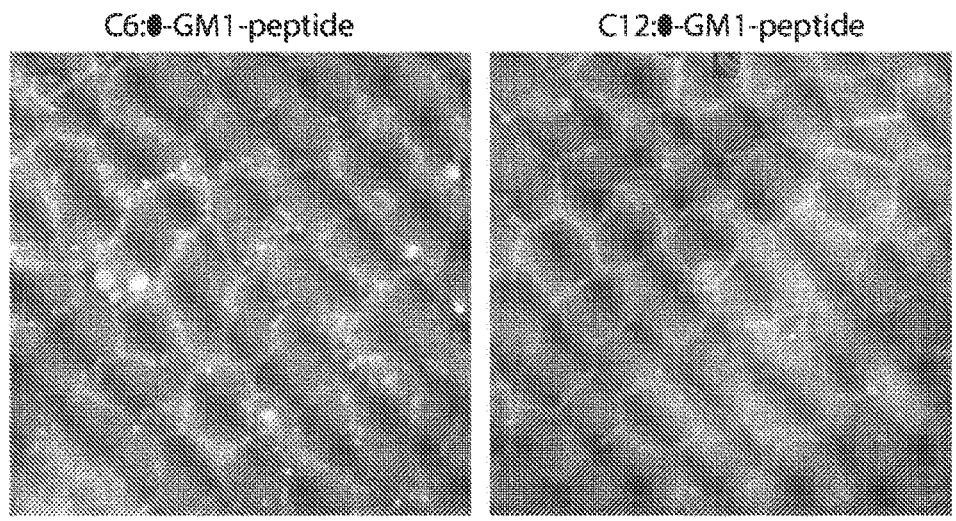
FIG. 8A to 8F.

Amplified Rates of Release into Solution by the Very Short Chain GM1 Species To explain how the very short chain fatty acids amplified transport across epithelial cell monolayers, first the rate of transcytosis was measured by pulse chase. Apical membranes of MDCK cell monolayers were loaded at 10° C. with equal amounts of C12:0 and C6:0-GM1-peptide fusions, washed, and then incubated at 37° C. and imaged by live-cell confocal microscopy over time. Transcytosis was measured as fluorescence at basolateral membranes. By this method, no detectable difference among the two GM1 species in the rate of transcytosis was found (FIG. 8A). In both cases, basolateral membranes were fluorescent after a 10 minute chase. At longer chase times, however, a dramatic difference between the C6:0- and C12:0-peptide fusion molecules was observed (FIG. 3A). Monolayers loaded with the C12:0-GM1 peptide fusion stained brightly at both the apical (bottom left panel) and basolateral membranes (bottom right panel). In stark contrast, monolayers loaded with the C6:0-GM1 peptide fusion showed no fluorescence (middle panels). This result was interpreted as indicating a higher rate of release from basolateral membranes to the solution causing release of cargo, and emptying the cell of the peptide-GM1 fusion over time. To test this idea, the rate of release from cell membranes to solution for the fluorescent GM1-peptide fusion molecules was quantified (see Methods). The rate of GM1 release into DMEM media alone was measured (FIG. 3B), as well as the rate of GM1 release into DMEM containing defatted bovine albumin (BSA), which amplifies lipid extraction from cell membranes (23) (FIG. 3C). Results show a faster and more complete diffusion from membrane to solution for the C6:0-GM1 fusion molecule (FIGS. 3B and 3C) compared to the longer chain C12:0-GM1-peptide molecule. Faster and more complete release into solution was also observed for the C2:0-GM1-peptide fusion molecule (FIGS. 3B and 3C). Thus, the greater efficiency for transepithelial transport by the short chain GM1 species is largely explained by their greater efficiency of release from membrane to solution after transcytosis.

Figure 3D:
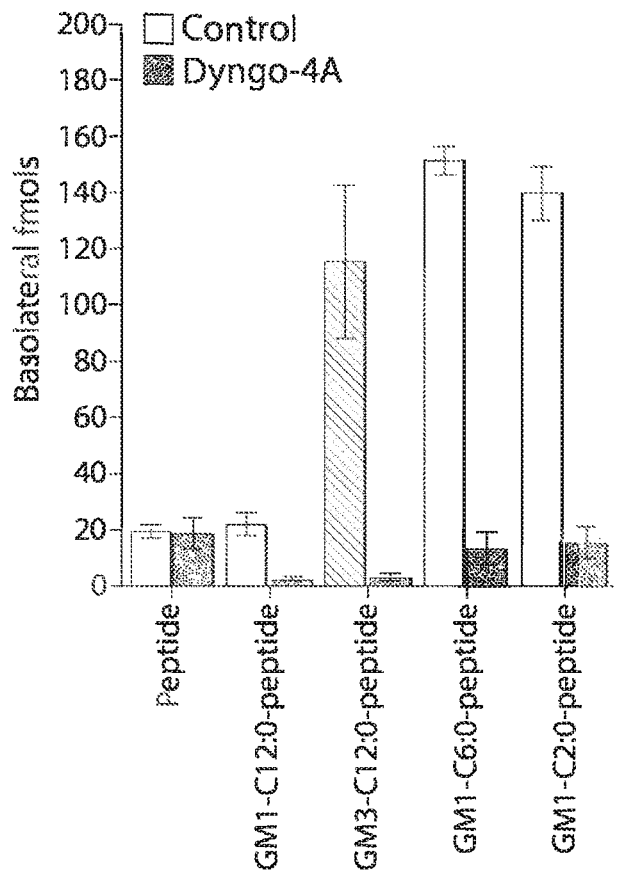
Figure 3E:
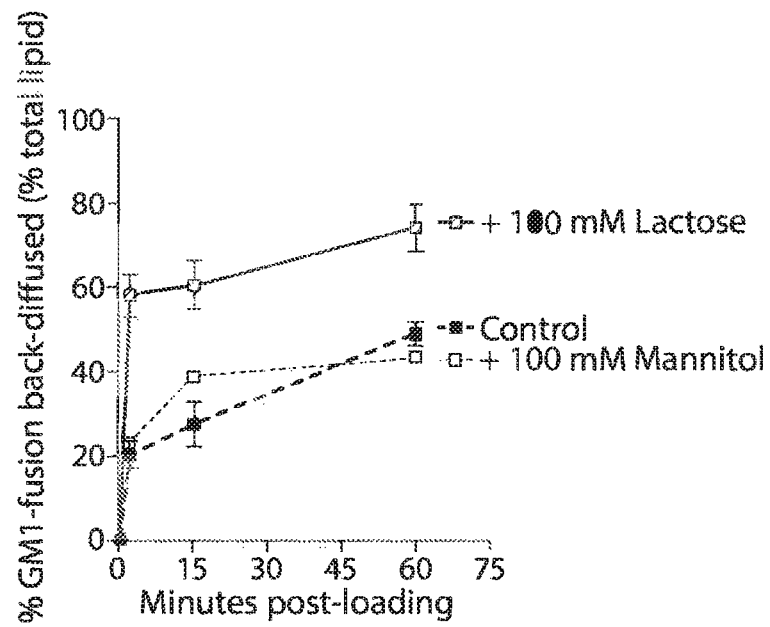
Figure 8B:
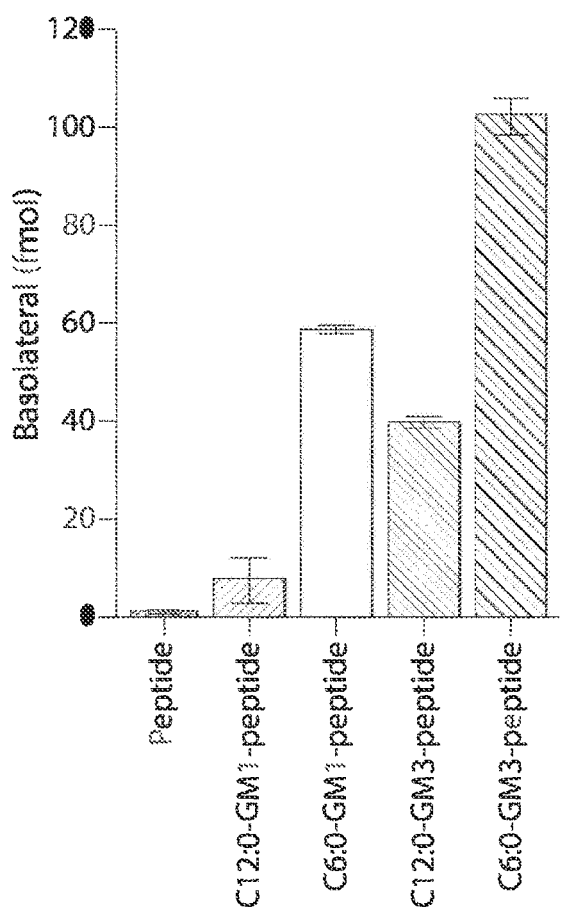
Figure 8C:
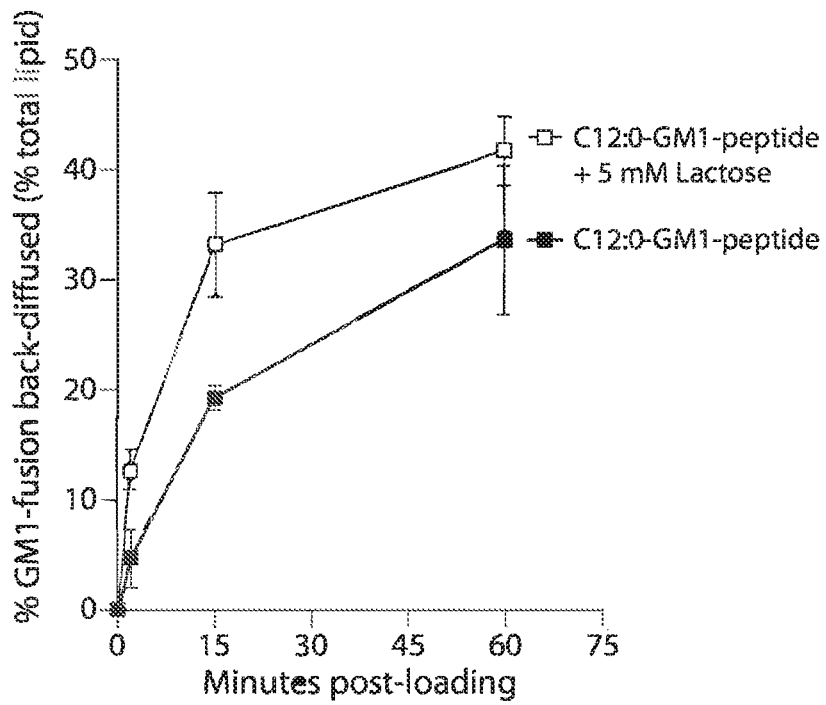
Figure 8D:
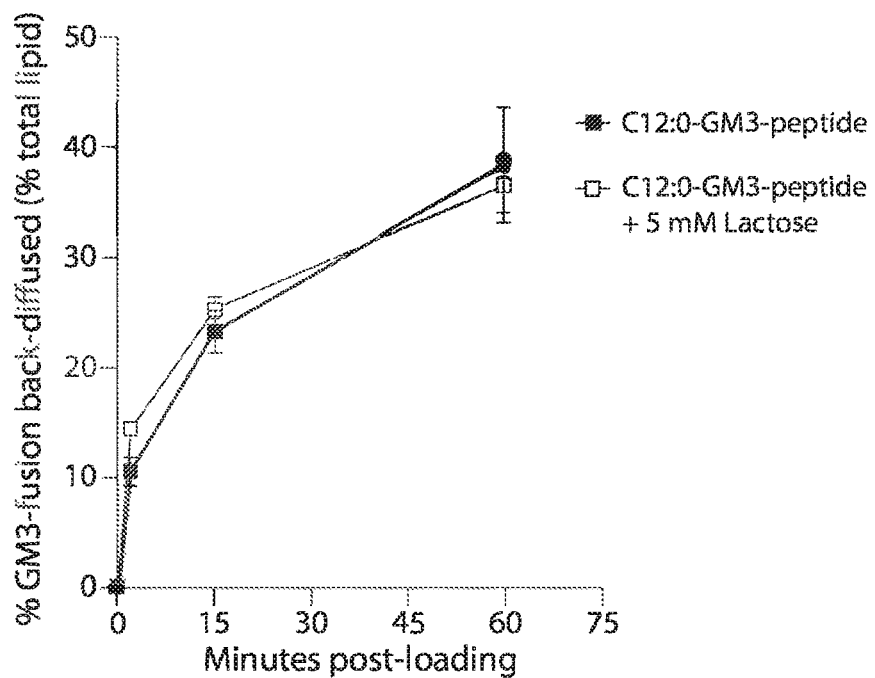
Figure 8E:
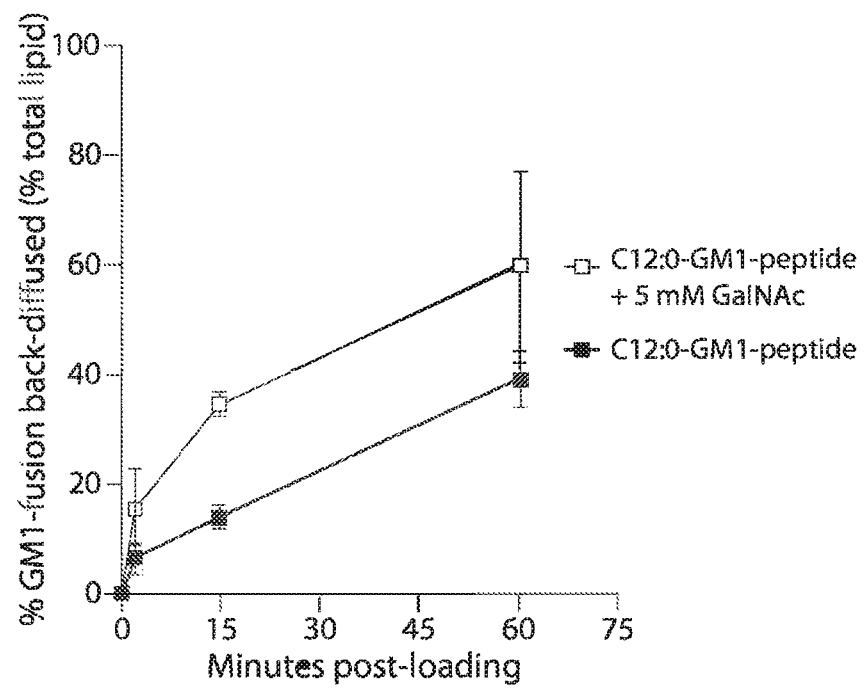
Figure 8F:
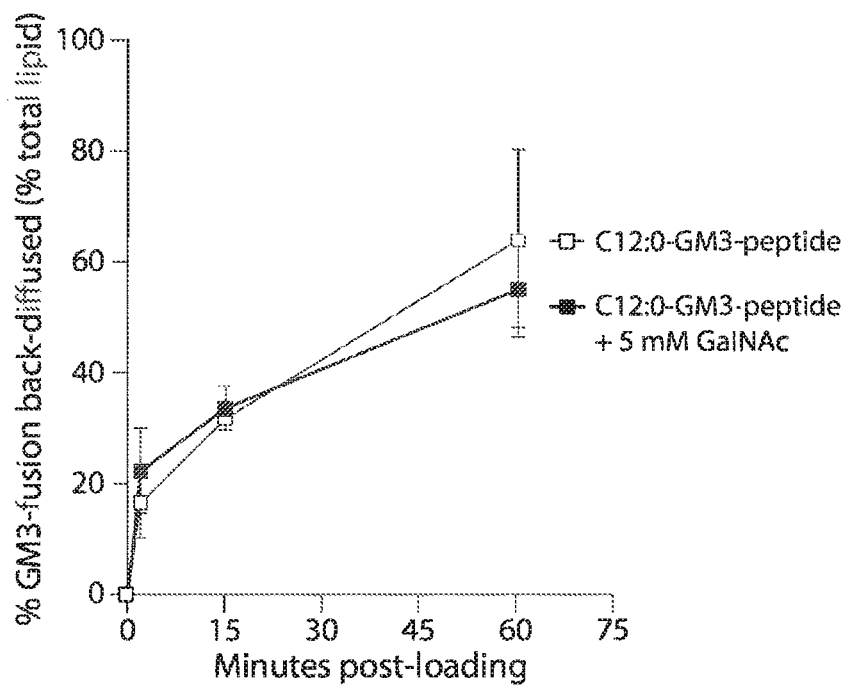

Glycosphingolipids contain another major functional domain in addition to the ceramide, the extracellular oligosaccharide head group. These are structurally diverse and operate in a variety of biologic activities (24). In all cases, however, the oligosaccharide head group acts to trap sphingolipids in the outer leaflet of cell membranes, thus rendering the lipids dependent on membrane trafficking for their distribution across the cell. To test if the effects of ceramide structure on transcytosis and membrane-release were specific to GM1 glycosphingolipids, or could be generalized to other glycosphingolipid species, the reporter peptide was fused to a GM3 ganglioside synthesized to contain ceramide domains with either C12:0 or C6:0 fatty acids. The oligosaccharide domain of GM3 differs from GM1 by the absence of two sugars and thus lacks the terminal galactose (and GalNAc) that functions strongly as a lectin-binding site in GM1. When tested for transcytosis, it was unexpectedly found that the GM3-C12:0-peptide fusion molecule crosses epithelial monolayers far more efficiently that the closely related GM1-C1.2:0-peptide fusion; and as efficiently as the GM1-C6:0 and C2:0 species (FIG. 3D). Similarly, transepithelial transport for the GM3-C6:0-peptide was approximately 2-fold greater than that observed for the GM1-C6:0-peptide when compared directly (FIG. 8B) Transport was strongly inhibited by pretreatment with the dynamin inhibitor Dyngo-4A, implicating active transcellular trafficking by transcytosis. In membrane-release studies, a higher rate of release to solution for the C12:0-GM3-peptide fusion was observed when compared to the GM1 fusion molecule (FIGS. 3B and 3C). Thus, the GM1 glycosphingolipid species appear to be retained in the membrane more tightly than the GM3 species containing the same ceramide domains. Because GM3 lacks a free terminal galactose, it was hypothesized that the GM1 lipids, which contain the terminal galactose, might be further tethered to the membrane by a form of lectin-binding at the cell surface. To test this idea, the rate of membrane release for the C12:0-GM1 species in the presence or absence of 100 mM lactose (Glc-Gal disaccharide) as a competitive ligand was studied (FIG. 3E). These studies show enhanced release from the membrane in the presence of excess free lactose, but not excess mannitol, implicating interaction with a galactose-specific lectin membrane tether (FIG. 3E). Thus, the oligosaccharide domain of the glycosphingolipids can also affect the efficiency of transport across epithelial barriers. To confirm this idea, the rate of membrane release for the C12:0-GM3 species that lacks the terminal n-acetyl galactosamine and galactose disaccharide (GalNAc) contained in GM1 were assessed. It was found that lactose at high 100 mM concentrations competed both the GM1 and GM3 species off the membrane but at lower doses (5 mM) lactose enhanced the release of only the GM1 species (FIGS. 8C and 8D). Likewise, the disaccharide GalNAc (5 mM) was effective at enhancing release of only the GM1-fusion molecules (FIGS. 8E and 8F). Thus, the oligosaccharide domain of the glycosphingolipids can also affect the efficiency of transport across epithelial barriers, likely by interacting with lectin-like molecules at the cell surface.

Glycosphingolipid Mediated Absorption Across Epithelial Barriers In Vivo

Figure 4A:
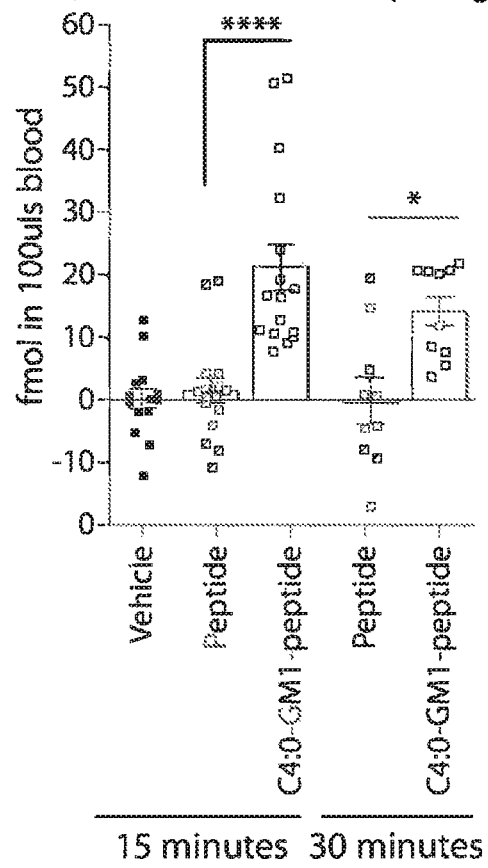
FIGS. 4A to 4E. Absorption across intestinal and nasal epithelial barriers in vivo.
Figure 4B:
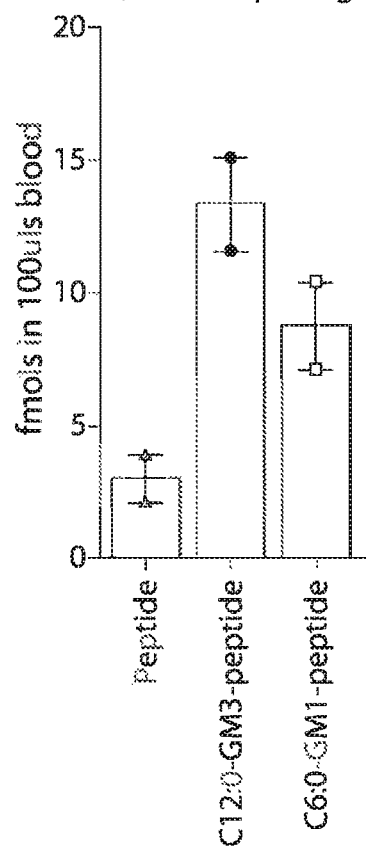
Figure 4C:
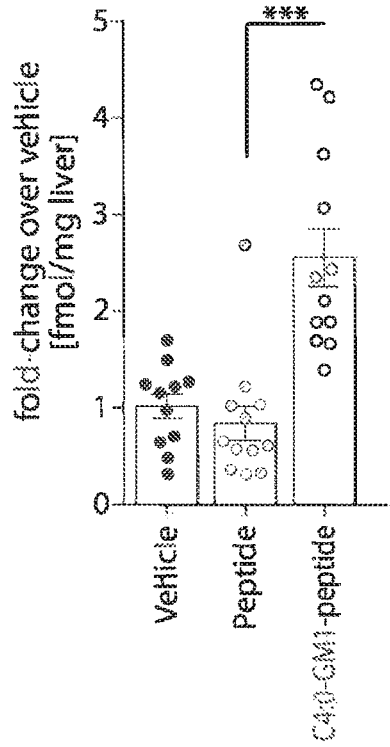

To test for glycosphingolipid-mediated transport across the intestine in vivo, the unfused reporter peptide or the C4:0-GM1-peptide fusion molecule were intragastrically gavaged to mice at equal doses (0.5 nmol/kg) and absorption into the blood analyzed after 15 and 30 minutes using the streptavidin-capture assay. At both time points, evidence of absorption into the systemic circulation was found for the GM1-peptide fusion molecules (nearly 3% of the applied dose), but not for the unfused peptide (FIG. 4A). The same results were obtained for the C12:0-GM3-peptide fusion molecule (FIG. 4B). The update into the liver was measured, where at 1 hour after gastric gavage, the glycosphingolipid-peptide fusion was found in the liver of treated mice, but not for the unfused peptide (FIG. 4C). Thus, fusion to the glycosphingolipids facilitated absorption of the peptide cargo across the intestine and into the two tissues sampled, blood and liver. The reporter peptide on its own was not detectably absorbed.

Figure 4D:
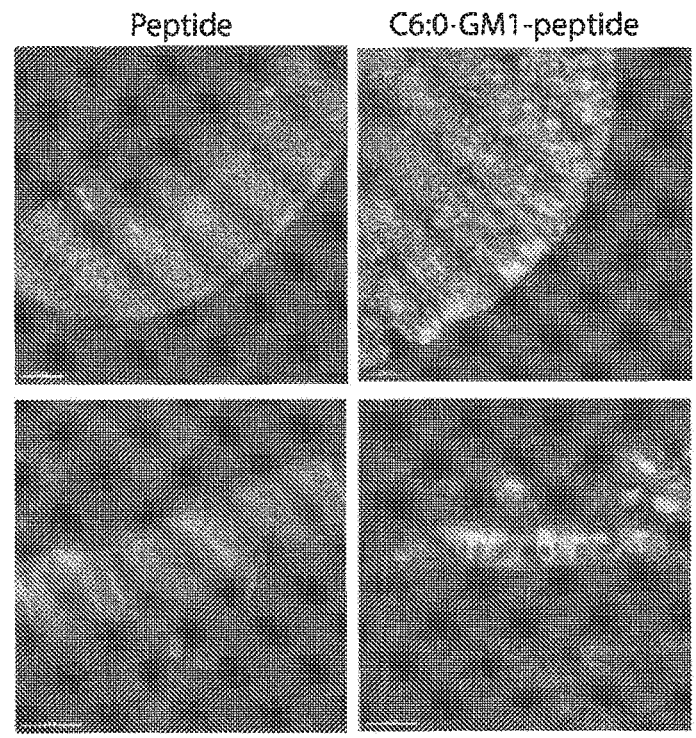
Figure 4E:
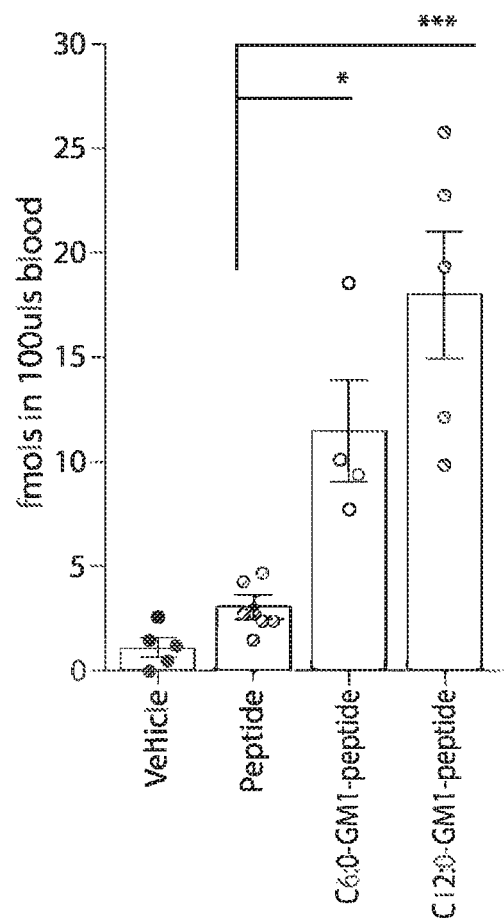

To test if these results can be generalized, the C6:0- and C12:0-GM1-peptide fusions were applied to the nasal epithelium, another tight epithelial mucosal surface. In this case, the C6:0-GM1-peptide (FIG. 4D) could be visualized by two-photon microscopy within the epithelial barrier in all regions of the nasal epithelium (FIG. 4D), including in areas of pseudostratified (top right panels) and simple columnar epithelial tissues (bottom right panels). Uptake of the unfused peptide, applied at the same dose, was very rarely detected (left panels). Absorption to the systemic circulation for the GM1-peptide fusion molecules was confirmed biochemically by measuring content in the blood 15 min after nasal administration (FIG. 4E). Here, approximately a 10-fold increase in blood levels for the GM1-peptide fusion molecules was found, compared to peptide alone, which is close to background. Unexpectedly, in the nasal epithelium, evidence was found for efficient absorption of the C12:0-GM1-peptide fusion molecules, similar to our results with the C12:0-GM3-peptide species in the intestine. The result suggests that different tissues may interact in different ways with the oligosaccharide domains of glycosphingolipids. In this case, the nasal epithelium may not bind the GM1 oligosaccharide, thus allowing for more efficient release from cell membranes into solution after transcytosis and systemic absorption.

Application of the C6:0-GM1 Species to Enable Oral Absorption of the Incretin Hormone GLP-1

Figure 9A:
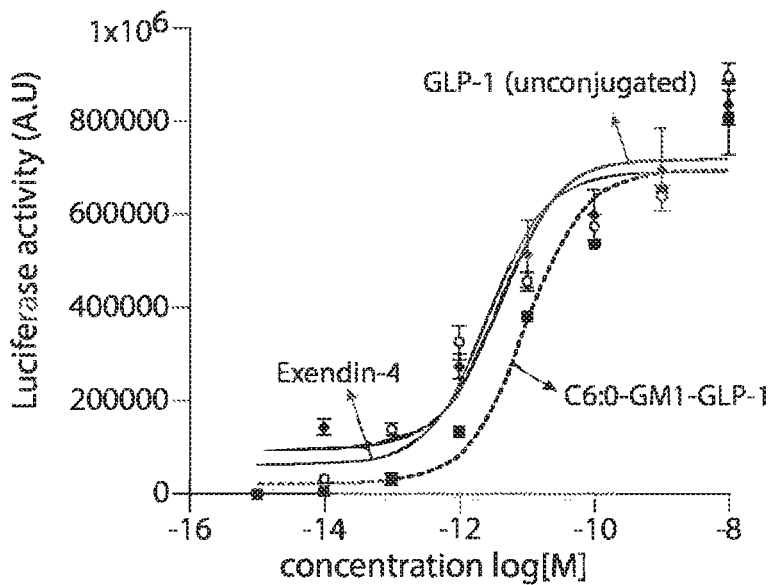
FIG. 9A to 9B.
Figure 10A:
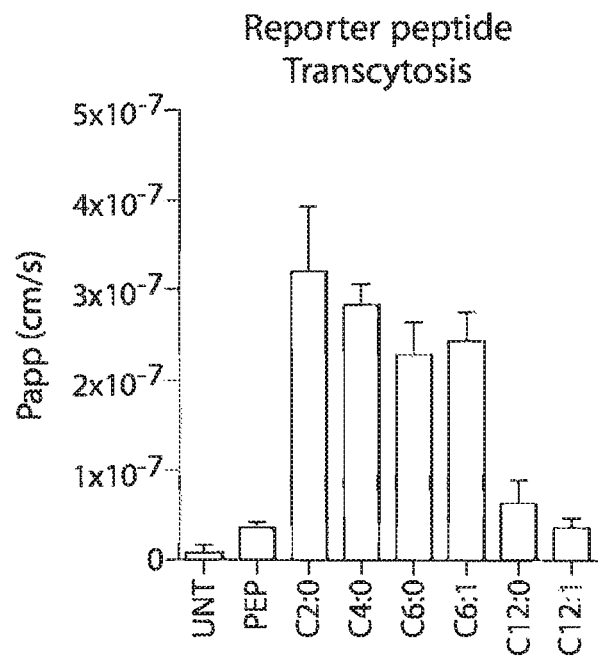
FIGS. 10A to 10C.
Figure 10B:
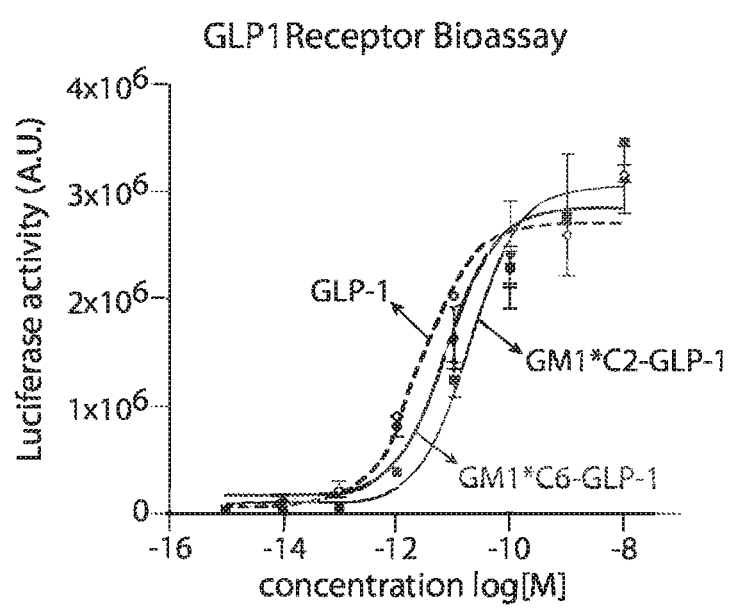
Figure 10C:
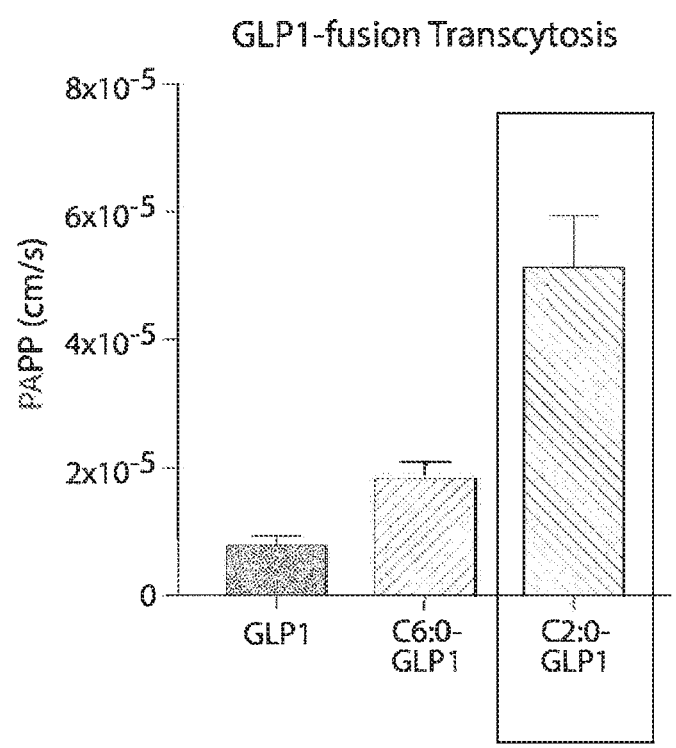
Figure 11A:
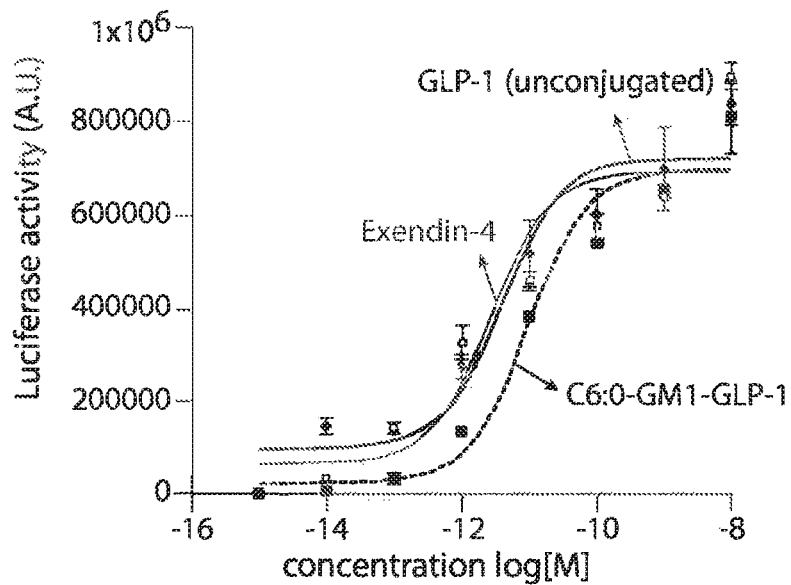
FIGS. 11A to 11B.
Figure 11B:
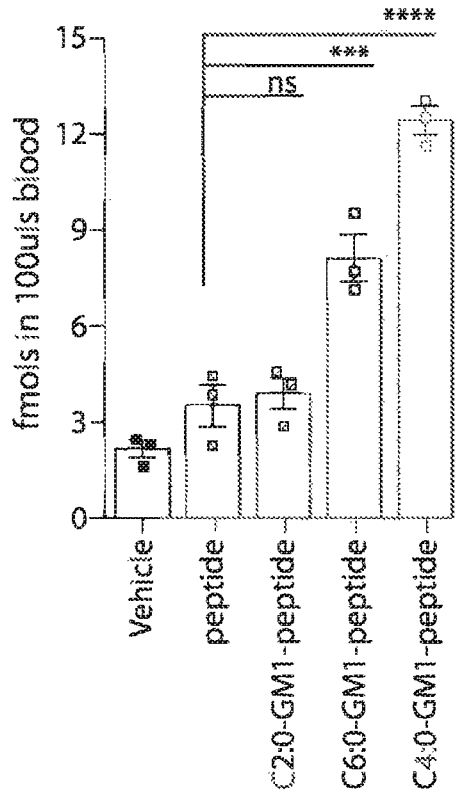

Glucagon-like peptide-1 (GLP-1) and related peptides have become important drugs in the management of type 2 diabetes mellitus, by both promoting weight reduction and sensitizing glucose-stimulated insulin release (25-27). A major factor limiting e clinical utility in many individuals is the fact that all currently available preparations must be delivered by subcutaneous injection. To test if the properties of glycosphingolipid trafficking could be applied to enable oral absorption of GLP-1, a long-half-life version of GLP-1 (FIG. 5A) was coupled with C-terminal peptide linker (termed here GLP-1 for simplicity) to the C6:0-GM1 ceramide species as described (16). The bioactivity of the glycolipid-GLP-1 fusion molecule was quantitatively assessed using HEK cells expressing the hGLP-1 receptor and CRE (cAMP) luciferase reporter (16). As controls, the commercially available long-acting GLP-1 (Exendin-4), and the unfused GLP-1-peptide were assessed in parallel (FIG. 9A, FIG. 10A). The fusion of C6:0-GM1 to GLP-1 caused some loss of function, but the molecule remained highly potent as an intecrin hormone, closely comparable to that of the controls.

Figure 5A:
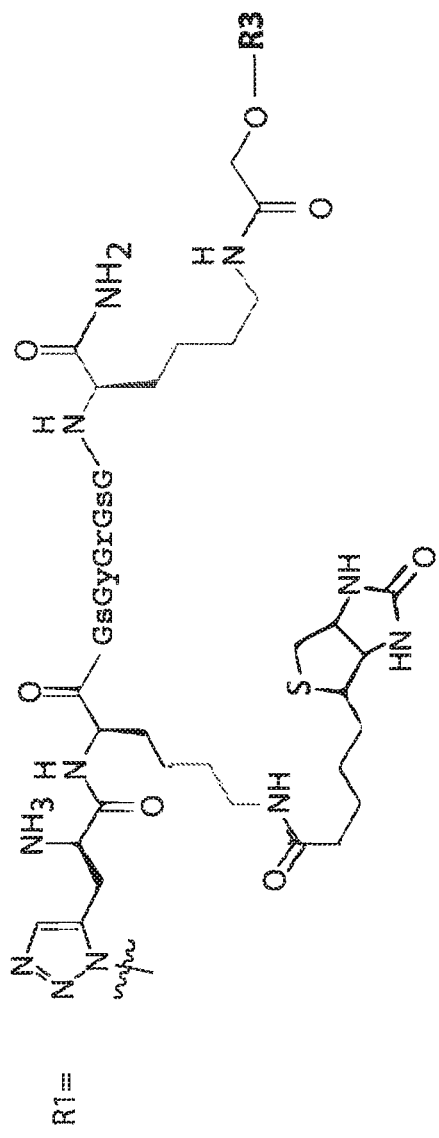
Figure 5A:
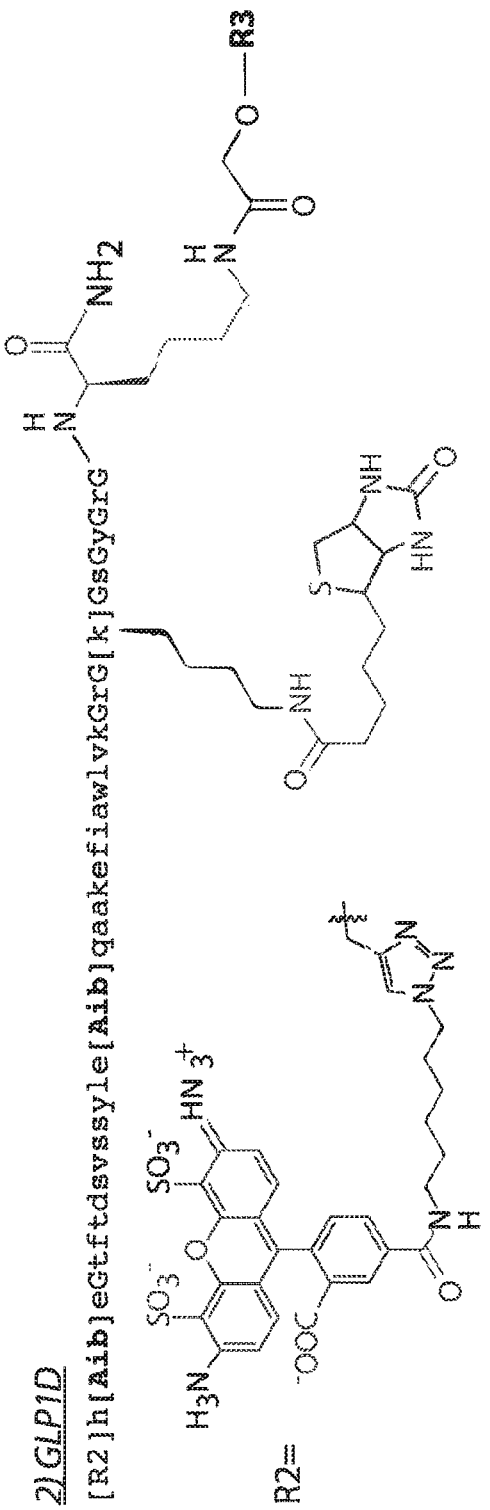
Figure 5B:
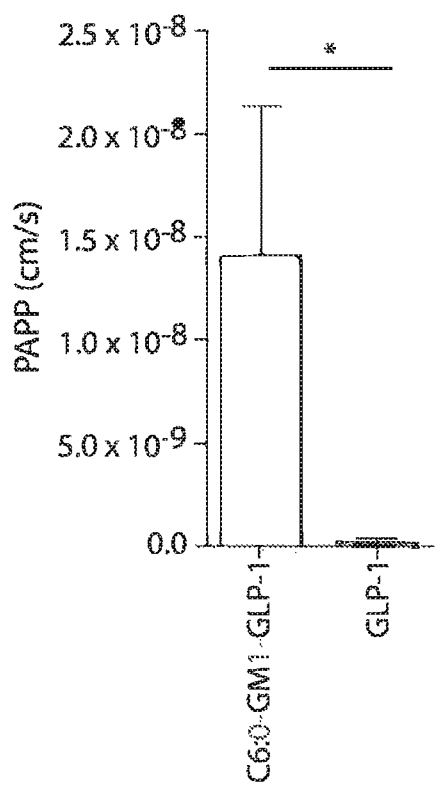

The GLP-1 peptide cargo is 40 residues, approximately 4-fold greater in size compared to the reporter peptide. First, the transport across intestinal T84 cell monolayers in vitro was studied to test if GM1 glycosphingolipids could transport such a larger cargo. In these studies, GLP-1 transport was quantified by luciferase bioassay as previously described (16) (FIG. 5B). Here, an even greater apparent effect of fusion to the glycoshingolipids on transepithelial GLP-1 transport (20-100-fold above controls) was found. This is explained by a much lower rate of paracellular leak for the larger sized 40-residue GLP-1 peptide. Such size-exclusion from tight junctions is a well-known determinant of paracellular solute diffusion across intact epithelial barriers.

Figure 5C:
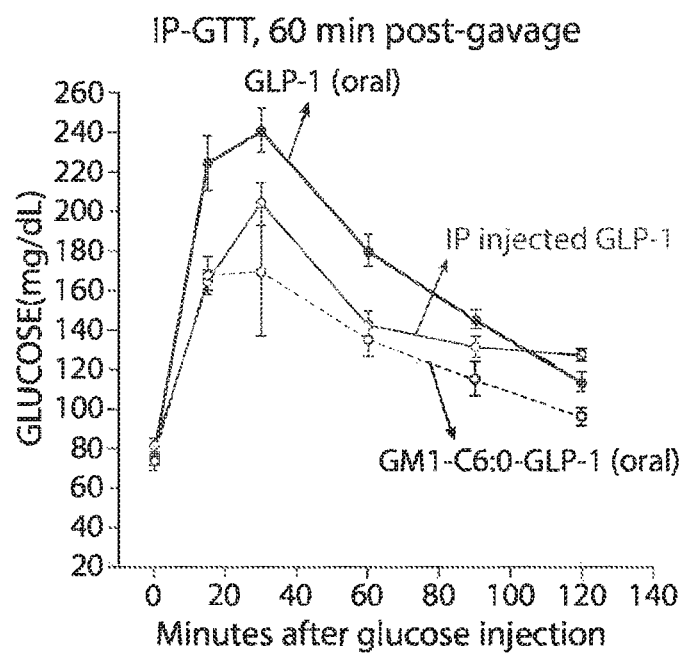
Figure 5D:
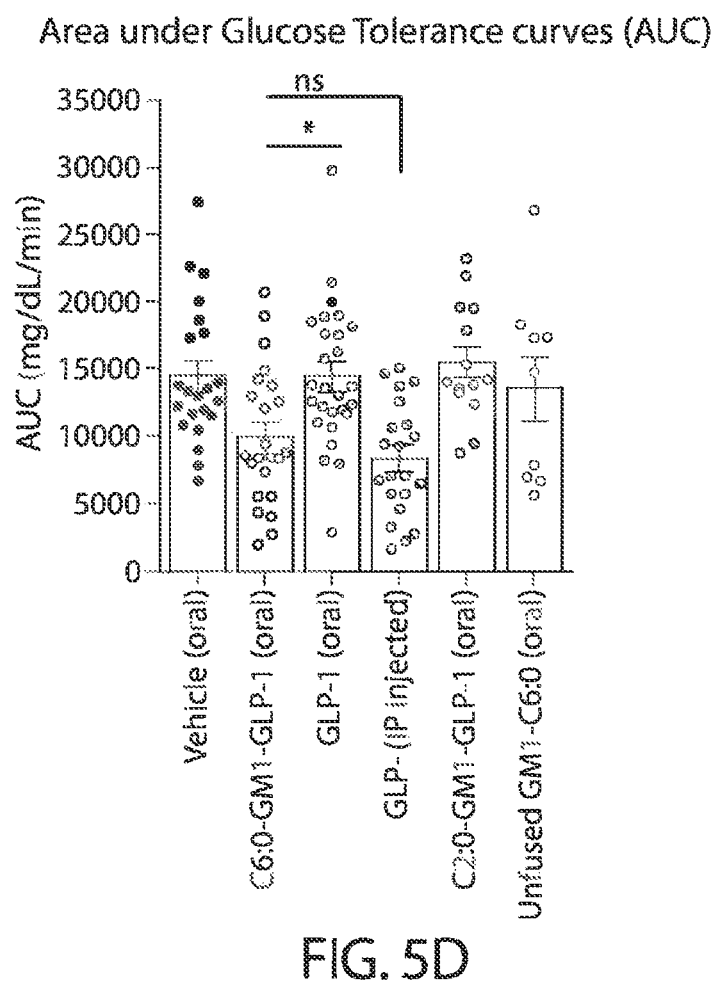

To test for absorption and biologic incretin activity in vivo, equal doses (10 nmol/kg) of the C6:0-GM1-GLP-1 fusion, the unfused GLP-1 peptide (GLP-1 oral), or vehicle into wild-type mice were gastrically gavaged, and effects on glucose metabolism were measured by glucose tolerance test (FIG. 5C). A lower peak and more rapid return of blood glucose to normal levels was found in the animals gavaged the C6:0-GM1-GLP-1 fusion molecules compared to animals gavaged the unfused GLP-1 peptide (FIGS. 5C and 5D). The effect on glucose tolerance by gastrically administered C6:0-GM1-GLP-1 was similar to the effect achieved by the intraperitoneal injection of GLP-1 peptide alone, implicating an equally high level of bioavailability for the gastrically-delivered GM1-fusion molecule (FIG. 5D).

Intestinal absorption of the C6:0-GM1-GLP-1 into the systemic circulation was confirmed in two ways. First, GLP-1 activity in blood samples was measured by streptavidin capture and quantitative luciferase bioassay (FIG. 5E). The results show absorption of the GM1-GLP-1 fusion molecule into the blood, but not for unfused GLP-1. In a second approach, an all D-amino acid (non-degradable) isomer of GLP-1 coupled to AF488 was synthesized to allow for direct quantitative measurement of the 40-residue isomer in the blood using the same streptavidin capture assay as described for our reporter peptide (FIG. 5A). Again, evidence for absorption of the GLP-1 cargo when fused to the C6:0-GM1 transport vehicle was found, but not for the unfused GLP-1 peptide (FIG. 5F). These experiments were performed in two different laboratories, using two different animal facilities with the same results. In all assays (FIGS. 5C-5F), it was found that the efficiency of intestinal absorption enabled by fusion to C6:0-GM1 was again almost as efficient as for IP injection of the peptide alone, implicating a high level of bioavailability for the GM1-fusion molecules applied by gastric gavage.

Figure 9B:
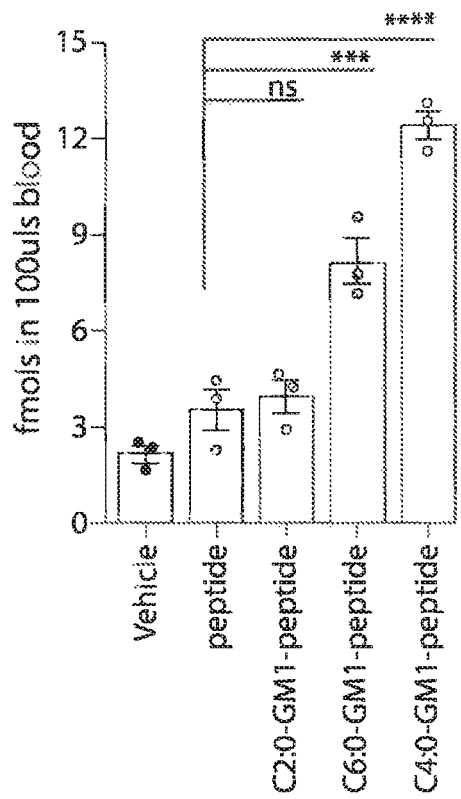

Notably, however, the C2:0-GM1-GLP-1 fusion molecule had no effect on glucose tolerance (FIG. 5D) and was not detectably absorbed after gastric gavage (FIG. 9B), even though this molecule was readily transported across epithelial monolayers in vitro (FIG. 1C). This may be explained by lower affinity of the C2:0- (and lyso-) ceramide domains for incorporation into cell membranes, as inferred from membrane loading and release assays (FIG. 38 and FIG. 7D). The difference in biology (transcytosis in vitro versus absorption in vivo) becomes apparent only in vivo where the conditions for epithelial uptake and transport are not optimized as they are in vitro. Thus, although it seemed at first glance that further shortening of the fatty acid beyond C4:0 should amplify transepithelial transport and thus clinical utility, this was not the case and the result informs further development of the technology.

In summary, fusion of therapeutic peptides to GM1 and GM3 glycosphingolipids with short fatty acids enables their active transport across tight epithelial barriers by transcytosis. In the case of the incretin hormone GLP-1, fusion to the lipid carriers allows for gastric (oral) absorption with high bioavailability and the expected effects on blood glucose, highlighting the potential use of this technology in clinical applications.

Discussion

The findings described herein delineate a novel synthetic method for enabling absorption of therapeutic peptides across mucosal surfaces in vivo. The approach is based on the natural biology of lipid sorting for the glycosphingolipids, which depends primarily on the structure of the ceramide domain structure to allow for trafficking in the transcytotic pathway, and thus actively transport across mucosal surfaces without barrier disruption. For applications requiring systemic drug delivery, non-native glycosphingolipid carriers with ceramide domains containing short-chain fatty acids are required to allow for efficient release from cell membranes into the circulation after transcytosis. The apparent high level of intestinal bioavailability enabled by the glycosphingolipid carriers is unprecedented.

The mechanism(s) for transceilular trafficking co-opted by the cis-unsaturated or short chain fatty acid glycosphingolipids are not fully understood. The most robust sorting event for GM1 glycosphingolipids appears to occur in the early endosome where long saturated chain ceramides are trafficked to the late endosome/lysosome, and the cis-unsaturated and short-chain glycoceramides are not ((8) and Schmieder and fencer unpublished results). It is possible the unsaturated and short-chain ceramide domains engage sorting mechanisms that dictate their trafficking to the recycling endosome and elsewhere, but it is also possible that their trafficking might be stochastic after escape from the lysosomal pathway, essentially tracking along with bulk membrane flow. In other words, the robust sorting event may occur only for the long chain saturated glycosphingolipids, directing them to the lysosome.

Another key structural feature enabling this technology must be the oligosaccharide head group. This domain traps the ceramide lipid in the outer membrane leaflet, preventing flip-flop between leaflets and thus rendering the molecule dependent on membrane dynamics for movement throughout the cell—an essential feature for a trafficking vehicle. As shown by our studies using GM3, the extracellular oligosaccharide can in some cell types also affect the efficiency of transepithelial transport. It may be possible that the tethering of the lipid to the membrane surface measured was enhanced by binding to adjacent membrane lectins. Differences have also been reported between GM1 and GM3 with respect to plasma membrane localization and bilayerkurvature dynamics in vitro (24, 28).

In the case of transport across mucosal barriers, several applications for the glycosphingolipids of relevance to clinical medicine are provided herein. One would be as vehicles for systemic delivery of peptide hormones as demonstrated here, or for topical delivery of agonist or antagonist peptides to specific mucosal surfaces. Another would be for delivery of antigens or adjuvants to enable mucosal vaccination or oral tolerance. It is possible that these glycosphingolipids will transport therapeutic proteins in the same way. Finally, while the biology of endosomes in endothelial cells is much less well understood at least some of the basic principles for lipid sorting in epithelial cells will apply to this cell type; and the glycosphingolipid carriers defined here may also be used to enable transport of biologics across tight endothelial barriers.

Materials and Methods

Transcytosis Assay

T84 or MDCK-H cells plated on 24-well Transwell® inserts (polyester membranes, Costar) were washed and equilibrated in DMEM without serum containing defatted-BSA (df-BSA). Unconjugated reporter peptide or GM1-peptide fusions at 0.1 µM complexed to df-BSA in a 1:1 ratio were then added apically for 3 hours. An excess of BSA (1% wt volume) was added basolaterally to aid in extraction of lipid from membranes. After a 3 hour continuous incubation, 1 mL basolateral media was collected and incubated with 10 µls magnetic streptavidin sepharose beads overnight at 4° C., washed with TBS-Tween, and eluted in 95% formamide/10 mM EDTA/0.4 mg/mL biotin. For detection of the reporter peptide or GM1-peptide fusion, fluorescence was mad using an Infinite M1000 plate reader (Tecan). For each biological replicate concentrations were calculated from standard curves for each compound.

In Vivo Studies

WT C57/BL/6 mice (male 7-9 weeks old) were purchased from Jackson Laboratory (Maine USA) and acclimatized for one week. For intestinal absorption experiments, mice that were fasted overnight were lightly anesthetized with isoflurane and fed a 0.5 nmol/kg dose in a 200 ul gavage volume. Compounds were diluted in PBS containing df-BSA in a 1:1 ratio prior to administration to mice. For analysis of systemic absorption, blood samples were taken using standard cardiac puncture procedures at 15 or 30 minutes after compound administration. 100 µls blood was diluted with 400 µls RIPA buffer and incubated with 10 µls streptavidin sepharose overnight at 4° C., washed, and eluted in 95% formamide/10 mM EDTA/0.4 mg/mL biotin as in our in vitro assay.

Liver tissue was flash frozen in liquid nitrogen and ground with a chilled mortar and pestle on dry ice. After obtaining dry weight, samples were homogenized in 1 mL RIPA buffer, centrifuged, and supernatant incubated with 10 µls strepta-vidin sepharose and bound molecules eluted with 95% formamide/10 mM EDTA/0.4 mg/mL biotin. Amount of compound accumulated to the liver was normalized per mg dry weight.

For intraperitoneal glucose tolerance tests, a 10 nmol/kg dose was used to gavage overnight-fasted WT C5/BL/6 mice (male 7-9 weeks old) with GM1-GLP-1 fusion molecules or unfused GLP-1. Glucose measurements following i.p. administration of 2 mg/g glucose solution were obtained from tail vein blood applied directly to glucose strips as in (16).

Membrane Loading and Lipid Release into Solution

MDCK-II cells were plated on 96-well plates the day prior to the experiment. Cells were washed with 10° C. serum-free DMEM (no phenol red) and equilibrated with DMEM containing 0.1 µmM df-BSA for 15 minutes. Cells were loaded for 45 minutes at 10° C. with 0.1 µM GM1-peptide molecule with a molar ratio of 1:1 (lipid:df-BSA). After loading, cells were washed, warmed to 37° C. degrees in DMEM (no phenol red) to allow for proper lipid incorporation, and incubated with 0.25% trypsin in HBSS to release adherent glycosphingolipids not incorporated into the membrane bilayer.

Cells were then incubated in DMEM alone or DMEM containing 1% df-BSA for 2 minutes, 15 minutes, or 1 hour. After the indicated time, media was collected and GM1-peptide molecules released into solution quantified using standards for each compound. Cells were subsequently lysed in RIPA buffer and the amount of cell-associated GM1-peptide quantified using known standards. Amount of GM1-peptide released into the solution was calculated as a ratio of total lipid incorporated (i.e., GM1-peptide in media+cell associated GM1-peptide).

Synthesis of Ganglioside-Peptide Conjugates

Gangliosides of different fatty acid species were supplied by Prof. Sandro Sonnino (U. Milan, Italy). Peptides containing modified functional residues were custom synthesized by Novo Nordisk (DK). Synthesis of peptide-lipid conjugates was accomplished by a modified method previously published (16). In a typical 2 mL reaction, 2 mg (approximately 1300 nmoles depending on fatty acid) of ganglioside was oxidized with sodium periodate (13 µmoles) in oxidation buffer (100 mM sodium acetate pH 5.5, 150 mM NaCl) for 30 minutes on ice and protected from light. The reaction was quenched by addition of glycerol (5% final). The reaction was desalted by Bond Elut SepPak C18 cartridge (Agilent, MA) and methanol used to elute from the column was removed by Speed Vac concentration (Savant). The oxidized product was then reconstituted in 2 mL PBS pH 6.9 in the presence of 10% DMF and reacted with 2700 nmoles of arninooxy-containing peptide in the presence of 10 mM aniline (29). The reaction was incubated for 20 hours at room temperature with mixing on a nutator, where the GM1-peptide fusion product formed normally resulted in a white precipitate. The precipitate was separated from the solution by centrifugation, then resuspended in 400 µL 50% isopropanoiiwater after brief sonication. PBS pH 6.9 was added (200 µL) along with 4.8 µmoles of sodium cyanaborohydride and incubated for 3 hours to reduce the oxime bond. Lipid-peptide conjugates were purified by semi-preparative HPLC, and confirmed by either MALDI-TOF (AB Voyager), or ESI LG-MS (Agilent, MA).

Fluorescent Reporter Peptides

With exception of the fluorescent peptide described in FIGS. 6A-6C, which was done by maleimide linkage, the labeling of peptides with Alexa fluorophore was typically done via copper-mediated Click chemistry. 320 µM peptide-lipid fusions containing an N-terminal alkyne residue (propargylglycine) were reacted with equimolar concentrations of Alexa Fluor 488-azide under the following conditions. 50 mM Tris-Cl, 5 mM copper (II) sulfate, 100 mM sodium ascorbate, 37 mM (Tris[(1-benzyl-1H-1-1,2,3-triazol-4-yl)methyl]amine, TBTA in DMSO/t-butanol 1:4) 1 mM (Tris (2-carboxyethyl) phosphine hydrochloride, TCEP—Sigma) and reacted for 16 hours at room temperature with mixing via nutator. Products were purified by HPLC and confirmed by mass spectrometry. Products were lyophilized and stored at −20° C. Compounds were resuspended in 33% DMF/water to make stock solutions for assays. m/z mass spectrometry values were as follows: For GM1-C12:0 reporter conjugates with different functional groups on the peptide and d18:1 long chain base, alkyne=2475.5 Da(1+); biotin=2734.4 Da(1+); alkyne-biotin=2829.4 (Da) (1+); Alexa Fluor 488 maleimide=1552.2 Da and d20:1=1566.2 Da. For GM1-C16:0 species in this series, (2+) mass was observed at 1580.2 Da.

Most of the structure function studies with GM1 fatty acid species lyso to C12:1, were detected with a 3+ charge. m/z values for d18:1 and d20:1 sphingosine, respectively, were as follows: lyso=1101.1 Da (3+) and 1110.5 Da (3+); C2:0=1115.1 Da (3+) and 1124.5 Da (3+); C4:0=1124.5 Da (3+) and 1133.8 Da (3+); C6:0=1134.1 Da (3+) and 1142.5 Da (3+); C6:1=1133.1 Da (3+) and 1143.5 Da (3+); C12:0=1161.8 Da (3+) and 1171.2 Da (3+); C12:1=11161,1 Da (3+) and 1170.5 Da (3+), Free peptide was observed as a single ion peak at 2102,8 Da. For GM3 molecular species conjugates, m/z was observed at: C6:0=1212.1 Da (3+) and 1026.1 Da (3+); C12:0=1040.1 Da (3+) and 1054.1 Da (3+).

Synthesis of GLP1-Ganglioside and GLP-D-Conjugates

To generate bioactive GLP1 fusion lipids, two peptides were joined together via a triazole linkage. Long half-life GLP1 sequences were synthesized containing isobutyrate residues substituted at key dipeptidyl peptidase-4 (DPP-4) cleavage sites, and a C-terminal azido-lysine (FIGS. 5A and 6A), A Tobacco Etch Virus protease site (ENLYFQS) was originally designed into the sequence but was not used for the purposes of this paper. The peptide was joined to reporter peptide-lipid conjugates via N-terminal alkyne using Click chemistry as described above.

To synthesize the all-D GLP1-lipid fusions, peptides were made as a complete chain on solid phase, and contained aminooxy and biotin groups (FIG. 5). Linkage to oxidized ganglioside was performed as stated above. m/z values for the biologic GLP1-fusion were observed at: C2:0=1808.4 Da (4+); C6:0=1822.2 with free peptide seen as a 3+ charge at 2251.0 Da. For the all-D isomer version of GLP1, GLPD fused to GM1-C6:0, m/z was seen as a 3+ charge at 2251.0 Da and the free peptide as a 2+ charge at 2726.7 Da.

REFERENCES

1. P. L. Tuma, A. L. Hubbard, Transcytosis: crossing cellular barriers. *Physiol Rev* 83, 871-932 (2003).
2. K. E. Mostov, M. Verges, Y. Altschuler, Membrane traffic in polarized epithelial cells. *Curr Opin Cell Biol* 12, 483-490 (2000).
3. M. D. Garcia-Castillo, D. J. Chinnapen, W. I. Lencer, Membrane Transport across Polarized Epithelia. *Cold Spring Harb Perspect Biol* 9, (2017).
4. N. J. Abbott, Blood-brain barrier structure and function and the challenges for CNS drug delivery. *Journal of inherited metabolic disease* 36, 437-449 (2013).
5. W. M. Pardridge, Targeted delivery of protein and gene medicines through the blood-brain barrier. *Clinical pharmacology and therapeutics* 97, 347-361 (2015).
6. J. E. Preston, N. Joan Abbott, D. J. Begley, Transcytosis of macromolecules at the blood-brain barrier. *Adv Pharmacol* 71, 147-163 (2014).
7. J. M. Lajoie, E. V. Shusta, Targeting receptor-mediated transport for delivery of biologics across the blood-brain barrier. *Annual review of pharmacology and toxicology* 55, 613-631 (2015).
8. D. J. Chinnapen et al., Lipid Sorting by Ceramide Structure from Plasma Membrane to ER for the Cholera Toxin Receptor Ganglioside GM1. *Developmental cell* 23, 573-586 (2012).
9. M. Hao, S. Mukherjee, Y. Sun, F. R. Maxfield, Effects of cholesterol depletion and increased lipid unsaturation on the properties of endocytic membranes. *Journal Of Biological Chemistry.* 279, 14171-14178 (2004).
10. S. Mayor, J. F. Presley, F. R. Maxfield, Sorting of membrane components from endosomes and subsequent recycling to the cell surface occurs by a bulk flow process. *Journal Of Cell Biology.* 121, 1257-1269 (1993).
11. S. Mukherjee, T. T. Soe, F. R. Maxfield, Endocytic sorting of lipid analogues differing solely in the chemistry of their hydrophobic tails. *Journal Of Cell Biology.* 144, (1999).
12. D. A. Brown, lipid rafts, detergent-resistant membranes, and raft targeting signals. *Physiology* (Bethesda, Md. 21, 430-439 (2006).
13. K. Simons, R. Ehehalt, Cholesterol, lipid rafts, and disease. *J Clin Invest* 110, 597-603 (2002).
14. K. Simons, W. L. Vaz, Model systems, lipid rafts, and cell membranes. *Annu Rev Biophys Biomol Struct* 33, 269-295 (2004).
15. D. E. Saslowsky et el., Ganglioside GM1-mediated transcytosis of cholera toxin bypasses the retrograde pathway and depends on the structure of the ceramide domain. *Journal Of Biological Chemistry.* 288, 25804-25809 (2013).
16. Y. M. to Welscher, D. J. Chinnapen, L. Kaoutzani, R. J. Mrsny, W. I. Lencer, Unsaturated glycoceramides as molecular carriers for mucosal drug delivery of GLP-1. *Journal of controlled release: official journal of the Controlled Release Society* 175, 72-78 (2014).
17. D. J. Chinnapen, H. Chinnapen, D. Saslowsky, W. I. Lencer, Rafting with cholera toxin: endocytosis and trafficking from plasma membrane to ER. *FEMS Microbiol Lett* 266, 129-137 (2007).
18. R. A. Spooner, J. M. Lord, How Ricin and Shiga Toxin Reach the Cytosol of Target Cells: Retrotranslocation from the Endoplasmic Reticulum. *Current topics in microbiology and immunology*, (2011).
19. H. Ewers, A. Helenius, Lipid-mediated endocytosis. *Cold Spring Harb Perspect Biol* 3, a004721 (2011).
20. J. A. Cho et al., Insights on the trafficking and retrotranslocation of glycosphingolipid-binding bacterial toxins. *Front Cell infect Microbiol* 2, 51 (2012).

21. A. Oztan et al., Exocyst requirement for endocytic traffic directed toward the apical and basolateral poles of polarized MDCK cells. *Mol Biol Cell* 18, 3978-3992 (2007).
22. B. Nelms, N. F. Dalomba, W. Lencer, A targeted RNAI screen identifies factors affecting diverse stages of receptor-mediated transcytosis. *Journal Of Cell Biology.* 216, 511-525 (2017).
23. R. Pagano, in *Fluorescence microscopy of living cells in culture*, Y.-L. Wang, D. L. Taylor, Eds. (Academic Press, Boston, 1989), vol. 29.
24. L. Cantu, E. Del Favero, S. Sonnino, A. Prinetti, Gangliosides and the multiscale modulation of membrane structure. *Chem Phys Lipids* 164, 796-810 (2011).
25. L. van Bloemendaal, J. S. Ten Kulve, S. E. la Fleur, R. G. Ijzerman, M. Diamant, Effects of glucagon-like peptide 1 on appetite and body weight: focus on the CNS. *J Endocrinol* 221, T1-16 (2014).
26. K. M. Heppner, D. Perez-Tilve, GLP-1 based therapeutics: simultaneously combating T2DM and obesity. *Front Neurosci* 9, 92 (2015).
27. K. L. Tran et al., Overview of Glucagon-Like Peptide-1 Receptor Agonists for the Treatment of Patients with Type 2 Diabetes. *American health & drug benefits* 10, 178-188 (2017).
28. P. Janich, D. Corbeil, GM1 and GM3 gangliosides highlight distinct lipid microdomains within the apical domain of epithelial cells. *FEBS Lett* 581, 1783-1787 (2007).
29. A. Dirksen, P. E. Dawson, Rapid oxime and hydrazone ligations with aromatic aldehydes for biomolecular labeling. *Bioconjugate chemistry* 19, 2543-2548 (2008).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A method of enhancing the half-life of an agent in a subject in need thereof, the method comprising administering to the subject a delivery vehicle comprising a glycosphingolipid and an agent to be delivered, wherein the glycosphingolipid comprises an oligosaccharide, and (a) a ceramide that comprises a short-chain fatty acid (C1-C3), or (b) a ceramide that does not contain a fatty acid, and wherein the agent to be delivered is attached to the oligosaccharide of the glycosphingolipid.

2. The method of claim 1, wherein the glycosphingolipid is a ganglioside.

3. The method of claim 2, wherein the ganglioside comprises a sialic acid.

4. The method of claim 2, wherein the ganglioside is monosialotetrahexosylganglioside (GM1).

5. The method of claim 2, wherein the ganglioside is monosialodihexosylganglioside (GM3).

6. A method of treating a disease or condition in a subject in need thereof, the method comprising administering to the subject an effective amount of a delivery vehicle comprising a glycosphingolipid and an agent to be delivered, wherein the glycosphingolipid comprises an oligosaccharide, and (a) a ceramide that comprises a short-chain fatty acid (C1-C3), or (b) a ceramide that does not contain a fatty acid, and wherein the agent to be delivered is attached to the oligosaccharide of the glycosphingolipid, wherein the effective amount is an amount sufficient to ameliorate/reduce the extent to which the disease or condition occurs in the subject.

7. The method of claim 6, wherein the glycosphingolipid is a ganglioside.

8. The method of claim 7, wherein the ganglioside comprises a sialic acid.

9. The method of claim 7, wherein the ganglioside is monosialotetrahexosylganglioside (GM1).

10. The method of claim 7, wherein the ganglioside is monosialodihexosylganglioside (GM3).

11. The method of claim 6, wherein the ceramide comprises a short-chain fatty acid (C1-C3) with no double bonds between carbon atoms.

12. The method of claim 6, wherein the ceramide comprises a C2 fatty acid chain with a double bond between carbon atoms.

13. The method of claim 6, wherein the ceramide comprises a C3 fatty acid chain with at least one double bond between carbon atoms.

14. The method of claim 6, wherein the ceramide does not comprise a fatty acid.

15. The method of claim 6, wherein the agent to be delivered is selected from the group consisting of proteins, peptides, nucleic acids, polysaccharides and carbohydrates, lipids, glycoproteins, small molecules, synthetic organic and inorganic drugs exerting a biological effect when administered to a subject, and combinations thereof.

16. The method of claim 6, wherein the agent to be delivered is a therapeutic agent.

17. The method of claim 6, wherein the agent to be delivered is a protein or a peptide.

18. The method of claim 17, wherein the protein or peptide is GLP-1, or a functional fragment thereof.

19. The method of claim 6, wherein the delivery vehicle is administered parenterally.

20. The method of claim 6, wherein the delivery vehicle is administered nonparenterally or subcutaneously.

* * * * *